United States Patent
Bertozzi et al.

(10) Patent No.: US 11,656,233 B2
(45) Date of Patent: May 23, 2023

(54) MULTIPLEX ISOTYPE-SPECIFIC ANTIBODY DETECTION

(71) Applicant: The Board of Trustees of the Leland Stanford Junior University, Stanford, CA (US)

(72) Inventors: Carolyn Bertozzi, Menlo Park, CA (US); Stephen J. Galli, Portola Valley, CA (US); Kaori Mukai, Cambridge, MA (US); Peter Robinson, San Francisco, CA (US); Cheng-ting Tsai, Palo Alto, CA (US); Mindy Tsai, Palo Alto, CA (US)

(73) Assignee: The Board of Trastees of the Leland Stanford Junior University, Stanford, CA (US)

( * ) Notice: Subject to any disclaimer, the term of this patent is extended or adjusted under 35 U.S.C. 154(b) by 614 days.

(21) Appl. No.: 16/497,668

(22) PCT Filed: Mar. 29, 2018

(86) PCT No.: PCT/US2018/025299
§ 371 (c)(1),
(2) Date: Sep. 25, 2019

(87) PCT Pub. No.: WO2018/183779
PCT Pub. Date: Oct. 4, 2018

(65) Prior Publication Data
US 2020/0309784 A1    Oct. 1, 2020

Related U.S. Application Data

(60) Provisional application No. 62/479,278, filed on Mar. 30, 2017.

(51) Int. Cl.
| | |
|---|---|
| G01N 33/68 | (2006.01) |
| C12N 15/11 | (2006.01) |
| C12Q 1/6804 | (2018.01) |
| C12Q 1/6806 | (2018.01) |
| C12Q 1/686 | (2018.01) |
| G01N 33/564 | (2006.01) |

(52) U.S. Cl.
CPC .......... *G01N 33/686* (2013.01); *C12N 15/11* (2013.01); *C12Q 1/6804* (2013.01); *C12Q 1/6806* (2013.01); *C12Q 1/686* (2013.01); *G01N 33/564* (2013.01); *G01N 2458/10* (2013.01)

(58) Field of Classification Search
CPC ............... G01N 33/686; G01N 33/564; G01N 2458/10; C12N 15/11; C12Q 1/6804; C12Q 1/6806; C12Q 1/686; C12Q 2521/101; C12Q 2521/501; C12Q 2525/205; C12Q 2537/143; C12Q 2563/179
See application file for complete search history.

(56) References Cited

U.S. PATENT DOCUMENTS

| | | |
|---|---|---|
| 2011/0020373 A1 | 1/2011 | Saxon et al. |
| 2013/0165335 A1 | 6/2013 | Lea |
| 2016/0289663 A1 | 10/2016 | Kiyokawa et al. |
| 2018/0100181 A1 | 4/2018 | Robinson et al. |

FOREIGN PATENT DOCUMENTS

| | | |
|---|---|---|
| EP | 2022507 A1 | 2/2009 |
| WO | 95/005399 A1 | 2/1995 |
| WO | 2011/103172 A1 | 8/2011 |
| WO | 2014/207245 A1 | 12/2014 |
| WO | 2016/168711 A1 | 4/2016 |
| WO | 2017/068116 A1 | 4/2017 |

OTHER PUBLICATIONS

Chapman et al. (2015) Technological Innovations for High-Throughput Approaches to In Vitro Allergy Diagnosis. Curr Allergy Asthma Rep. 15(7):36.
Feyzkhanova et al. (2014) Development of hydrogel biochip for in vitro allergy diagnostics. J. Immunol Methods 406:51-7.
European Search Report for European Application No. 18777364.3—PCT/US2018/025299.
Ferreira et al. (2014) Molecular approach to allergy diagnosis and therapy. Yonsei Med. J. 55:839-852.
Chapman et al. (2015) Technological Innovations for High-Throughput Approaches to In Vitro Allergy Diagnosis Curr. Allergy Asthma Rep. 15:36.
Tsai et al. (2016) Ultrasensitive Antibody Detection by Agglutination-PCR (ADAP). ACS Cent Sci 2:139-147.
Fredriksson et al. (2007) Multiplexed protein detection by proximity ligation for cancer biomarker validation. Nat. Methods 4:327-329.
PCT/US2018/025299 (published as WO 2018/183779) International Search Report dated Jul. 26, 2018, 6 pages.

*Primary Examiner* — Cynthia B Wilder
(74) *Attorney, Agent, or Firm* — Jenny L. Buchbinder; Bozicevic, Field & Francis LLP

(57) ABSTRACT

Methods and reagents for multiplex detection of antibodies are disclosed. In particular, the invention relates to multiplex detection of antibodies using antigen-DNA and antibody-binding agent-DNA conjugates carrying DNA barcodes for identifying and quantitating disease-relevant antibody isotypes, such as those involved in allergic responses, autoimmune diseases, infections, and inflammation.

16 Claims, 24 Drawing Sheets

Specification includes a Sequence Listing.

|  | PCR-based assay | ImmunoCAP |
|---|---|---|
| Sample volume | 1 μl | 200 μl |
| Cost | $5 | $500 |
| Turn around time | < 4 h | < 6 h |
| Instrument | qPCR machinery | Immunoassay analyzer |

FIG. 10E

SEQUENCE LISTING

```
<160> NUMBER OF SEQ ID NOS: 21

<210> SEQ ID NO 1
<211> LENGTH: 40
<212> TYPE: DNA
<213> ORGANISM: Artificial Sequence
<220> FEATURE:
<223> OTHER INFORMATION: DNA 1A
<220> FEATURE:
<221> NAME/KEY: source
<222> LOCATION: (1)..(40)
<223> OTHER INFORMATION: sequence is synthesized

<400> SEQUENCE: 1
caggtagtag tacgtctgtt tcacgatgag actggatgaa                           40

<210> SEQ ID NO 2
<211> LENGTH: 40
<212> TYPE: DNA
<213> ORGANISM: Artificial Sequence
<220> FEATURE:
<223> OTHER INFORMATION: DNA 1B
<220> FEATURE:
<221> NAME/KEY: source
<222> LOCATION: (1)..(40)
<223> OTHER INFORMATION: sequence is synthesized

<400> SEQUENCE: 2
```

```
tcacggtagc ataaggtgca agataatact ctcgcagcac                    40
```

<210> SEQ ID NO 3
<211> LENGTH: 20
<212> TYPE: DNA
<213> ORGANISM: Artificial Sequence
<220> FEATURE:
<223> OTHER INFORMATION: Reverse primer 1
<220> FEATURE:
<221> NAME/KEY: source
<222> LOCATION: (1)..(20)
<223> OTHER INFORMATION: sequence is synthesized
<400> SEQUENCE: 3

```
gtgctgcgag agtattatct                                          20
```

<210> SEQ ID NO 4
<211> LENGTH: 20
<212> TYPE: DNA
<213> ORGANISM: Artificial Sequence
<220> FEATURE:
<223> OTHER INFORMATION: Forward primer 1
<220> FEATURE:
<221> NAME/KEY: source
<222> LOCATION: (1)..(20)
<223> OTHER INFORMATION: sequence is synthesized
<400> SEQUENCE: 4

```
caggtagtag tacgtctgtt                                          20
```

<210> SEQ ID NO 5
<211> LENGTH: 40
<212> TYPE: DNA
<213> ORGANISM: Artificial Sequence
<220> FEATURE:
<223> OTHER INFORMATION: DNA 2A
<220> FEATURE:
<221> NAME/KEY: source
<222> LOCATION: (1)..(40)
<223> OTHER INFORMATION: sequence is synthesized
<400> SEQUENCE: 5

```
ggcctcctcc aattaaagaa tcacgatgag actggatgaa                    40
```

<210> SEQ ID NO 6
<211> LENGTH: 40
<212> TYPE: DNA
<213> ORGANISM: Artificial Sequence
<220> FEATURE:
<223> OTHER INFORMATION: DNA 2B
<220> FEATURE:
<221> NAME/KEY: source
<222> LOCATION: (1)..(40)
<223> OTHER INFORMATION: sequence is synthesized
<400> SEQUENCE: 6

```
tcacggtagc ataaggtgca gtacccaaat aacggttcac                    40
```

<210> SEQ ID NO 7
<211> LENGTH: 20
<212> TYPE: DNA
<213> ORGANISM: Artificial Sequence
<220> FEATURE:
<223> OTHER INFORMATION: Reverse primer 2
<220> FEATURE:
<221> NAME/KEY: source
<222> LOCATION: (1)..(20)
<223> OTHER INFORMATION: sequence is synthesized
<400> SEQUENCE: 7
gtgaaccgtt atttgggtac                                              20

<210> SEQ ID NO 8
<211> LENGTH: 20
<212> TYPE: DNA
<213> ORGANISM: Artificial Sequence
<220> FEATURE:
<223> OTHER INFORMATION: Forward primer 2
<220> FEATURE:
<221> NAME/KEY: source
<222> LOCATION: (1)..(20)
<223> OTHER INFORMATION: sequence is synthesized

<400> SEQUENCE: 8
ggcctcctcc aattaaagaa                                              20

<210> SEQ ID NO 9
<211> LENGTH: 40
<212> TYPE: DNA
<213> ORGANISM: Artificial Sequence
<220> FEATURE:
<223> OTHER INFORMATION: DNA 3A
<220> FEATURE:
<221> NAME/KEY: source
<222> LOCATION: (1)..(40)
<223> OTHER INFORMATION: sequence is synthesized

<400> SEQUENCE: 9
ggatcactcc aactagacta tcacgatgag actggatgaa                        40

<210> SEQ ID NO 10
<211> LENGTH: 40
<212> TYPE: DNA
<213> ORGANISM: Artificial Sequence
<220> FEATURE:
<223> OTHER INFORMATION: DNA 3B
<220> FEATURE:
<221> NAME/KEY: source
<222> LOCATION: (1)..(40)
<223> OTHER INFORMATION: sequence is synthesized

<400> SEQUENCE: 10
tcacggtagc ataaggtgca gttatatctg ccactgtcac                        40

<210> SEQ ID NO 11
<211> LENGTH: 20
<212> TYPE: DNA
<213> ORGANISM: Artificial Sequence
<220> FEATURE:
<223> OTHER INFORMATION: Reverse primer 3
<220> FEATURE:
<221> NAME/KEY: source
<222> LOCATION: (1)..(20)
<223> OTHER INFORMATION: sequence is synthesized

<400> SEQUENCE: 11
gtgacagtgg cagatataac                                              20

<210> SEQ ID NO 12
<211> LENGTH: 20
<212> TYPE: DNA
<213> ORGANISM: Artificial Sequence
<220> FEATURE:
<223> OTHER INFORMATION: Forward primer 3
<220> FEATURE:
<221> NAME/KEY: source
<222> LOCATION: (1)..(20)
<223> OTHER INFORMATION: sequence is synthesized

```
<400> SEQUENCE: 12
ggatcactcc aactagacta                                                      20

<210> SEQ ID NO 13
<211> LENGTH: 40
<212> TYPE: DNA
<213> ORGANISM: Artificial Sequence
<220> FEATURE:
<223> OTHER INFORMATION: DNA 4A
<220> FEATURE:
<221> NAME/KEY: source
<222> LOCATION: (1)..(40)
<223> OTHER INFORMATION: sequence is synthesized

<400> SEQUENCE: 13
agagtccact tcccataatg tcacgatgag actggatgaa                                40

<210> SEQ ID NO 14
<211> LENGTH: 40
<212> TYPE: DNA
<213> ORGANISM: Artificial Sequence
<220> FEATURE:
<223> OTHER INFORMATION: DNA 4B
<220> FEATURE:
<221> NAME/KEY: source
<222> LOCATION: (1)..(40)
<223> OTHER INFORMATION: sequence is synthesized

<400> SEQUENCE: 14
tcacggtagc ataaggtgca cggtactgtc agcatagttc                                40

<210> SEQ ID NO 15
<211> LENGTH: 20
<212> TYPE: DNA
<213> ORGANISM: Artificial Sequence
<220> FEATURE:
<223> OTHER INFORMATION: Reverse primer 4
<220> FEATURE:
<221> NAME/KEY: source
<222> LOCATION: (1)..(20)
<223> OTHER INFORMATION: sequence is synthesized

<400> SEQUENCE: 15
gaactatgct gacagtaccg                                                      20

<210> SEQ ID NO 16
<211> LENGTH: 20
<212> TYPE: DNA
<213> ORGANISM: Artificial Sequence
<220> FEATURE:
<223> OTHER INFORMATION: Forward primer 4
<220> FEATURE:
<221> NAME/KEY: source
<222> LOCATION: (1)..(20)
<223> OTHER INFORMATION: sequence is synthesized

<400> SEQUENCE: 16
agagtccact tcccataatg                                                      20

<210> SEQ ID NO 17
<211> LENGTH: 40
<212> TYPE: DNA
<213> ORGANISM: Artificial Sequence
<220> FEATURE:
<223> OTHER INFORMATION: DNA 5A
<220> FEATURE:
<221> NAME/KEY: source
<222> LOCATION: (1)..(40)
<223> OTHER INFORMATION: sequence is synthesized
```

```
<400> SEQUENCE: 17
ctacgactag gagatagatg tcacgatgag actggatgaa                              40

<210> SEQ ID NO 18
<211> LENGTH: 40
<212> TYPE: DNA
<213> ORGANISM: Artificial Sequence
<220> FEATURE:
<223> OTHER INFORMATION: DNA 5B
<220> FEATURE:
<221> NAME/KEY: source
<222> LOCATION: (1)..(40)
<223> OTHER INFORMATION: sequence is synthesized

<400> SEQUENCE: 18
tcacggtagc ataaggtgca gttatgtata gtacgctcgc                              40

<210> SEQ ID NO 19
<211> LENGTH: 20
<212> TYPE: DNA
<213> ORGANISM: Artificial Sequence
<220> FEATURE:
<223> OTHER INFORMATION: Reverse primer 5
<220> FEATURE:
<221> NAME/KEY: source
<222> LOCATION: (1)..(20)
<223> OTHER INFORMATION: sequence is synthesized

<400> SEQUENCE: 19
gcgagcgtac tatacataac                                                    20

<210> SEQ ID NO 20
<211> LENGTH: 20
<212> TYPE: DNA
<213> ORGANISM: Artificial Sequence
<220> FEATURE:
<223> OTHER INFORMATION: Forward primer 5
<220> FEATURE:
<221> NAME/KEY: source
<222> LOCATION: (1)..(20)
<223> OTHER INFORMATION: sequence is synthesized

<400> SEQUENCE: 20
ctacgactag gagatagatg                                                    20

<210> SEQ ID NO 21
<211> LENGTH: 18
<212> TYPE: DNA
<213> ORGANISM: Artificial Sequence
<220> FEATURE:
<223> OTHER INFORMATION: Bridge oligo
<220> FEATURE:
<221> NAME/KEY: source
<222> LOCATION: (1)..(18)
<223> OTHER INFORMATION: sequence is synthesized

<400> SEQUENCE: 21
ctaccgtgat tcatccag                                                      18
```

MULTIPLEX ISOTYPE-SPECIFIC ANTIBODY DETECTION

STATEMENT REGARDING FEDERALLY SPONSORED RESEARCH OR DEVELOPMENT

This invention was made with Government support under contracts DK108781 and AR067145 awarded by the National Institutes of Health. The Government has certain rights in the invention.

TECHNICAL FIELD

The present invention pertains generally to the field of immunology and methods of detecting specific antibody isotypes. In particular, the invention relates to multiplex detection of antibodies using antigen-DNA and antibody-binding agent-DNA conjugates carrying DNA barcodes for identifying and quantitating disease-relevant antibody isotypes, such as those involved in allergic responses, autoimmune diseases, infections, and inflammation.

BACKGROUND

Allergy is a prevalent immune hypersensitivity disease that affects more than 20% of the U.S. population (Gupta et al. (2011) Pediatrics 128:e9-e17, Akinbami et al. (2012) NCHS Data Brief 94:1-8). Exposure to allergens can lead to life-threatening disorders such as anaphylaxis (Chinthrajah et al. (2016) J. Allergy Clin. Immunol. 137:984-997) and allergic asthma (Milgrom et al. (1999) N. Engl. J. Med. 341:1966-1973). Novel anti-allergy therapies directly modify the immunological actors within the allergic response (Milgrom et al., supra). For example, recent oral immunotherapy trials have shown promise towards inducing tolerance to peanut allergens (Syed et al. (2014) J. Allergy Clin. Immunol. 133:500-510, Vickery et al. (2016) J. Allergy Clin. Immunol. S0091-6749:30531-0), one of the most common allergies that afflicts millions of patients worldwide (Gupta et al., supra). These exciting new therapies all require cost-effective, sensitive and reliable diagnostics to identify eligible patients for therapy and to track their response to treatment. While several technologies are currently deployed for this purpose, they consume large amounts of sample and lack the cost-effectiveness to meet the clinical needs of allergists and their patients.

One of the most common allergy tests is the skin-prick test (SPT, Bernstein et al. (2008) Ann Allergy Asthma Immunol. 100:S1-148). This test measures allergic responses by subcutaneously injecting allergen extracts and observing the allergic lesion that develops. Although the SPT test is inexpensive and can be performed quickly, its invasiveness and potential system complications limit widespread acceptance, especially in pediatric populations (Liccardi et al. (2006) J. Investig. Allergol. Clin. Immunol. 16:75-78). Furthermore, results from the SPT fluctuate widely, as physicians rely on poorly-standardized parameters for quantification (Fatteh et al. (2014) Allergy Asthma Clin. Immunol. 10(1):44).

Molecular tools have shown promise as complementary diagnostic tools with stronger and more reliable quantitation power (Ferreira et al. (2014) Yonsei Med. J. 55:839-852). Measurement of total IgE (tIgE) and allergen-specific IgE (sIgE) reliably identify, from a simple blood test, the presence of the types of antibodies (i.e., sIgEs) that are required for a patient to exhibit an allergic response to a given allergen (Ferreira et al., supra). However, several technical challenges limit the power of the current generation of IgE molecular tests. The IgE concentration in serum is very low (100-500 ng/mL) in comparison to other highly abundant and potentially interfering proteins such as IgG (40-50 mg/mL) (Amarasekera et al. (2011) Asia Pac Allergy 1:12-15). The 5-6 orders of magnitude difference in concentration frustrates the development of assays to detect the minute amounts of IgE within a sea of irrelevant serum proteins.

Further exacerbating the issue, protein impurities from whole-allergen extracts often adulterate allergen-specific assays (Ferreira et al., supra). These impurities cross-react with non-allergenic antibodies to reduce the specificity of these tests (Ferreira et al., supra). Recently work has identified exact allergen proteins that correlate strongly with the underlying allergy. Assays that make use of precise allergen proteins (as opposed to whole extracts) form the basis of "component-resolved allergy diagnostics" (Ferreira et al., supra). These tests display significantly improved accuracy for IgE-based allergy testing (Ferreira et al., supra).

The ImmunoCAP platform (Phadia, Thermo Fischer) dominates the diagnostic landscape for component-resolved allergy IgE testing (Chapman et al. (2015) Curr. Allergy Asthma Rep. 15:36). A key component of ImmunoCAP is a dense, allergen-impregnated polymer (Chapman et al., supra). The high allergen loading onto the polymer efficiently captures a large portion of allergen-binding antibodies from the sample (Chapman et al., supra). This approach renders ImmunoCAP much more sensitive than the traditional ELISA assay format, which does not employ polymer-based capture methods. However, the increased allergen consumption increases the cost of ImmunoCAP testing ($50 per sample). A 5-component ImmunoCAP test for peanut allergy can cost as much as $250 and require 200 µL of plasma. Despite the enhanced sensitivity and specificity of high-performance component-resolved allergy testing, its relatively high cost and sample consumption signals an opportunity for novel diagnostic technologies with improved qualities.

Thus, there remains a need for better methods of diagnostic testing for antibodies that are sensitive, specific, and cost-effective.

SUMMARY

The present invention is based on the development of sensitive, reliable diagnostic assays for the detection of antibodies of specific isotypes. Antigen-DNA conjugates and antibody-binding agent-DNA conjugates carrying DNA barcodes are used to detect the presence of specific antibodies. The use of a DNA barcode allows antibodies to be identified by nucleic acid-based detection methods, such as polymerase chain reaction (PCR), isothermal amplification, or microarray analysis. In particular, the methods of the invention will allow monitoring of disease-relevant antibodies associated with immune disorders, such as allergies, autoimmune diseases, infection, or inflammation and thereby enable better disease management.

In one aspect, the invention includes a method of detecting a target antibody isotype in a sample, the method comprising: a) contacting the sample with i) an antibody-binding agent conjugated to a first DNA molecule comprising a first portion of a barcode and ii) an antigen conjugated to a second DNA molecule comprising a second portion of a barcode, wherein the antigen binds to the target antibody isotype in the sample, if present, and the antibody-binding agent specifically binds to the target antibody isotype resulting in formation of a complex; b) connecting the first DNA molecule to the second DNA molecule in the complex, wherein the first portion of the barcode and the second portion of the barcode are joined to form a complete barcode; and c) detecting the complete barcode as an indication of the presence of the target antibody isotype in the sample.

Connecting the first DNA molecule to the second DNA molecule can be accomplished in various ways. In one embodiment, the method comprises: a) contacting the complex with a bridge oligonucleotide, wherein the bridge oligonucleotide comprises a first portion sufficiently complementary to and capable of hybridizing with the first DNA molecule, and a second portion sufficiently complementary to and capable of hybridizing with the second DNA molecule, wherein the first DNA molecule and the second DNA molecule are in sufficient proximity to each other in the complex to simultaneously hybridize to the bridge oligonucleotide; and b) ligating the first DNA molecule to the second DNA molecule in the complex to produce a ligation product comprising the complete barcode. In another embodiment, the method comprises hybridization of a nucleotide sequence in the first DNA molecule to a complementary nucleotide sequence in the second DNA molecule, and using a polymerase to extend the hybridized first and second DNA molecules to produce a nucleic acid comprising the complete barcode. The polymerase reaction can be carried out, for example, under isothermal conditions.

In certain embodiments, the complete barcode is detected using PCR, isothermal amplification, or microarray analysis. In another embodiment, the method further comprises quantitating the amount of the target antibody isotype, for example, using quantitative PCR (qPCR).

In certain embodiments, the sample is obtained from a subject having an immune disorder such as an allergy, an infection, an autoimmune disorder, an inflammatory disorder. The sample is typically blood, plasma, or serum, but can be any sample comprising antibodies.

In certain embodiments, the methods of the invention are used for detecting anti-human immunodeficiency virus (HIV) antibodies for diagnosing an HIV infection. For detection of anti-HIV antibodies, the antigen conjugated to the second DNA molecule is an HIV antigen. Exemplary HIV antigens include HIV-1 antigens, HIV-2 antigens, HIV-1/2 antigens, p16, p14, p24, p55, gp120, gp160, gp41, and gp36.

In certain embodiments, the target antibody analyte is selected from the group consisting of an immunoglobulin E (IgE), an immunoglobulin M (IgM), an immunoglobulin G (IgG), an immunoglobulin A (IgA) and an immunoglobulin D (IgD). In certain embodiments, the antibody is an IgG of a IgG1, IgG2, IgG3, or IgG4 subtype.

The antibody-binding agent can be any agent that specifically binds to a target antibody isotype. Examples of antibody-binding agents include, without limitation, antibodies, antibody fragments, antibody mimetics, and aptamers.

In certain embodiments, the antibody-binding agent comprises an antibody that specifically binds to the target antibody isotype. The antibody can be, for example, a monoclonal antibody, a polyclonal antibody, a chimeric antibody, a nanobody, a recombinant fragment of an antibody, an Fab fragment, an Fab' fragment, an F(ab')$_2$ fragment, an F$_v$ fragment, or an scF$_v$ fragment. In certain embodiments, the antibody that specifically binds to the target antibody isotype is selected from the group consisting of an anti-IgE antibody, an anti-IgM antibody, an anti-IgG antibody, an anti-IgA antibody, and an anti-IgD antibody.

In other embodiments, the antibody-binding agent comprises an aptamer that specifically binds to the target antibody isotype. For example, a DNA, RNA, xeno-nucleic acid (XNA), or peptide aptamer that specifically binds to the target antibody isotype may be used.

In yet other embodiments, the antibody-binding agent comprises an antibody mimetic that specifically binds to the target antibody isotype. Exemplary antibody mimetics include affibody molecules, affilins, affimers, affitins, alphabodies, anticalins, avimers, darpins, fynomers, and monobodies.

In another embodiment, the method further comprises adding a plurality of antibody-binding agent-DNA conjugates to the sample, wherein each antibody-binding agent is conjugated to a DNA molecule comprising a different barcode sequence and each antibody-binding agent is capable of binding to a different target antibody isotype to allow multiplex detection of a plurality of target antibody isotypes in the sample. In certain embodiments, the antibody-binding agent-DNA conjugates are selected from the group consisting of an anti-IgE secondary antibody-DNA conjugate for detection of IgE, an anti-IgM secondary antibody-DNA conjugate for detection of IgM, an anti-IgG secondary antibody-DNA conjugate for detection of IgG, an anti-IgA secondary antibody-DNA conjugate for detection of IgA, and an anti-IgD secondary antibody DNA conjugate for detection of IgD.

In certain embodiments, the method is used for detecting allergen-specific antibodies, wherein the method is capable of detecting IgE at concentrations greater than or equal to 0.01 ng/mL.

In certain embodiments, the antigen-DNA conjugate comprises an antigen selected from the group consisting of an allergen, an autoimmune disease antigen, a cancer antigen, and a pathogen antigen.

In another embodiment, the invention includes a method of detecting a target antibody isotype in a sample, the method comprising: a) adding an antibody-binding agent conjugated to a first DNA molecule and an antigen conjugated to a second DNA molecule to the sample, wherein the antigen binds to the target antibody isotype in the sample, if present, and the antibody-binding agent specifically binds to the target antibody isotype resulting in formation of a complex; b) contacting the complex with a bridge oligonucleotide, wherein the bridge oligonucleotide comprises a first portion sufficiently complementary to and capable of hybridizing with the first DNA molecule, and a second portion sufficiently complementary to and capable of hybridizing with the second DNA molecule, wherein the first DNA molecule and the second DNA molecule are in sufficient proximity to each other in the complex to simultaneously hybridize to the bridge oligonucleotide; c) ligating the first DNA molecule to the second DNA molecule in the complex; and d) detecting the ligation product as an indication of the presence of the target antibody isotype in the sample.

In another embodiment, the invention includes a method of detecting a target antibody isotype in a sample, the method comprising: a) adding an antibody-binding agent conjugated to a first DNA molecule and an antigen conjugated to a second DNA molecule to the sample, wherein the antigen binds to the target antibody isotype in the sample, if present, and the antibody-binding agent specifically binds to the target antibody isotype resulting in formation of a complex, and wherein a portion of the first DNA molecule is sufficiently complementary to hybridize with a portion of the second DNA molecule; b) extending the hybridized first and second DNA molecules with a DNA polymerase to produce an extended DNA product; and d) detecting the extended DNA product as an indication of the presence of the target antibody isotype in the sample.

Exemplary DNA sequences for antigen-DNA conjugates and antibody-binding agent-DNA conjugates, bridge oligonucleotides, and PCR primers for detection of the DNA ligation products are shown in Example 1 and SEQ ID NOS:1-21 of the Sequence Listing.

In certain embodiments, an antigen-DNA conjugate comprises a DNA sequence selected from the group consisting of SEQ ID NOS:1, 2, 5, 6, 9, 10, 13, 14, 17, an 18 or a DNA sequence having at least 95% identity to a DNA sequence selected from the group consisting of SEQ ID NOS:1, 2, 5, 6, 9, 10, 13, 14, 17, an 18.

In certain embodiments, an antibody-binding agent-DNA conjugate comprises a DNA sequence selected from the group consisting of SEQ ID NOS:1, 2, 5, 6, 9, 10, 13, 14, 17, an 18 or a DNA sequence having at least 95% identity to a DNA sequence selected from the group consisting of SEQ ID NOS:1, 2, 5, 6, 9, 10, 13, 14, 17, an 18.

In certain embodiments, the bridge oligonucleotide comprises the nucleotide sequence of SEQ ID NO:21 or a nucleotide sequence having at least 95% identity to the sequence of SEQ ID NO:21, wherein the bridge oligonucleotide is capable of hybridizing to the DNA of the secondary antibody-binding agent-DNA conjugate and the DNA of the antigen-DNA conjugate.

In another embodiment, the method is performed with at least one set of reagents selected from the group consisting of: a) an antigen-DNA conjugate comprising the DNA sequence of SEQ ID NO:1, an antibody-binding agent-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an antigen-DNA conjugate comprising the DNA sequence of SEQ ID NO:5, an antibody-binding agent-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an antigen-DNA conjugate comprising the DNA sequence of SEQ ID NO:9, an antibody-binding agent-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an antigen-DNA conjugate comprising the DNA sequence of SEQ ID NO:13, an antibody-binding agent-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an antigen-DNA conjugate comprising the DNA sequence of SEQ ID NO:17, an antibody-binding agent-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an antibody-binding agent-DNA conjugate comprising the DNA sequence of SEQ ID NO:1, an antigen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an antibody-binding agent-DNA conjugate comprising the DNA sequence of SEQ ID NO:5, an antigen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an antibody-binding agent-DNA conjugate comprising the DNA sequence of SEQ ID NO:9, an antigen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an antibody-binding agent-DNA conjugate comprising the DNA sequence of SEQ ID NO:13, an antigen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an antibody-binding agent-DNA conjugate comprising the DNA sequence of SEQ ID NO:17, an antigen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, the invention includes a composition for detecting antibodies in a biological sample comprising at least one set of reagents selected from the group consisting of: a) an antigen-DNA conjugate comprising the DNA sequence of SEQ ID NO:1, an antibody-binding agent-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an antigen-DNA conjugate comprising the DNA sequence of SEQ ID NO:5, an antibody-binding agent-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an antigen-DNA conjugate comprising the DNA sequence of SEQ ID NO:9, an antibody-binding agent-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an antigen-DNA conjugate comprising the DNA sequence of SEQ ID NO:13, an antibody-binding agent-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an antigen-DNA conjugate comprising the DNA sequence of SEQ ID NO:17, an antibody-binding agent-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an antibody-binding agent-DNA conjugate comprising the DNA sequence of SEQ ID NO:1, an antigen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an antibody-binding agent-DNA conjugate comprising the DNA sequence of SEQ ID NO:5, an antigen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an antibody-binding agent-DNA conjugate comprising the DNA sequence of SEQ ID NO:9, an antigen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an antibody-binding agent-DNA conjugate comprising the DNA sequence of SEQ ID NO:13, an antigen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an antibody-binding agent-DNA conjugate comprising the DNA sequence of SEQ ID NO:17, an antigen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, the invention includes a kit for performing isotype-specific agglutination-polymerase chain reaction (ISAP) comprising at least one antigen-DNA conjugate, at least one antibody-binding agent-DNA conjugate (e.g., secondary antibody or aptamer specific for an antibody isotype), at least one bridge oligonucleotide, and at least one pair of PCR primers for detecting antibodies. The kit may further comprise instructions for performing ISAP to detect antibodies. The kit may further comprise a ligase, polymerase, and/or reagents for performing PCR.

ISAP can be combined with other methods of antibody detection, particularly other methods that utilize DNA barcoding to allow detection of multiple antibody isotypes by multiplex PCR. In one multiplex assay format, ISAP is combined with proximity ligation assay (PLA) and/or agglutination-polymerase chain reaction (ADAP).

In certain embodiments, the invention includes a method for detecting allergen antibodies in a sample, the method comprising performing isotype-specific agglutination-polymerase chain reaction (ISAP) using at least one allergen-DNA conjugate in combination with at least one anti-IgE antibody-DNA conjugate to detect allergen-specific IgE levels in the sample.

In another embodiment, the invention further comprises performing ISAP with at least one allergen-DNA conjugate in combination with at least one anti-immunoglobulin G4 (IgG4) antibody-DNA conjugate to detect allergen-specific IgG4 levels.

In another embodiment, the invention further comprises performing a proximity ligation assay (PLA) using at least one pair of anti-IgE antibody-DNA conjugates to detect total immunoglobulin E (IgE) levels in the sample.

In another embodiment, the invention further comprises performing agglutination-polymerase chain reaction (ADAP) using at least one pair of allergen-DNA conjugates to detect total anti-allergen antibody levels in the sample.

In another embodiment, the invention includes a method for detecting allergen antibodies in a sample, the method comprising: a) performing a proximity ligation assay (PLA) using at least one pair of anti-IgE antibody-DNA conjugates to detect total immunoglobulin E (IgE) levels in the sample; b) performing agglutination-polymerase chain reaction (ADAP) using at least one pair of allergen-DNA conjugates to detect total anti-allergen antibody levels in the sample; and c) performing isotype-specific agglutination-polymerase chain reaction (ISAP) using at least one allergen-DNA conjugate in combination with at least one anti-IgE antibody-DNA conjugate to detect allergen-specific IgE levels in the sample. The method may further comprise performing ISAP with at least one allergen-DNA conjugate in combination with at least one anti-immunoglobulin G4 (IgG4) antibody-DNA conjugate to detect allergen-specific IgG4 levels.

In certain embodiments, ADAP is used to detect the total anti-allergen antibody levels of IgG, IgM, IgE, IgA, and IgD.

In certain embodiments, total anti-allergen levels of an IgG of subtype IgG1, IgG2, IgG3, or IgG4 subtype, or a combination thereof are detected.

In another embodiment, performing PLA comprises: a) adding said at least one pair of anti-IgE antibody-DNA conjugates to the sample, wherein said at least one pair of anti-IgE antibody-DNA conjugates comprises a first anti-IgE antibody-DNA conjugate that binds to an IgE in the sample at a first site and a second anti-IgE antibody-DNA conjugate that binds to the same IgE at a second site; b) contacting the sample with a PLA bridge oligonucleotide, wherein the PLA bridge oligonucleotide comprises: (i) a first portion sufficiently complementary to and capable of hybridizing with the DNA of the first anti-IgE antibody-DNA conjugate, and (ii) a second portion sufficiently complementary to and capable of hybridizing with the DNA of the second anti-IgE antibody-DNA conjugate, wherein the DNA of the first anti-IgE antibody-DNA conjugate and the DNA of the second anti-IgE antibody-DNA conjugate are in sufficient proximity to each other to simultaneously hybridize to the PLA bridge oligonucleotide; c) ligating the first anti-IgE antibody-DNA conjugate and the second anti-IgE antibody-DNA conjugate to produce a PLA ligation product; and d) detecting the PLA ligation product as an indication of the presence of the IgE in the sample.

In another embodiment, performing ADAP comprises: a) adding said at least one pair of allergen-DNA conjugates to the sample, wherein said at least one pair of allergen-DNA conjugates comprises a first allergen-DNA conjugate that binds to an anti-allergen antibody in the sample at a first site and a second allergen-DNA conjugate that binds to the same anti-allergen antibody at a second site; b) contacting the sample with an ADAP bridge oligonucleotide, wherein the ADAP bridge oligonucleotide comprises: (i) a first portion sufficiently complementary to and capable of hybridizing with the DNA of the first allergen-DNA conjugate, and (ii) a second portion sufficiently complementary to and capable of hybridizing with the DNA of the second allergen-DNA conjugate, wherein the DNA of the first allergen-DNA conjugate and the DNA of the second allergen-DNA conjugate are in sufficient proximity to each other to simultaneously hybridize to the ADAP bridge oligonucleotide; c) ligating the first allergen-DNA conjugate and the second allergen-DNA conjugate to produce an ADAP ligation product; and d) detecting the ADAP ligation product as an indication of the presence of the anti-allergen antibody in the sample.

In another embodiment, performing ISAP comprises: a) adding at least one allergen-DNA conjugate in combination with at least one anti-IgE antibody-DNA conjugate to the sample, wherein the allergen-DNA conjugate binds to the allergen-specific IgE in the sample, and the anti-IgE antibody-DNA conjugate binds to the same allergen-specific IgE resulting in formation of a first complex; b) contacting the first complex with an ISAP bridge oligonucleotide, wherein the ISAP bridge oligonucleotide comprises: (i) a first portion sufficiently complementary to and capable of hybridizing with the DNA of the anti-IgE antibody-DNA conjugate, and (ii) a second portion sufficiently complementary to and capable of hybridizing with the DNA of the allergen-DNA conjugate, wherein the DNA of the anti-IgE antibody-DNA conjugate and the DNA of the allergen-DNA conjugate are in sufficient proximity to each other in the first complex to simultaneously hybridize to the ISAP bridge oligonucleotide; c) ligating the anti-IgE antibody-DNA and the allergen-DNA in the first complex to produce a first ISAP ligation product; d) detecting the first ISAP ligation product as an indication of the presence of the allergen-specific IgE in the sample; e) adding at least one allergen-DNA conjugate in combination with at least one anti-IgG4 antibody-DNA conjugate to the sample, wherein the allergen-DNA conjugate binds to the allergen-specific IgG4 in the sample, and the anti-IgG4 antibody-DNA conjugate binds to the same allergen-specific IgG4 resulting in formation of a second complex; f) contacting the second complex with an ISAP bridge oligonucleotide, wherein the ISAP bridge oligonucleotide comprises: (i) a first portion sufficiently complementary to and capable of hybridizing with the DNA of the anti-IgG4 antibody-DNA conjugate, and (ii) a second portion sufficiently complementary to and capable of hybridizing with the DNA of the allergen-DNA conjugate, wherein the DNA of the anti-IgG4 antibody-DNA conjugate and the DNA of the allergen-DNA conjugate are in sufficient proximity to each other in the complex to simultaneously hybridize to the ISAP bridge oligonucleotide; g) ligating the anti-IgG4 antibody-DNA and the allergen-DNA in the second complex to produce a second ISAP ligation product; and h) detecting the second ISAP ligation product as an indication of the presence of the allergen-specific IgG4 in the sample.

In certain embodiments, detecting the PLA ligation product, the ADAP ligation product, the first ISAP ligation product, and the second ISAP ligation product is performed using multiplex polymerase chain reaction (PCR), isothermal amplification, or microarray analysis. The method may further comprise quantitating the amount of the PLA ligation product, the ADAP ligation product, the first ISAP ligation product, and the second ISAP ligation product, for example, by performing qPCR.

In another embodiment, PLA is performed with at least one set of reagents selected from the group consisting of: a) a first anti-IgE antibody-DNA conjugate comprising the DNA sequence of SEQ ID NO:1, a second anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) a first anti-IgE antibody-DNA conjugate comprising the DNA sequence of SEQ ID NO:5, a second anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) a first anti-IgE antibody-DNA conjugate comprising the DNA sequence of SEQ ID NO:9, a second anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) a first anti-IgE antibody-DNA conjugate comprising the DNA sequence of SEQ ID NO:13, a second anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) a first anti-IgE antibody-DNA conjugate comprising the DNA sequence of SEQ ID NO:17, a second anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) a second anti-IgE antibody-DNA conjugate comprising the DNA sequence of SEQ ID NO:1, a first anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) a second anti-IgE antibody-DNA conjugate comprising the DNA sequence of SEQ ID NO:5, a first anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) a second anti-IgE antibody-DNA conjugate comprising the DNA sequence of SEQ ID NO:9, a first anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) a second anti-IgE antibody-DNA conjugate comprising the DNA sequence of SEQ ID NO:13, a first anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) a second anti-IgE antibody-DNA conjugate comprising the DNA sequence of SEQ ID NO:17, a first anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ADAP is performed with at least one set of reagents selected from the group consisting of: a) a first allergen-DNA conjugate comprising the DNA sequence of SEQ ID NO:1, a second allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) a first allergen-DNA conjugate comprising the DNA sequence of SEQ ID NO:5, a second allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) a first allergen-DNA conjugate comprising the DNA sequence of SEQ ID NO:9, a second allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) a first allergen-DNA conjugate comprising the DNA sequence of SEQ ID NO:13, a second allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) a first allergen-DNA conjugate comprising the DNA sequence of SEQ ID NO:17, a second allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) a second allergen-DNA conjugate comprising the DNA sequence of SEQ ID NO:1, a first allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) a second allergen-DNA conjugate comprising the DNA sequence of SEQ ID NO:5, a first allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) a second allergen-DNA conjugate comprising the DNA sequence of SEQ ID NO:9, a first allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) a second allergen-DNA conjugate comprising the DNA sequence of SEQ ID NO:13, a first allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) a second allergen-DNA conjugate comprising the DNA sequence of SEQ ID NO:17, a first allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ISAP is performed with at least one set of reagents selected from the group consisting of: a) an allergen-DNA conjugate comprising the DNA sequence of SEQ ID NO:1, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an allergen-DNA conjugate comprising the DNA sequence of SEQ ID NO:5, an anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an allergen-DNA conjugate comprising the DNA sequence of SEQ ID NO:9, an anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an allergen-DNA conjugate comprising the DNA sequence of SEQ ID NO:13, an anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an allergen-DNA conjugate comprising the DNA sequence of SEQ ID NO:17, an anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an anti-IgE antibody-DNA conjugate comprising the DNA sequence of SEQ ID NO:1, an allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an anti-IgE antibody-DNA conjugate comprising the DNA sequence of SEQ ID NO:5, an allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an anti-IgE antibody-DNA conjugate comprising the DNA sequence of SEQ ID NO:9, an allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an anti-IgE antibody-DNA conjugate comprising the DNA sequence of SEQ ID NO:13, an allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an anti-IgE antibody-DNA conjugate comprising the DNA sequence of SEQ ID NO:17, an allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ISAP is performed with at least one set of reagents selected from the group consisting of: a) an allergen-DNA conjugate comprising the DNA sequence of SEQ ID NO:1, an anti-IgG4 antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an allergen-DNA conjugate comprising the DNA sequence of SEQ ID NO:5, an anti-IgG4 antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an allergen-DNA conjugate comprising the DNA sequence of SEQ ID NO:9, an anti-IgG4 antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an allergen-DNA conjugate comprising the DNA sequence of SEQ ID NO:13, an anti-IgG4 antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an allergen-DNA conjugate comprising the DNA sequence of SEQ ID NO:17, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an anti-IgG4 antibody-DNA conjugate comprising the DNA sequence of SEQ ID NO:1, an allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an anti-IgG4 antibody-DNA conjugate comprising the DNA sequence of SEQ ID NO:5, an allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an anti-IgG4 antibody-DNA conjugate comprising the DNA sequence of SEQ ID NO:9, an allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an anti-IgG4 antibody-DNA conjugate comprising the DNA sequence of SEQ ID NO:13, an allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an anti-IgG4 antibody-DNA conjugate comprising the DNA sequence of SEQ ID NO:17, an allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, the invention includes a method for detecting peanut allergen antibodies in a sample, wherein a) PLA is performed using a pair of anti-IgE antibody-DNA conjugates to detect total IgE levels in the sample; b) ADAP is performed using a pair of Ara h1-DNA conjugates to detect total anti-Ara h1 antibody levels in the sample, a pair of Ara h2-DNA conjugates to detect total anti-Ara h2 antibody levels in the sample, and a pair of Ara h3-DNA conjugates to detect total anti-Ara h3 antibody levels in the sample; and c) ISAP is performed using an Ara h1-DNA conjugate in combination with at least one anti-IgE antibody-DNA conjugate to detect Ara h1-specific IgE levels in the sample, an Ara h2-DNA conjugate in combination with at least one anti-IgE antibody-DNA conjugate to detect Ara h2-specific IgE levels in the sample, and an Ara h3-DNA conjugate in combination with at least one anti-IgE antibody-DNA conjugate to detect Ara h3-specific IgE levels in the sample. In another embodiment, performing ISAP further comprises using an Ara h1-DNA conjugate in combination with at least one anti-IgG4 antibody-DNA conjugate to detect Ara h1-specific IgG4 levels in the sample, an Ara h2-DNA conjugate in combination with at least one anti-IgG4 antibody-DNA conjugate to detect Ara h2-specific IgG4 levels in the sample, and an Ara h3-DNA conjugate in combination with at least one anti-IgG4 antibody-DNA conjugate to detect Ara h3-specific IgG4 levels in the sample.

In another embodiment, the method comprises: a) performing PLA with a first anti-IgE antibody-DNA conjugate comprising the DNA sequence of SEQ ID NO:1, a second anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:4 to detect the total IgE levels in the sample; b) performing ADAP with i) a first Ara h1-DNA conjugate comprising the DNA sequence of SEQ ID NO:5, a second Ara h1-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7, and a forward primer comprising the sequence of SEQ ID NO:8 to detect the total anti-Ara h1 antibody levels in the sample, ii) a first Ara h2-DNA conjugate comprising the DNA sequence of SEQ ID NO:9, a second Ara h2-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11, and a forward primer comprising the sequence of SEQ ID NO:12 to detect the total anti-Ara h2 antibody levels in the sample, and iii) a first Ara h3-DNA conjugate comprising the DNA sequence of SEQ ID NO:13, a second Ara h3-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15, and a forward primer comprising the sequence of SEQ ID NO:16 to detect the total anti-Ara h3 antibody levels in the sample; and c) performing ISAP with i) an Ara h1-DNA conjugate comprising the DNA sequence of SEQ ID NO:5, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:8 to detect Ara h1-specific IgE levels in the sample, ii) an Ara h2-DNA conjugate comprising the DNA sequence of SEQ ID NO:9, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:12 to detect Ara h2-specific IgE levels in the sample, iii) an Ara h3-DNA conjugate comprising the DNA sequence of SEQ ID NO:13, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:16 to detect Ara h3-specific IgE levels in the sample, iv) an Ara h1-DNA conjugate comprising the DNA sequence of SEQ ID NO:5, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:8 to detect Ara h1-specific IgG4 levels in the sample, v) an Ara h2-DNA conjugate comprising the DNA sequence of SEQ ID NO:9, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:12 to detect Ara h2-specific IgG4 levels in the sample, and vi) an Ara h3-DNA conjugate comprising the DNA sequence of SEQ ID NO:13, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:16 to detect Ara h3-specific IgG4 levels in the sample.

In another embodiment, the invention includes a composition comprising: a) reagents for performing PLA comprising: a first anti-IgE antibody-DNA conjugate comprising the DNA sequence of SEQ ID NO:1, a second anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:4 for detecting total IgE levels; b) reagents for performing ADAP comprising: i) a first Ara h1-DNA conjugate comprising the DNA sequence of SEQ ID NO:5, a second Ara h1-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7, and a forward primer comprising the sequence of SEQ ID NO:8 for detecting total anti-Ara h1 antibody levels, ii) a first Ara h2-DNA conjugate comprising the DNA sequence of SEQ ID NO:9, a second Ara h2-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11, and a forward primer comprising the sequence of SEQ ID NO:12 for detecting total anti-Ara h2 antibody levels, and iii) a first Ara h3-DNA conjugate comprising the DNA sequence of SEQ ID NO:13, a second Ara h3-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15, and a forward primer comprising the sequence of SEQ ID NO:16 for detecting total anti-Ara h3 antibody levels; and c) reagents for performing ISAP comprising: i) an Ara h1-DNA conjugate comprising the DNA sequence of SEQ ID NO:5, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:8 for detecting Ara h1-specific IgE levels, ii) an Ara h2-DNA conjugate comprising the DNA sequence of SEQ ID NO:9, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:12 for detecting Ara h2-specific IgE levels, iii) an Ara h3-DNA conjugate comprising the DNA sequence of SEQ ID NO:13, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:16 for detecting Ara h3-specific IgE levels, iv) an Ara h1-DNA conjugate comprising the DNA sequence of SEQ ID NO:5, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:8 for detecting Ara h1-specific IgG4 levels, v) an Ara h2-DNA conjugate comprising the DNA sequence of SEQ ID NO:9, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:12 for detecting Ara h2-specific IgG4 levels in the sample, and vi) an Ara h3-DNA conjugate comprising the DNA sequence of SEQ ID NO:13, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:16 for detecting Ara h3-specific IgG4 levels.

In another embodiment, the invention includes a kit comprising a composition described herein and instructions for detecting allergen antibodies. The kit may further comprise a ligase and reagents for performing PCR.

These and other embodiments of the subject invention will readily occur to those of skill in the art in view of the disclosure herein.

BRIEF DESCRIPTION OF THE FIGURES

FIG. 5 (bottom) shows integration of PLA, ADAP and ISAP into a single assay. PCR with the indicated primer pairs enables the multiplexed detection of allergy markers. The primers 1F/1R detect total IgE, 2F/2R detect total anti-allergen antibodies, and 2F/1R or 1F/2R detect allergen-specific IgE.

FIG. 6A shows ISAP analysis of a dilution series of purified anti-OVA IgE (black square), anti-OVA IgG (dark gray square) and non-specific IgE (light gray diamond). FIG. 6B shows ISAP (black circle) and ELISA (gray square) analysis of a dilution series of purified anti-OVA IgE. The x-axis in both graphs is the molar quantity of antibodies. The y-axis represents the delta Ct value in comparison to a blank.

FIGS. 8A-8C show that the PCR-based analysis detected enhanced production of IgE starting on day 7 (FIG. 8A), sIgE on day 14 (FIG. 8B), and total anti-OVA on day 7 (FIG. 8C). FIG. 8D shows an ELISA analysis of sIgE on the same set of serum samples. Enhanced production is observed on day 14. FIG. 8E shows a correlation between PCR-based analysis for total IgE using serum and whole blood samples. Serum and whole blood sample displayed a correlation coefficient (R) of 0.86. (* represents P value smaller than 0.05)

FIG. 9A shows results from BALB, Rag knockout and Jh knockout mice that were epicutaneously sensitized with peanut oil. Measured PCR signals are normalized to day 0. Increased production of total IgE, anti-Ara h1 IgE and total anti-Ara h3 in BALB mice were observed after sensitization. FIG. 9B shows peanut-specific IgE detection by ELISA on the same set of BALB mice serum. No induction of peanut specific IgE is observed.

FIGS. 10A-10E show PCR-based analysis of plasma from peanut-allergic human patients. Plasma were baseline samples from the POISED immunotherapy trial (ClinicalTrials.gov Identifier: NCT02103270). An integrated PCR-based analysis simultaneously detected 10 allergic features: tIgE, sIgE-Ara-h1, sIgG4-Ara-h1, total anti-Ara-h1, sIgE-Ara-h2, sIgG4-Ara-h2, total anti-Ara-h2, sIgE-Ara-h3, sIgG4-Ara-h3, total anti-Ara-h3 from 1 µL of plasma in a single assay. FIG. 10A-10C show a correlation between PCR-based assay and ImmunoCAP. High correlation between our PCR-based assay and ImmunoCAP analysis was observed (FIG. 10A (R=0.64 for sIgE Ara-h1), FIG. 10B (0.92 for sIgE-Ara-h2); FIG. 10C (0.88 for sIgE Ara-h3)). FIG. 10D shows a correlation between PCR-based assay and whole-peanut extract ImmunoCAP. We summed the sIgE signal measured by PCR-based assay for Ara-h1, Ara-h2 and Ara-h3 as a proxy for reactivity towards whole peanut extract. Correlation of the summed ISAP signal versus whole peanut extract ImmunoCAP was high (R=0.82). FIG. 10E shows a comparison between our PCR-based assay and ImmunoCAP. (The sample volume and cost are based on all 10 allergic features provided by our PCR-based assay).

DETAILED DESCRIPTION OF THE INVENTION

Figure 1:
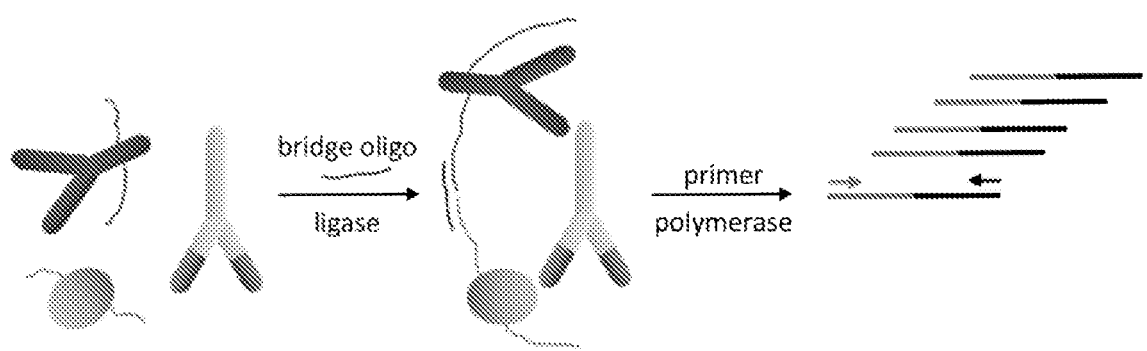
FIG. 1 shows a schematic of isotype-specific antibody detection by agglutination-PCR (ISAP).

The practice of the present invention will employ, unless otherwise indicated, conventional methods of immunology, chemistry, biochemistry, molecular biology and recombinant DNA techniques, within the skill of the art. Such techniques are explained fully in the literature. See, e.g., *IgE and Anti-IgE Therapy in Asthma and Allergic Disease* (Lung Biology in Health and Disease, R. B. Fick and P. M. Jardieu eds., CRC Press, 2002); *Middleton's Allergy: Principles and Practice* (N. F. Adkinson, B. S. Bochner, A. W. Burks, W. W. Busse, S. T. Holgate, R. F. Lemanske, and R. E. O'Hehir eds., Saunders, 8$^{th}$ edition, 2013); *PCR Technology: Current Innovations* (T. Nolan and S. A. Bustin eds., CRC Press, 3$^{rd}$ edition, 2013); *Antibodies A Laboratory Manual* (E. A. Greenfield ed., Cold Spring Harbor Laboratory Press, 2$^{nd}$ Lab edition, 2013); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); M. R. Green and J. Sambrook *Molecular Cloning: A Laboratory Manual* (Cold Spring Harbor Laboratory Press, 4$^{th}$ edition, 2012); *Methods In Enzymology* (S. Colowick and N. Kaplan eds., Academic Press, Inc.).

All publications, patents and patent applications cited herein, whether supra or infra, are hereby incorporated by reference in their entireties.

1. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "an antibody" includes a mixture of two or more antibodies, and the like.

The term "about," particularly in reference to a given quantity, is meant to encompass deviations of plus or minus five percent.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

"Substantially purified" generally refers to isolation of a substance (compound, polynucleotide, protein, polypeptide, peptide composition) such that the substance comprises the majority percent of the sample in which it resides. Typically, in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide or peptide, that the indicated molecule is separate and discrete from the whole organism with which the molecule is found in nature or is present in the substantial absence of other biological macro molecules of the same type. The term "isolated" with respect to a nucleic acid is a nucleic acid molecule devoid, in whole or part, of sequences normally associated with it in nature; or a sequence, as it exists in nature, but having heterologous sequences in association therewith; or a molecule disassociated from the chromosome.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands (or sense and anti-sense strands).

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, nucleic acids are amplified using at least one set of oligonucleotide primers comprising at least one forward primer and at least one reverse primer capable of hybridizing to regions of a nucleic acid flanking the portion of the nucleic acid to be amplified.

The term "amplicon" refers to the amplified nucleic acid product of a PCR reaction or other nucleic acid amplification process (e.g., isothermal amplification, rolling circle amplification, ligase chain reaction (LCR)).

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used in a nucleic acid amplification assay.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "selectively detects" or "selectively detecting" refer to the detection of an antibody isotype using oligonucleotides, e.g., primers and/or probes that are capable of detecting a particular DNA barcode, for example, by amplifying and/or binding to a DNA barcode of a particular antigen-DNA or antibody-binding agent-DNA conjugate (e.g., secondary antibody-DNA, antibody mimetic-DNA, or aptamer-DNA conjugate), or ligation product or extension product thereof, but do not amplify and/or bind to other DNA sequences under appropriate hybridization conditions.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303; Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

The term "antigen" as used herein refers to any naturally occurring or synthetic immunogenic substance. Immunogenic substances include those that are foreign and those that are naturally occurring within the body of an organism. As such, the introduction of a foreign immunogenic substance may induce an organism to generate a general or specific immune response to the foreign immunogenic substance. In other instances, the production of an immunogenic substance within the body of an organism may induce the organism to generate a specific or general autoimmune response to the native immunogenic substance. Antigens, as used herein, encompass but are not limited to chemicals, small molecules, biomolecules (e.g., nucleic acids), macromolecules, peptides, polypeptides, cell fragments, cells, unicellular organisms, multicellular organisms, fragments thereof, and combinations thereof. In some instances, antigens may be antigens for which an agent that binds the antigen is known, e.g., a polypeptide for which an antibody that binds the polypeptide is known. In some instances, antigens may be antigens for which an agent that binds the antigen is unknown, e.g., a polypeptide for which an antibody that binds the polypeptide is unknown. For example, the use of polypeptides and peptides, both naturally occurring and synthetic, as antigens to which antibodies may be raised has been described in, e.g., Methods in Molecular Biology: Immunochemical Protocols. Ed. Burns, R., Humana Press, 2005, the disclosure of which is incorporated herein by reference in its entirety.

The phrase "specifically (or selectively) binds" to an antibody or "specifically (or selectively) immunoreactive with," when referring to an antigen or allergen, refers to a binding reaction that is determinative of the presence of the antigen or allergen in a heterogeneous population of proteins and other biologics. Thus, under designated immunoassay conditions, the specified antibodies bind to a particular antigen at least two times the background and do not substantially bind in a significant amount to other antigens present in the sample. Specific binding to an antibody under such conditions may require an antibody that is selected for its specificity for a particular antigen. For example, polyclonal antibodies raised to an antigen from specific species such as rat, mouse, or human can be selected to obtain only those polyclonal antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

As used herein, a "biological sample" refers to a sample of cells, tissue, or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, cells (e.g., epithelial and endothelial cells, fibroblasts, and macrophages), muscles, joints, organs (e.g., liver, lung, spleen, thymus, kidney, brain, or lymph node), abnormal collections of fluid such as inflammatory transudates or exudates, pus, contents of cysts or areas of tissue necrosis, natural or induced sputum, fluid obtained by lavage performed for diagnostic or therapeutic purposes, such as nasal, pharyngeal or bronchoalveolar lavage, or biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-di chlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of reagents and methods for detection of antibodies of specific isotypes. In particular, antigen-DNA conjugates and antibody-binding agent-DNA conjugates carrying DNA barcodes are used to detect the presence of specific antibodies. The use of a DNA barcode allows antibodies to be identified by nucleic acid-based detection methods, such as PCR, isothermal amplification, or microarray analysis. The methods of the invention can be used to detect and/or quantitate multiple antibodies in a single assay. In addition, the assays described herein can be readily combined with any other assays for detection of antibodies. Multiplex assays can be used, for example, to detect total levels of disease-relevant antibodies as well as individual levels of multiple disease-relevant antibody isotypes. The methods of the invention will allow monitoring of disease-relevant antibodies associated with immune disorders, such as allergies, autoimmune diseases, infections, or inflammation and better disease management.

In order to further an understanding of the invention, a more detailed discussion is provided below regarding the assay methods for detecting antibodies and their use in diagnosing and monitoring disease-relevant antibodies.

A. Multiplex Assays for Detecting Antibodies

The methods use antigen-DNA conjugates and antibody-binding agent-DNA conjugates as well as oligonucleotide reagents (e.g., oligonucleotide primers and/or probes) or a combination of reagents capable of detecting one or more antibody isotypes in a single assay. The assay methods described herein can be used for detecting antibody isotypes specific for any type of antigen, including, but not limited to an allergen, an autoimmune disease antigen, a cancer antigen, or a pathogen antigen. There are a number of assay designs that can be used to detect antibody isotypes, which can be used alone or in combination with each other.

In one embodiment, the invention includes a method of detecting a target antibody isotype in a sample, the method comprising: a) contacting the sample with an antibody-binding agent conjugated to a first DNA molecule comprising a first portion of a barcode, and an antigen conjugated to a second DNA molecule comprising a second portion of a barcode, wherein the antigen binds to the target antibody isotype in the sample, if present, and the antibody-binding agent specifically binds to the target antibody isotype resulting in formation of a complex; b) connecting the first DNA molecule to the second DNA molecule in the complex, wherein the first portion of the barcode and the second portion of the barcode are joined to form a complete barcode; and c) detecting the complete barcode as an indication of the presence of the target antibody isotype in the sample.

Connecting the first DNA molecule to the second DNA molecule can be accomplished in various ways. In one embodiment, the first DNA molecule and the second DNA molecule are ligated together using a ligase to produce a ligation product comprising the complete barcode. A bridge oligonucleotide may be used to facilitate ligation, wherein the bridge oligonucleotide comprises a first portion sufficiently complementary to and capable of hybridizing with the first DNA molecule, and a second portion sufficiently complementary to and capable of hybridizing with the second DNA molecule. In the complex comprising the antibody-binding agent conjugated to the first DNA molecule and the antigen conjugated to the second DNA molecule, wherein both conjugates are bound to the target antibody isotype, the first DNA molecule and the second DNA molecule are in sufficient proximity to each other to simultaneously hybridize to the bridge oligonucleotide and undergo ligation. The ligation product can be detected and/or quantitated, for example, using polymerase chain reaction (PCR), isothermal amplification, or microarray analysis.

In another embodiment, the first DNA molecule and the second DNA molecule comprise complementary nucleotide sequences, wherein hybridization of a nucleotide sequence in the first DNA molecule to a complementary nucleotide sequence in the second DNA molecule allows a polymerase to extend the hybridized first and second DNA molecules to produce a nucleic acid comprising the complete barcode. The polymerase reaction can be carried out, for example, under isothermal conditions.

The "antibody binding agent" can be any agent that specifically binds to a target antibody isotype. In some embodiments, the antibody binding agent binds to a target antibody isotype with high affinity. Examples of antibody binding agents include, without limitation, antibodies, antibody fragments, antibody mimetics, and aptamers.

In certain embodiments, the antibody-binding agent comprises an antibody that specifically binds to the target antibody isotype. Any type of antibody may be used, including polyclonal and monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule (i.e., specifically binds to a target antibody isotype).

In other embodiments, the antibody-binding agent comprises an aptamer that specifically binds to the target antibody isotype. Any type of aptamer may be used, including a DNA, RNA, xeno-nucleic acid (XNA), or peptide aptamer that specifically binds to the target antibody isotype. Such aptamers can be identified, for example, by screening a combinatorial library. Nucleic acid aptamers (e.g., DNA or RNA aptamers) that bind selectively to a target antibody isotype can be produced by carrying out repeated rounds of in vitro selection or systematic evolution of ligands by exponential enrichment (SELEX). Peptide aptamers that bind to a target antibody isotype may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Nucleic Acid Aptamers: Selection, Characterization, and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol Biol. 118:217-231; Platella et al. (2016) Biochim. Biophys. Acta Nov 16 pii: S0304-4165(16)30447-0, and Lyu et al. (2016) Theranostics 6(9):1440-1452; herein incorporated by reference in their entireties.

In yet other embodiment, the antibody-binding agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15): 6553-6560), affitins (Krehenbrink et al. (2008) J. Mol. Biol. 383 (5):1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

Antigen-DNA and antibody-binding agent-DNA conjugates of the subject methods include at least one DNA molecule attached to the antigen or antibody-binding agent, respectively, wherein the DNA molecule comprises a unique barcode sequence that identifies a target antigen-specific antibody isotype (i.e., the complete barcode produced by joining the DNA sequences of the antigen-DNA and antibody-binding agent-DNA conjugates). DNA molecules attached to an antigen or antibody-binding agent may vary depending, in part, on the detection method employed, the method of attachment, the specific antibodies to be detected, etc. Generally, the length of the attached DNA molecules will be at least 15 nucleotides, but may range from 15 nucleotides to 200 nucleotides or more including but not limited to e.g., 20 or more nucleotides, 25 or more nucleotides, 30 or more nucleotides, 35 or more nucleotides, 40 or more nucleotides, 45 or more nucleotides, 50 or more nucleotides, 55 or more nucleotides, 60 or more nucleotides, 65 or more nucleotides, 70 or more nucleotides, 75 or more nucleotides, 80 or more nucleotides, 90 or more nucleotides, 95 or more nucleotides, 100 or more nucleotides, 15 to 200 nucleotides, 20 to 200 nucleotides, 25 to 200 nucleotides, 30 to 200 nucleotides, 35 to 200 nucleotides, 40 to 200 nucleotides, 45 to 200 nucleotides, 50 to 200 nucleotides, 15 to 100 nucleotides, 20 to 100 nucleotides, 25 to 100 nucleotides, 30 to 100 nucleotides, 35 to 100 nucleotides, 40 to 100 nucleotides, 45 to 100 nucleotides, 50 to 100 nucleotides, etc.

The DNA may be attached to an antigen or antibody-binding agent by any convenient method, as described in more detail below. The DNA may be attached to an antigen or antibody-binding agent at any convenient point along the length of the DNA, including at the 3' or 5' termini. In some instances, DNA is attached to the antigen or antibody at its 3' end or 5' end. In some instances, both the antigen and the antibody-binding agent have DNA molecules attached at their 3' ends. In some instances, both the antigen and the antibody-binding agent have DNA molecules attached at their 5' ends.

As used herein, the term "bridging oligonucleotide" or "bridge oligonucleotide" refers to any oligonucleotide that joins two or more separate DNA molecules or two termini of a single DNA molecule by simultaneously hybridizing with complementary regions on each DNA molecule or complementary regions of the DNA termini. In certain instances, a bridging oligonucleotide joins an antigen-DNA conjugate to an antibody-binding agent-DNA conjugate by simultaneously hybridizing with a first complementary region in the DNA of the antigen-DNA conjugate and a second complementary region in the DNA of the antibody-binding agent- DNA conjugate. Bridging oligonucleotides may be partially or completely single stranded, including partially single stranded and partially double stranded. The length of bridging oligonucleotides of the subject disclosure will vary and may be 10 or more nucleotides and range from 10 to 100 or more nucleotides, including e.g., 10 to 100 nucleotides, 12 to 100 nucleotides, 14 to 100 nucleotides, 16 to 100 nucleotides, 18 to 100 nucleotides, 20 to 100 nucleotides, 22 to 100 nucleotides, 24 to 100 nucleotides, 26 to 100 nucleotides, 28 to 100 nucleotides, 30 to 100 nucleotides, 10 to 50 nucleotides, 12 to 50 nucleotides, 14 to 50 nucleotides, 16 to 50 nucleotides, 18 to 50 nucleotides, 20 to 50 nucleotides, 22 to 50 nucleotides, 24 to 50 nucleotides, 26 to 50 nucleotides, 28 to 50 nucleotides, 30 to 50 nucleotides, 10 to 40 nucleotides, 12 to 40 nucleotides, 14 to 40 nucleotides, 16 to 40 nucleotides, 18 to 40 nucleotides, 20 to 40 nucleotides, 22 to 40 nucleotides, 24 to 40 nucleotides, 26 to 40 nucleotides, 28 to 40 nucleotides, 30 to 40 nucleotides, 10 to 30 nucleotides, 12 to 30 nucleotides, 14 to 30 nucleotides, 16 to 30 nucleotides, 18 to 30 nucleotides, 20 to 30 nucleotides, 12 or more nucleotides, 13 or more nucleotides, 14 or more nucleotides, 15 or more nucleotides, 16 or more nucleotides, 17 or more nucleotides, 18 or more nucleotides, 19 or more nucleotides, 20 or more nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, etc.

Bridging oligonucleotides may "bridge" two or more DNA molecules to form a complex. In some instances, a bridging polynucleotide may hybridize with two DNA termini, including termini of the same or different nucleic acids, such that the termini are adjacent within the complex, e.g., allowing for the ligation of the adjacent termini. In some instances, a bridging polynucleotide may hybridize with two DNA termini, including termini of the same or different nucleic acids, such that the termini are not adjacent in the resulting polynucleotide complex, e.g., are not adjacent such that they cannot be directly ligated together. In some instances, e.g., where two DNA termini in a complex are not adjacent, a splint polynucleotide may be hybridized in the space between the two termini such that the ends of the splint polynucleotide are located adjacent to one or more of the termini. The term "splint polynucleotide" as used herein refers to a polynucleotide, which may generally be single stranded or partially single stranded and partially double stranded, which may be used to fill one or more gaps between two DNA termini in a complex, e.g., those complexes formed by use of a bridging polynucleotide. In some instances, a splint polynucleotide may have complementarity to one or more portions of a bridging oligonucleotide. In some instances, DNA termini adjacent to a splint polynucleotide may be ligated to the splint polynucleotide.

In some instances, a bridging oligonucleotide of the subject disclosure may include one or more nucleoside analogs. For example, in some instances, a bridging oligonucleotide of the instant disclosure may include one or more deoxyribouracil (i.e., deoxyribose uracil, deoxyuridine, etc.) nucleosides/nucleotides. In certain instances, a bridging polynucleotide may include 2 or more nucleoside analogs including but not limited to e.g., 3 or more, 4 or more, 5 or more, 6 or more, etc. In some instances, the number of nucleoside analogs as a percentage of the total bases of the bridging polynucleotide is 1% or more, including but not limited to e.g., 2% or more, 3% or more, 4% or more, 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, etc.

Joining of DNA molecules from an antigen-DNA conjugate and an antibody-binding agent-DNA conjugate produces a complete barcode sequence identifying the target antibody isotype, which may be amplified to generate an amplification product (i.e., amplicon) that can be detected. Any convenient method of amplification may be utilized in generating the amplification product, as described in more detail below, and may depend upon the particular complex formed and/or particular requirements of the overall detection assay. As the formation of an amplicon is dependent on a target antibody in a sample binding to the antigen-DNA conjugate and the antibody-binding agent-DNA conjugate binding to the same target antibody, the presence of an amplification product is indicative of the presence of target antibodies in the sample that are specific for the antigen and also recognized by the antibody-binding agent (e.g., a secondary antibody, antibody mimetic, or aptamer specific for a particular target antibody isotype).

In some instances, amplification may be performed by polymerase chain reaction (PCR). In representative PCR amplification reactions, the reaction mixture generally includes a template nucleic acid which is combined with one or more primers that are employed in the primer extension reaction, e.g., the PCR primers (such as forward and reverse primers employed in geometric (or exponential) amplification or a single primer employed in a linear amplification). As such, in some instances, the hybridized portions of the above described nucleic acid complexes may serve as "primer" for the amplification reaction. For example, in instances where linear amplification is employed a single free 3'-terminus of hybridized nucleic acid of an above described nucleic acid complex may serve as a primer for amplification. In some instances, one or more additional nucleic acids may be added to serve as primer in a formed nucleic acid complex. For example, in some instances two antigen-bound polynucleotides may be joined in a ligation reaction and two additional primers may be added to facilitate amplification of the newly ligated nucleic acid segment or template. In some instances, a single free 3'-terminus of hybridized nucleic acid of an above described nucleic acid complex may serve as a first primer and a second primer may be added to facilitate amplification.

Any oligonucleotide primers with which the template nucleic acid (hereinafter referred to as template DNA for convenience) is contacted will be of sufficient length to provide for hybridization to complementary template DNA under annealing conditions. The primers will generally be at least 6 bp in length, including but not limited to e.g., at least 10 bp in length, at least 15 bp in length, at least 16 bp in length, at least 17 bp in length, at least 18 bp in length, at least 19 bp in length, at least 20 bp in length, at least 21 bp in length, at least 22 bp in length, at least 23 bp in length, at least 24 bp in length, at least 25 bp in length, at least 26 bp in length, at least 27 bp in length, at least 28 bp in length, at least 29 bp in length, at least 30 bp in length, and may be as long as 60 bp in length or longer, where the length of the primers will generally range from 18 to 50 bp in length, including but not limited to, e.g., from about 20 to 35 bp in length. In some instances, the template DNA may be contacted with a single primer or a set of two primers (forward and reverse primers), depending on whether primer extension, linear or exponential amplification of the template DNA is desired. Methods of PCR that may be employed in the subject methods include but are not limited to those described in U.S. Pat. Nos. 4,683,202; 4,683,195; 4,800,159; 4,965,188 and 5,512,462, the disclosures of which are herein incorporated by reference.

In addition to the above components, a PCR reaction mixture produced in the subject methods may include a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Proc. Natl. Acad. Sci USA (1994) 91:2216-2220, the disclosure of which is incorporated herein by reference in its entirety); *Thermus thermophilics* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) (e.g., as described in Perler et al., Proc. Natl. Acad. Sci. USA (1992) 89:5577, the disclosure of which is incorporated herein by reference in its entirety); *Pyrococcus* species GB-D (Deep Vent); *Pyrococcus furiosus* DNA polymerase (Pfu) (e.g., as described in Lundberg et al., Gene (1991) 108: 1-6, the disclosure of which is incorporated herein by reference in its entirety), *Pyrococcus woesei* (Pwo) and the like. Generally, the reaction mixture will include four different types of dNTPs corresponding to the four naturally occurring bases are present, i.e. dATP, dTTP, dCTP and dGTP and in some instances, may include one or more modified nucleotide dNTPs.

A PCR reaction will generally be carried out by cycling the reaction mixture between appropriate temperatures for annealing, elongation/extension, and denaturation for specific times. Such temperature and times will vary and will depend on the particular components of the reaction including, e.g., the polymerase and the primers as well as the expected length of the resulting PCR product. In some instances, e.g., where nested or two-step PCR are employed the cycling-reaction may be carried out in stages, e.g., cycling according to a first stage having a particular cycling program or using particular temperature(s) and subsequently cycling according to a second stage having a particular cycling program or using particular temperature(s).

Multistep PCR processes may or may not include that addition of one or more reagents following the initiation of amplification. For example, in some instances, amplification may be initiated by elongation with the use of a polymerase and, following an initial phase of the reaction, additional reagent(s) (e.g., one or more additional primers, additional enzymes, etc.) may be added to the reaction to facilitate a second phase of the reaction. In some instances, amplification may be initiated with a first primer or a first set of primers and, following an initial phase of the reaction, additional reagent(s) (e.g., one or more additional primers, additional enzymes, etc.) may be added to the reaction to facilitate a second phase of the reaction. In certain embodiments, the initial phase of amplification may be referred to as "preamplification".

In some instances, amplification may be carried out under isothermal conditions, e.g., by means of isothermal amplification. Methods of isothermal amplification generally make use of enzymatic means of separating DNA strands to facilitate amplification at constant temperature, such as, e.g., strand-displacing polymerase or a helicase, thus negating the need for thermocycling to denature DNA. Any convenient and appropriate means of isothermal amplification may be employed in the subject methods including but are not limited to: loop-mediated isothermal amplification (LAMP), strand displacement amplification (SDA), helicase-dependent amplification (HDA), nicking enzyme amplification reaction (NEAR), and the like. LAMP generally utilizes a plurality of primers, e.g., 4-6 primers, which may recognize a plurality of distinct regions, e.g., 6-8 distinct regions, of target DNA. Synthesis is generally initiated by a strand-displacing DNA polymerase with two of the primers forming loop structures to facilitate subsequent rounds of amplification. LAMP is rapid and sensitive. In addition, the magnesium pyrophosphate produced during the LAMP amplification reaction may, in some instances be visualized without the use of specialized equipment, e.g., by eye. SDA generally involves the use of a strand-displacing DNA polymerase (e.g., Bst DNA polymerase, Large (Klenow) Fragment polymerase, Klenow Fragment (3'-5' exo-), and the like) to initiate at nicks created by a strand-limited restriction endonuclease or nicking enzyme at a site contained in a primer. In SDA, the nicking site is generally regenerated with each polymerase displacement step, resulting in exponential amplification. HDA generally employs: a helicase which unwinds double-stranded DNA unwinding to separate strands; primers, e.g., two primers, that may anneal to the unwound DNA; and a strand-displacing DNA polymerase for extension. NEAR generally involves a strand-displacing DNA polymerase that initiates elongation at nicks, e.g., created by a nicking enzyme. NEAR is rapid and sensitive, quickly producing many short nucleic acids from a target sequence.

In some instances, entire amplification methods may be combined or aspects of various amplification methods may be recombined to generate a hybrid amplification method. For example, in some instances, aspects of PCR may be used, e.g., to generate the initial template or amplicon or first round or rounds of amplification, and an isothermal amplification method may be subsequently employed for further amplification. In some instances, an isothermal amplification method or aspects of an isothermal amplification method may be employed, followed by PCR for further amplification of the product of the isothermal amplification reaction. In some instances, a sample may be preamplified using a first method of amplification and may be further processed, including e.g., further amplified or analyzed, using a second method of amplification. As a non-limiting example, a sample may be preamplified by PCR and further analyzed by qPCR.

In some instances, the amplification step and the detection step, described below, may be combined, with or without the use of a preamplifcation step. In some instances, the particular amplification method employed allows for the qualitative detection of amplification product, e.g., by visual inspection of the amplification reaction with or without a detection reagent. In one embodiment, the ligation products are amplified by isothermal amplification, e.g., LAMP, and the amplification generates a visual change in the amplification reaction indicative of efficient amplification and thus presence of the antibody isotype in the sample. In some instances, the amplification and detection steps are combined by monitoring the amplification reaction during amplification such as is performed in, e.g., real-time PCR, also referred to herein as quantitative PCR (qPCR).

In some instances, the methods described herein may make use of those methods, e.g., amplification methods, and components thereof, employed in proximity ligation assays (PLA) and proximity elongation assays (PEA) including but not limited to, e.g., rolling circle amplification (RCA), binding-induced DNA assembly (BINDA), nicking enzyme assisted fluorescence signal amplification (NEFSA), and, e.g., those described in Janssen et al. (2013) Sensors, 13, 1353-1384, the disclosure of which is incorporated herein by reference in its entirety.

The methods of the invention can be adapted to multiplexing. For example, a plurality of antibody-binding agent-DNA conjugates can be added to a sample, wherein each antibody-binding agent is conjugated to a DNA molecule comprising a different barcode sequence and each antibody-binding agent is capable of binding to a different target antibody isotype to allow multiplex detection of a plurality of target antibody isotypes in a sample. In certain embodiments, the antibody-binding agent-DNA conjugates are selected from the group consisting of an anti-IgE secondary antibody-DNA conjugate for detection of IgE, an anti-IgM secondary antibody-DNA conjugate for detection of IgM, an anti-IgG secondary antibody-DNA conjugate for detection of IgG, an anti-IgA secondary antibody-DNA conjugate for detection of IgA, and an anti-IgD secondary antibody DNA conjugate for detection of IgD, wherein the DNA molecules in the conjugates comprise isotype-specific DNA barcodes that can be amplified and detected simultaneously by using a suitable combination of primers and/or probes in a multiplex-type assay format.

Exemplary DNA sequences for antigen-DNA conjugates and antibody-binding agent-DNA conjugates, bridge oligonucleotides, and PCR primers for detection of the DNA ligation products are shown in Example 1 and SEQ ID NOS:1-21 of the Sequence Listing. In certain embodiments, an antigen-DNA conjugate comprises a DNA sequence selected from the group consisting of SEQ ID NOS:1, 2, 5, 6, 9, 10, 13, 14, 17, an 18 or a DNA sequence having at least 95% identity to a DNA sequence selected from the group consisting of SEQ ID NOS:1, 2, 5, 6, 9, 10, 13, 14, 17, an 18. In other embodiments, a secondary antibody-binding agent-DNA conjugate comprises a DNA sequence selected from the group consisting of SEQ ID NOS:1, 2, 5, 6, 9, 10, 13, 14, 17, an 18 or a DNA sequence having at least 95% identity to a DNA sequence selected from the group consisting of SEQ ID NOS:1, 2, 5, 6, 9, 10, 13, 14, 17, an 18. In certain embodiments, the bridge oligonucleotide comprises the nucleotide sequence of SEQ ID NO:21 or a nucleotide sequence having at least 95% identity to the sequence of SEQ ID NO:21, wherein the bridge oligonucleotide is capable of hybridizing to the DNA of the In another embodiment, the method is performed with at least one set of reagents selected from the group consisting of: a) an antigen-DNA conjugate comprising the DNA sequence of SEQ ID NO:1, an antibody-binding agent-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an antigen-DNA conjugate comprising the DNA sequence of SEQ ID NO:5, an antibody-binding agent-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an antigen-DNA conjugate comprising the DNA sequence of SEQ ID NO:9, an antibody-binding agent-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an antigen-DNA conjugate comprising the DNA sequence of SEQ ID NO:13, an antibody-binding agent-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an antigen-DNA conjugate comprising the DNA sequence of SEQ ID NO:17, an antibody-binding agent-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an antibody-binding agent-DNA conjugate comprising the DNA sequence of SEQ ID NO:1, an antigen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an antibody-binding agent-DNA conjugate comprising the DNA sequence of SEQ ID NO:5, an antigen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an antibody-binding agent-DNA conjugate comprising the DNA sequence of SEQ ID NO:9, an antigen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an antibody-binding agent-DNA conjugate comprising the DNA sequence of SEQ ID NO:13, an antigen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an antibody-binding agent-DNA conjugate comprising the DNA sequence of SEQ ID NO:17, an antigen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

ISAP can be combined with other methods of antibody detection, particularly other methods that utilize DNA barcoding to allow detection of multiple antibody isotypes by multiplex PCR. In one multiplex assay format, ISAP is combined with proximity ligation assay (PLA) and/or agglutination-polymerase chain reaction (ADAP). See, e.g., Gullberg et al. (2005) Proc. Natl. Acad. Sci. U.S.A. 101 (22): 8420-9424, Gustafsdottir et al. (2005) Analytical Biochemistry 345 (1):2-9, for a description of PLA and Tsai et al. (2016) ACS Central Science. 2 (3): 139-147, International Patent Application Publication No. WO2016168711 A1 for a description of ADAP; herein incorporated by reference in their entireties.

For example, ISAP can be combined with PLA and/or ADAP for detecting allergen antibodies in a sample. In one embodiment, the method comprises: a) performing PLA using at least one pair of anti-IgE antibody-DNA conjugates to detect total IgE levels in the sample; b) performing ADAP using at least one pair of allergen-DNA conjugates to detect total anti-allergen antibody levels in the sample; and c) performing ISAP using at least one allergen-DNA conjugate in combination with at least one anti-IgE antibody-DNA conjugate to detect allergen-specific IgE levels in the sample. The method may further comprise performing ISAP with at least one allergen-DNA conjugate in combination with at least one anti-immunoglobulin G4 (IgG4) antibody-DNA conjugate to detect allergen-specific IgG4 levels. In certain embodiments, ADAP is used to detect the total anti-allergen antibody levels of IgG, IgM, and IgE.

In performing PLA, the method comprises: a) adding at least one pair of anti-IgE antibody-DNA conjugates to the sample, wherein at least one pair of anti-IgE antibody-DNA conjugates comprises a first anti-IgE antibody-DNA conjugate that binds to an IgE in the sample at a first site and a second anti-IgE antibody-DNA conjugate that binds to the same IgE at a second site; b) contacting the sample with a PLA bridge oligonucleotide, wherein the PLA bridge oligonucleotide comprises: (i) a first portion sufficiently complementary to and capable of hybridizing with the DNA of the first anti-IgE antibody-DNA conjugate, and (ii) a second portion sufficiently complementary to and capable of hybridizing with the DNA of the second anti-IgE antibody-DNA conjugate, wherein the DNA of the first anti-IgE antibody-DNA conjugate and the DNA of the second anti-IgE antibody-DNA conjugate are in sufficient proximity to each other to simultaneously hybridize to the PLA bridge oligonucleotide; c) ligating the PLA bridge oligonucleotide to the first anti-IgE antibody-DNA conjugate and the second anti-IgE antibody-DNA conjugate to produce a PLA ligation product; and d) detecting the PLA ligation product as an indication of the presence of the IgE in the sample.

In performing the ADAP, the method comprises: a) adding said at least one pair of allergen-DNA conjugates to the sample, wherein at least one pair of allergen-DNA conjugates comprises a first allergen-DNA conjugate that binds to an anti-allergen antibody in the sample at a first site and a second allergen-DNA conjugate that binds to the same anti-allergen antibody at a second site; b) contacting the sample with an ADAP bridge oligonucleotide, wherein the ADAP bridge oligonucleotide comprises: (i) a first portion sufficiently complementary to and capable of hybridizing with the DNA of the first allergen-DNA conjugate, and (ii) a second portion sufficiently complementary to and capable of hybridizing with the DNA of the second allergen-DNA conjugate, wherein the DNA of the first allergen-DNA conjugate and the DNA of the second allergen-DNA conjugate are in sufficient proximity to each other to simultaneously hybridize to the ADAP bridge oligonucleotide; c) ligating the ADAP bridge oligonucleotide to the first allergen-DNA conjugate and the second allergen-DNA conjugate to produce an ADAP ligation product; and d) detecting the ADAP ligation product as an indication of the presence of the anti-allergen antibody in the sample.

In performing the ISAP, the method comprises: a) adding the at least one allergen-DNA conjugate in combination with at least one anti-IgE antibody-DNA conjugate to the sample, wherein the allergen-DNA conjugate binds to the allergen-specific IgE in the sample, and the anti-IgE antibody-DNA conjugate binds to the same allergen-specific IgE resulting in formation of a first complex; b) contacting the first complex with an ISAP bridge oligonucleotide, wherein the ISAP bridge oligonucleotide comprises: (i) a first portion sufficiently complementary to and capable of hybridizing with the DNA of the anti-IgE antibody-DNA conjugate, and (ii) a second portion sufficiently complementary to and capable of hybridizing with the DNA of the allergen-DNA conjugate, wherein the DNA of the anti-IgE antibody-DNA conjugate and the DNA of the allergen-DNA conjugate are in sufficient proximity to each other in the first complex to simultaneously hybridize to the ISAP bridge oligonucleotide; c) ligating the ISAP bridge oligonucleotide to the anti-IgE antibody-DNA and the allergen-DNA in the first complex to produce a first ISAP ligation product; d) detecting the first ISAP ligation product as an indication of the presence of the allergen-specific IgE in the sample; e) adding the at least one allergen-DNA conjugate in combination with at least one anti-IgG4 antibody-DNA conjugate to the sample, wherein the allergen-DNA conjugate binds to the allergen-specific IgG4 in the sample, and the anti-IgG4 antibody-DNA conjugate binds to the same allergen-specific IgG4 resulting in formation of a second complex; f) contacting the second complex with an ISAP bridge oligonucleotide, wherein the ISAP bridge oligonucleotide comprises: (i) a first portion sufficiently complementary to and capable of hybridizing with the DNA of the anti-IgG4 antibody-DNA conjugate, and (ii) a second portion sufficiently complementary to and capable of hybridizing with the DNA of the allergen-DNA conjugate, wherein the DNA of the anti-IgG4 antibody-DNA conjugate and the DNA of the allergen-DNA conjugate are in sufficient proximity to each other in the complex to simultaneously hybridize to the ISAP bridge oligonucleotide; g) ligating the ISAP bridge oligonucleotide to the anti-IgG4 antibody-DNA and the allergen-DNA in the second complex to produce a second ISAP ligation product; and h) detecting the second ISAP ligation product as an indication of the presence of the allergen-specific IgG4 in the sample.

In certain embodiments, detecting the PLA ligation product, the ADAP ligation product, the first ISAP ligation product, and the second ISAP ligation product comprises using multiplex polymerase chain reaction (PCR), isothermal amplification, or microarray analysis. The method may further comprise quantitating the amount of the PLA ligation product, the ADAP ligation product, the first ISAP ligation product, and the second ISAP ligation product, for example, by performing qPCR.

In another embodiment, PLA is performed with at least one set of reagents selected from the group consisting of: a) a first anti-IgE antibody-DNA conjugate comprising the DNA sequence of SEQ ID NO:1, a second anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) a first anti-IgE antibody-DNA conjugate comprising the DNA sequence of SEQ ID NO:5, a second anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) a first anti-IgE antibody-DNA conjugate comprising the DNA sequence of SEQ ID NO:9, a second anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) a first anti-IgE antibody-DNA conjugate comprising the DNA sequence of SEQ ID NO:13, a second anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) a first anti-IgE antibody-DNA conjugate comprising the DNA sequence of SEQ ID NO:17, a second anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) a second anti-IgE antibody-DNA conjugate comprising the DNA sequence of SEQ ID NO:1, a first anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) a second anti-IgE antibody-DNA conjugate comprising the DNA sequence of SEQ ID NO:5, a first anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) a second anti-IgE antibody-DNA conjugate comprising the DNA sequence of SEQ ID NO:9, a first anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) a second anti-IgE antibody-DNA conjugate comprising the DNA sequence of SEQ ID NO:13, a first anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) a second anti-IgE antibody-DNA conjugate comprising the DNA sequence of SEQ ID NO:17, a first anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ADAP is performed with at least one set of reagents selected from the group consisting of: a) a first allergen-DNA conjugate comprising the DNA sequence of SEQ ID NO:1, a second allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) a first allergen-DNA conjugate comprising the DNA sequence of SEQ ID NO:5, a second allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) a first allergen-DNA conjugate comprising the DNA sequence of SEQ ID NO:9, a second allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) a first allergen-DNA conjugate comprising the DNA sequence of SEQ ID NO:13, a second allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) a first allergen-DNA conjugate comprising the DNA sequence of SEQ ID NO:17, a second allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) a second allergen-DNA conjugate comprising the DNA sequence of SEQ ID NO:1, a first allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) a second allergen-DNA conjugate comprising the DNA sequence of SEQ ID NO:5, a first allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) a second allergen-DNA conjugate comprising the DNA sequence of SEQ ID NO:9, a first allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) a second allergen-DNA conjugate comprising the DNA sequence of SEQ ID NO:13, a first allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) a second allergen-DNA conjugate comprising the DNA sequence of SEQ ID NO:17, a first allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ISAP is performed with at least one set of reagents selected from the group consisting of: a) an allergen-DNA conjugate comprising the DNA sequence of SEQ ID NO:1, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an allergen-DNA conjugate comprising the DNA sequence of SEQ ID NO:5, an anti-IgE antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an allergen-DNA conjugate comprising the DNA sequence of SEQ ID NO:9, an anti-IgE antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an allergen-DNA conjugate comprising the DNA sequence of SEQ ID NO:13, an anti-IgE antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an allergen-DNA conjugate comprising the DNA sequence of SEQ ID NO:17, an anti-IgE antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an anti-IgE antibody-DNA conjugate comprising the DNA sequence of SEQ ID NO:1, an allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an anti-IgE antibody-DNA conjugate comprising the DNA sequence of SEQ ID NO:5, an allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an anti-IgE antibody-DNA conjugate comprising the DNA sequence of SEQ ID NO:9, an allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an anti-IgE antibody-DNA conjugate comprising the DNA sequence of SEQ ID NO:13, an allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an anti-IgE antibody-DNA conjugate comprising the DNA sequence of SEQ ID NO:17, an allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, ISAP is performed with at least one set of reagents selected from the group consisting of: a) an allergen-DNA conjugate comprising the DNA sequence of SEQ ID NO:1, an anti-IgG4 antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; b) an allergen-DNA conjugate comprising the DNA sequence of SEQ ID NO:5, an anti-IgG4 antibody-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; c) an allergen-DNA conjugate comprising the DNA sequence of SEQ ID NO:9, an anti-IgG4 antibody-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; d) an allergen-DNA conjugate comprising the DNA sequence of SEQ ID NO:13, an anti-IgG4 antibody-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; e) an allergen-DNA conjugate comprising the DNA sequence of SEQ ID NO:17, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20; f) an anti-IgG4 antibody-DNA conjugate comprising the DNA sequence of SEQ ID NO:1, an allergen-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3 and a forward primer comprising the sequence of SEQ ID NO:4; g) an anti-IgG4 antibody-DNA conjugate comprising the DNA sequence of SEQ ID NO:5, an allergen-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7 and a forward primer comprising the sequence of SEQ ID NO:8; h) an anti-IgG4 antibody-DNA conjugate comprising the DNA sequence of SEQ ID NO:9, an allergen-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11 and a forward primer comprising the sequence of SEQ ID NO:12; i) an anti-IgG4 antibody-DNA conjugate comprising the DNA sequence of SEQ ID NO:13, an allergen-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15 and a forward primer comprising the sequence of SEQ ID NO:16; and j) an anti-IgG4 antibody-DNA conjugate comprising the DNA sequence of SEQ ID NO:17, an allergen-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19 and a forward primer comprising the sequence of SEQ ID NO:20.

In another embodiment, the invention includes a method for detecting peanut allergen antibodies in a sample, wherein a) PLA is performed using a pair of anti-IgE antibody-DNA conjugates to detect total IgE levels in the sample; b) ADAP is performed using a pair of Ara h1-DNA conjugates to detect total anti-Ara h1 antibody levels in the sample, a pair of Ara h2-DNA conjugates to detect total anti-Ara h2 antibody levels in the sample, and a pair of Ara h3-DNA conjugates to detect total anti-Ara h3 antibody levels in the sample; and c) ISAP is performed using an Ara h1-DNA conjugate in combination with at least one anti-IgE antibody-DNA conjugate to detect Ara h1-specific IgE levels in the sample, an Ara h2-DNA conjugate in combination with at least one anti-IgE antibody-DNA conjugate to detect Ara h2-specific IgE levels in the sample, and an Ara h3-DNA conjugate in combination with at least one anti-IgE antibody-DNA conjugate to detect Ara h3-specific IgE levels in the sample. In another embodiment, performing ISAP further comprises using an Ara h1-DNA conjugate in combination with at least one anti-IgG4 antibody-DNA conjugate to detect Ara h1-specific IgG4 levels in the sample, an Ara h2-DNA conjugate in combination with at least one anti-IgG4 antibody-DNA conjugate to detect Ara h2-specific IgG4 levels in the sample, and an Ara h3-DNA conjugate in combination with at least one anti-IgG4 antibody-DNA conjugate to detect Ara h3-specific IgG4 levels in the sample.

In another embodiment, the method comprises: a) performing PLA with a first anti-IgE antibody-DNA conjugate comprising the DNA sequence of SEQ ID NO:1, a second anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:4 to detect the total IgE levels in the sample; b) performing ADAP with i) a first Ara h1-DNA conjugate comprising the DNA sequence of SEQ ID NO:5, a second Ara h1-DNA conjugate comprising the DNA sequence of SEQ ID NO:6, a bridge oligonucleotide comprising the nucleotide sequence of SEQ ID NO:21, a reverse primer comprising the nucleotide sequence of SEQ ID NO:7, and a forward primer comprising the sequence of SEQ ID NO:8 to detect the total anti-Ara h1 antibody levels in the sample, ii) a first Ara h2-DNA conjugate comprising the DNA sequence of SEQ ID NO:9, a second Ara h2-DNA conjugate comprising the DNA sequence of SEQ ID NO:10, a bridge oligonucleotide comprising the nucleotide sequence of SEQ ID NO:21, a reverse primer comprising the nucleotide sequence of SEQ ID NO:11, and a forward primer comprising the sequence of SEQ ID NO:12 to detect the total anti-Ara h2 antibody levels in the sample, and iii) a first Ara h3-DNA conjugate comprising the DNA sequence of SEQ ID NO:13, a second Ara h3-DNA conjugate comprising the DNA sequence of SEQ ID NO:14, a bridge oligonucleotide comprising the nucleotide sequence of SEQ ID NO:21, a reverse primer comprising the nucleotide sequence of SEQ ID NO:15, and a forward primer comprising the sequence of SEQ ID NO:16 to detect the total anti-Ara h3 antibody levels in the sample; and c) performing ISAP with i) an Ara h1-DNA conjugate comprising the DNA sequence of SEQ ID NO:5, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:8 to detect Ara h1-specific IgE levels in the sample, ii) an Ara h2-DNA conjugate comprising the DNA sequence of SEQ ID NO:9, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:12 to detect Ara h2-specific IgE levels in the sample, iii) an Ara h3-DNA conjugate comprising the DNA sequence of SEQ ID NO:13, an anti-IgE antibody-DNA conjugate comprising the DNA sequence of SEQ ID NO:2, a bridge oligonucleotide comprising the nucleotide sequence of SEQ ID NO:21, a reverse primer comprising the nucleotide sequence of SEQ ID NO:3, and a forward primer comprising the sequence of SEQ ID NO:16 to detect Ara h3-specific IgE levels in the sample, iv) an Ara h1-DNA conjugate comprising the DNA sequence of SEQ ID NO:5, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:8 to detect Ara h1-specific IgG4 levels in the sample, v) an Ara h2-DNA conjugate comprising the DNA sequence of SEQ ID NO:9, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:12 to detect Ara h2-specific IgG4 levels in the sample, and vi) an Ara h3-DNA conjugate comprising the DNA sequence of SEQ ID NO:13, an anti-IgG4 antibody-DNA conjugate comprising the DNA sequence of SEQ ID NO:18, a bridge oligonucleotide comprising the nucleotide sequence of SEQ ID NO:21, a reverse primer comprising the nucleotide sequence of SEQ ID NO:19, and a forward primer comprising the sequence of SEQ ID NO:16 to detect Ara h3-specific IgG4 levels in the sample.

B. Detection

The presence of the amplification product may be determined, including qualitatively determined or quantitatively determined, by any convenient method. In some instances, the presence of the amplification product may be qualitatively determined, e.g., through a physical change in the amplification reaction that is indicative of efficient amplification of the ligation product.

In some instances, the amplification product is detected and/or the amount of amplification product is measured by a detection protocol for non-specific detection of the amplified nucleic acid or a protocol for specific detection of the amplified nucleic acid.

Representative non-specific detection protocols of interest include protocols that employ signal producing systems that selectively detect double stranded nucleic acid products, e.g., via intercalation. Representative detectable molecules that find use in such embodiments include fluorescent nucleic acid stains, such as phenanthridinium dyes, including monomers or homo- or heterodimers thereof, that provide enhanced fluorescence when complexed with nucleic acids. Examples of phenanthridinium dyes include ethidium homodimer, ethidium bromide, propidium iodide, and other alkyl-substituted phenanthridinium dyes. In another embodiment, a nucleic acid stain includes an acridine dye, or a homo- or heterodimer thereof, such as acridine orange, acridine homodimer, ethidium-acridine heterodimer, or 9-amino-6-chloro-2-methoxyacridine. In yet another embodiment, the nucleic acid stain is an indole or imidazole dye, such as Hoechst 33258, Hoechst 33342, Hoechst 34580, DAPI (4',6-diamidino-2-phenylindole) or DIPI (4', 6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating Tb3+ and Eu3+, for example). In certain embodiments, the nucleic acid stain is a cyanine dye or a homo- or heterodimer of a cyanine dye that gives an enhanced fluorescence when associated with nucleic acids. In some instances, dyes described in U.S. Pat. Nos. 4,883,867, 5,582,977, 5,321,130, and 5,410,030, which are incorporated herein by reference in their entirety, may be used, including commercially available TOTO® nucleic acid stains, BOBO™ nucleic acid stains, POPO™ nucleic acid stains, YOYO® nucleic acid stains, TO-PRO nucleic acid stains, BO-PRO nucleic acid stains, PO-PRO™ nucleic acid stains and YO-PRO® nucleic acid stains (Life Technologies, Inc. Grand Island, N.Y.). In some instances, dyes described in U.S. Pat. Nos. 5,436,134, 5,658,751 and 5,863,753, which are incorporated herein by reference in their entirety, may be used, including commercially available SYBR® nucleic acid stains, SYTO® nucleic acid stains, SYTOX® nucleic acid stains, PICOGREEN® nucleic acid stain, OLIGREEN® nucleic acid stain, and RIBOGREEN® nucleic acid stain (Life Technologies, Inc. Grand Island, N.Y.). In yet other embodiments, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives enhanced fluorescence when associated with nucleic acids, including commercially available SYTO® nucleic acid stains, SYTOX® nucleic acid stains, JOJO™ nucleic acid stains, JO-PRO™ nucleic acid stains, LOLO™ nucleic acid stains, and LO-PRO™ nucleic acid stains (Life Technologies, Inc. Grand Island, N.Y.).

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In some embodiments, the label is a directly detectable label, where directly detectable labels of interest include, but are not limited to: fluorescent labels, radioisotopic labels, chemiluminescent labels, and the like. In some embodiments, the label is a fluorescent label, where the labeling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels, such as those described above, may also be employed.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, and in certain embodiments is an increase in fluorescence. The sample may be screened for an increase in fluorescence using any convenient means, e.g., a suitable fluorimeter, such as a thermostable cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple reaction vessels, e.g., multiple tubes, multi-well plates, etc., can be assessed at the same time.

In some instances, the elongation and/or amplification of a particular DNA sequence (e.g., from an antigen-DNA conjugate, antibody-DNA conjugate, and a bridging oligonucleotide) results in the duplication of one or more specific nucleic acid sequences resulting in one or more strands containing repeats of the one or more specific nucleic acid sequences. Such repetitive sequences may be detected, e.g., through hybridization of a probe nucleic acid specific for the repeated specific sequence. In certain instances, a tagged probe nucleic acid, e.g., a fluorescently tagged probe nucleic acid, an enzymatically tagged probe nucleic acid, a radiolabel tagged probe nucleic acid, etc., specific for the repeated specific sequence may be utilized to detect an elongated polynucleotide or amplification product that contains the repeated specific sequence. In some instances, hybridization of a tagged probe nucleic acid to a repeating sequence of an elongated polynucleotide or amplification product allows for the detection of the elongated polynucleotide or amplification product due to the high number of tagged probe nucleic acids hybridized to the elongated polynucleotide or amplification product, which results in a high local concentration of detectable tag.

For example, in some instances, repeats of one or more sequences of DNA from an antigen-DNA conjugate or antibody-binding agent-DNA conjugate are contained in an amplification product or elongation product produced according to the methods described herein and the repeats are detected through the use of a tagged probe nucleic acid specific for the repeating sequence units. In some instances, repeats of one or more sequences of a bridging polynucleotide are contained in an amplification product or elongation product produced according to the methods described herein and the repeats are detected through the use of a tagged probe nucleic acid specific for the repeating sequence units. In some instances, repeats of one or more sequences of a circularizing oligonucleotide are contained in an amplification product or elongation product produced according to the methods described herein and the repeats are detected through the use of a tagged probe nucleic acid specific for the repeating sequence units.

In certain embodiments, a repeating nucleic acid sequence may be produced by one or more of the elongation and/or amplification methods described herein, e.g., PCR amplification, isothermal amplification (e.g., RCA), etc., and the elongation and/or amplification product may be made detectable through hybridization of one or more fluorescently labeled probe nucleic acid to the elongation and/or amplification product. Such detectable elongation and/or amplification product may be identified through any convenient means for detecting fluorescence, including but not limited to, e.g., fluorescent microscopy, flow cytometry, imaging flow cytometry, etc. In some instances, identification of a detectable elongation and/or amplification product may allow for detection or identification of a molecule, particle, cell, tissue, organism, etc., associated with the antibody of the complex from which the elongation and/or amplification product was derived. For example, in some instances, fluorescent probe-bound elongation and/or amplification product may remain associated with a cell that produced the antibody allowing identification of the cell, e.g., by fluorescent microscopy, and/or isolation of the cell, e.g., by fluorescent activated cell sorting (FACS).

As noted above, in some instances, amplification may be monitored in real time to provide detection and/or quantitation. Where the detection protocol is a real-time protocol, e.g., as employed in qPCR reaction protocols, data may be collected at frequent intervals, for example once every 10 ms, or more or less frequently than once every 10 ms, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of preselected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in labeled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the amplification reaction, or multiple times during the reaction, e.g., after each cycle (e.g., as is done in real-time PCR monitoring).

According to the methods described herein, the presence of an antibody isotype may be detected, e.g., as above or below a particular detection threshold, or may be measured, e.g., the actual amount or concentration of the antibody isotype in the sample may be measured when present above a particular detection threshold. The actual detection threshold for a subject antibody isotype detection reaction will vary and will depend on, e.g., the antibody isotype to be detected the particular amplification method employed, the detection method employed, and the like. In some instances, the detection threshold for the subject detection methods may range from 15 ng/ml to 1 pg/ml and may include less than 15 ng/ml, less than 14 ng/ml, less than 13 ng/ml, less than 12 ng/ml, less than 11 ng/ml, less than 10 ng/ml, less than 9 ng/ml, less than 8 ng/ml, less than 7 ng/ml, less than 6 ng/ml, less than 5 ng/ml, less than 4 ng/ml, less than 3 ng/ml, less than 2 ng/ml, less than 1 ng/ml, less than 500 pg/ml, less than 400 pg/ml, less than 300 pg/ml, less than 200 pg/ml, less than 100 pg/ml, less than 90 pg/ml, less than 80 pg/ml, less than 70 pg/ml, less than 60 pg/ml, less than 50 pg/ml, less than 40 pg/ml, less than 35 pg/ml, less than 30 pg/ml, less than 25 pg/ml, less than 20 pg/ml, less than 19 pg/ml, less than 18 pg/ml, less than 17 pg/ml, less than 16 pg/ml, less than 15 pg/ml, less than 14 pg/ml, less than 13 pg/ml, less than 12 pg/ml, less than 10 pg/ml, etc. In some instances, the detection threshold for a particular detection method described herein may be expressed in the minimum moles of an antibody isotype that may be detected in a sample and, such detection thresholds may range from 200 attomoles to 100 zeptomoles, including but not limited to e.g., 200 attomoles, 190 attomoles, 180 attomoles, 170 attomoles, 160 attomoles, 150 attomoles, 140 attomoles, 130 attomoles, 120 attomoles, 110 attomoles, 100 attomoles, 90 attomoles, 80 attomoles, 70 attomoles, 60 attomoles, 50 attomoles, 40 attomoles, 30 attomoles, 20 attomoles, 10 attomoles, 1 attomole, 900 zeptomoles, 800 zeptomoles, 700 zeptomoles, 600 zeptomoles, 500 zeptomoles, 400 zeptomoles, 350 zeptomoles, 300 zeptomoles, 250 zeptomoles, 200 zeptomoles, 190 zeptomoles, 180 zeptomoles, 170 zeptomoles, 160 zeptomoles, 150 zeptomoles, 140 zeptomoles, 130 zeptomoles, 120 zeptomoles, 110 zeptomoles, 100 zeptomoles, etc.

Following detection, which may or may not include qualitative or quantitative measurement of the amplification product, the result of the detection may be assessed to determine the likelihood that the antibody isotype is present in the sample. In making such assessments, in some instances, the subject reaction may be compared to one or more control reactions or reference values. Control reactions of the subject method include positive controls, e.g., a reaction known to contain the antibody of interest and/or known to contain a known amount of antigen of interest. Control reactions may also include negative controls, e.g., reactions known to not contain a critical reagent, e.g., the antigen, the polymerase, a critical polynucleotide, etc. Reference values to which results of a detection reaction may be compared include but are not limited to a reference measurement from any control reaction performed previously, a standard curve gathered from a control reaction, a set of measured fluorescent values from positive or negative controls, user-defined reference values, manufacturer supplied reference values, etc. In some instances, assessment of a subject reaction may include comparison to a scale, e.g., a scale of reference values, which can be used to estimate the amount of antibody present in the sample.

C. Multiplexing

According to the methods described herein, a sample is readily screened for the presence of target antibody isotypes. The methods are suitable for detection of a single target antibody isotype as well as multiplex analyses, in which two or more different target antibody isotypes are assayed in the sample. In these latter multiplex situations, the number of different sets of antigen-DNA and antibody-binding agent-DNA conjugates that may be employed typically ranges from about 2 to about 20 or higher, e.g., as up to 100 or higher, 1000 or higher, etc., including but not limited to e.g., 2 to 50, 2 to 100, 10 to 100, 50 to 100, 50 to 200, 50 to 300, 50 to 400, 50 to 500, etc. In one embodiment, a multiplexed assay may make use of various different antigens conjugated to uniquely tagged DNA molecules such that amplification of a particularly uniquely tagged DNA molecule is indicative of the presence of an antibody specific for a particular antigen. In another embodiment, a multiplexed assay may make use of various different antibody-binding agents specific for different target antibody isotypes conjugated to uniquely tagged DNA molecules such that amplification of a particularly uniquely tagged DNA molecule is indicative of the presence of an antibody isotype. Accordingly, the subject assays may make use of nucleic acid tagging and/or "barcoding" strategies to allow for the detection and/or quantification of a plurality of antibody isotypes specific for particular antigens in a sample. The number of different antigens and antibody-binding agents uniquely tagged with nucleic acid barcodes, that may be included in a multiplexed assay as described herein may vary and may be limited only by, e.g., the available length of the DNA in the antigen-DNA and antibody-binding agent-DNA conjugates for the barcodes and the physical limits of antigen or antibody concentrations that may be present in the sample.

As such, in some instances, a panel of antigen-DNA and antibody-binding agent-DNA conjugates may be screened in a single reaction and the presence or quantities of each target antibody isotype of the panel may be assessed. The detection methods described above may be utilized in parallel for the detection and measurement of amplification products in a duplexed assay. In some instances, in both multiplexed and non-multiplexed assays, nucleic acid sequencing methods may be utilized for detection and/or measurement of amplification products. For example, in some instances, quantitative sequencing may be utilized, e.g., in a multiplexed assay having produced a plurality of amplification products, to determine the relative amounts or presence of each amplification product allowing for a highly sensitive and highly multiplexed assessment of many different antibody isotypes in a single sample.

In certain embodiments, a multiplexed assay of the instant disclosure may be performed in a pooled reaction to form a plurality of amplicons and the formed amplicons may be subsequently quantified to provide the quantity of the individual antibody isotypes of the multiplexed assay. For example, in one embodiment, a plurality of different antigen-DNA and antibody-binding agent-DNA conjugates may be added to a sample containing or suspected to contain one or more target antibody isotypes. Thus, upon complex formation and joining of the DNA molecules from the antigen-DNA and/or antibody-binding agent-DNA conjugates (optionally, though the use of ligation in the presence of a bridging oligonucleotide or polymerase catalyzed extension of complementary regions), amplicons are formed comprising a complete barcode corresponding to the target antibody isotypes present in the sample. Accordingly, the relative amounts of each amplicon formed will correspond to the relative amounts of each target antibody isotype in the sample. Thus, each antibody isotype may be quantified through quantification of the formed amplicons.

Quantification of the formed amplicons may be performed by any convenient method where the particular method utilized may depend in part on the number of different antibody isotypes to be detected, the sensitivity of detection desired, the sensitivity of quantification desired, the dynamic range of quantification desired, etc. Quantification may be performed in the pooled reaction or the reaction forming the amplicons may be aliquoted for quantification. For example, in some instances, the amplicons may be formed and quantification may be performed on the pooled sample, e.g., through quantitative sequencing of the amplicons. In other instances, the amplicons may be formed and quantification may be performed by aliquoting the sample and individually quantifying each amplicon, e.g., by qPCR using primers that hybridize to the amplicon.

In one embodiment of a multiplexed assay, each antigen and/or antibody-binding agent is conjugated to a DNA molecule that contains a sequence unique to the conjugated antigen and/or antibody-binding agent and a universal sequence for bridging polynucleotides. The unique sequence may be or may include a primer binding site. The universal sequence may be complementary to a portion of, including e.g., half of, a bridging polynucleotide such that upon complex formation between an antibody-binding agent-DNA conjugate and an antigen-DNA conjugate, the attached DNA molecules are brought into such proximity that a bridging oligonucleotide may simultaneously bind the universal sequences of the DNA molecules of the antigen-DNA and antibody-binding agent-DNA conjugates, allowing ligation of the two conjugated DNA molecules. The sample, containing a plurality of amplicons formed by the ligation reaction may then be aliquoted into individual reactions, each containing primer sets specific for the primer binding sites of a particular antigen or antibody and allowing for qPCR to be performed for the specific amplicon corresponding to a particular antibody isotype. Accordingly, through amplification of each particular amplicon of the pool the amount of each antibody isotype originally present in the sample may be determined.

Multiplexed assays of the instant disclosure may be performed using a library of antigen-DNA and/or antibody-binding agent-DNA conjugates. Such libraries will vary depending the number and/or type of antigens and/or antibodies to be screened. Accordingly, in some instances, libraries of the instant disclosure may be categorized by the type of antigens contained in the library, including e.g., allergen libraries which contain various allergen antigens for detection of antibodies produced by a host allergic response to an allergen or otherwise serve as a biomarker for a type of allergy; pathogen libraries which contain various pathogen antigens for detection of antibodies produced by a host response to an infection by the pathogen or otherwise serve as a biomarker for an infection; autoimmune libraries which contain various self- or auto-antigens for detection of antibodies produced by a subject as part of an autoimmune disease or otherwise serve as a biomarker for an autoimmune disease; cancer libraries which contain various antigens for detection of antibodies produced by a subject in response to the presence of a cancer or tumor or otherwise serve as a biomarker for cancer, cytokine libraries which contain various cytokine antigens for detection of antibodies produced by the subject as a result of aging or other neurological disorders, and the like. The number of different antigen-DNA conjugates in a library will vary and may range from 10 or less to 1000 or more, including but not limited to e.g., 10 to 1000, 20 to 1000, 30 to 1000, 40 to 1000, 50 to 1000, 60 to 1000, 70 to 1000, 80 to 1000, 90 to 1000, 100 to 1000, 100 to 900, 100 to 800, 100 to 700, 100 to 600, 100 to 500, 100 to 400, 100 to 300, 100 to 200, 10 to 900, 10 to 800, 10 to 700, 10 to 600, 10 to 500, 10 to 400, 10 to 300, 10 to 200, 10 to 100, 20 to 100, 30 to 100, 40 to 100, 50 to 100, 60 to 100, 70 to 100, 80 to 100, 90 to 100, 12, 24, 36, 48, 96, 384, etc. The different polynucleotide antigens of a library may be physically separated, e.g., in separate containers or separate wells of a multi-well plate, or may not be physically separated, i.e., may be pooled, in a single solution, in a single container, etc.

Additionally, a library may include one or more antibody-binding agent-DNA conjugates (e.g., secondary antibody, antibody mimetic, or aptamer DNA conjugates) capable of binding to antibodies of various isotypes. For example, such a library may comprise an anti-IgE secondary antibody-DNA conjugate for detection of IgE, an anti-IgM secondary antibody-DNA conjugate for detection of IgM, an anti-IgG secondary antibody-DNA conjugate for detection of IgG, an anti-IgA secondary antibody-DNA conjugate for detection of IgA, and an anti-IgD secondary antibody DNA conjugate for detection of IgD.

In some instances, a library of antigen-DNA conjugates and antibody-binding agent-DNA conjugates may include a corresponding library of primers, e.g., primer pairs, for quantification of antigen-specific antibody isotypes. In one embodiment, a pooled library of antigen-DNA and antibody-binding agent-DNA conjugates will have a corresponding library of primer pairs for specifically amplifying and quantifying the unique amplicon derived from amplification of the complete barcode sequence produced by joining of the DNA molecules from the antigen-DNA and antibody-binding agent-DNA conjugates (i.e., the barcode produced by complexation of an antigen-DNA conjugate with a target antibody specific for the antigen, which, in turn, is bound by an antibody-binding agent-DNA conjugate, wherein the DNA molecules of the antigen-DNA conjugate and the antibody-binding agent-DNA conjugate in the complex are in sufficient proximity to allow joining by formation of a ligation product or hybridization and polymerase-catalyzed extension, wherein the barcode corresponds to an antigen-specific antibody isotype). In some instances, such a library of primers may contain primer pairs each in individual wells of a multi-well plate such that each well is configured for the amplification and quantification of a particular amplicon specific for a particular antigen-specific antibody isotype upon addition of an aliquot of the ligation reaction to each well. The quantification of each amplicon/antigen-specific antibody isotype of the library thus allows for the determination of the amount of each antigen-specific antibody isotype the library is configured to detect that is present in the initial sample. For example, in some instances, a library having 12 different pairs of antigen-DNA and antibody-binding agent-DNA conjugates will have a corresponding 12-well primer library where each well contains a primer pair configured to amplify an amplicon specific to one of the 12 pairs of antigen-DNA and antibody-binding agent-DNA conjugates for detection of an antigen-specific antibody isotype. In other instances, a library having 24 different pairs of antigen-DNA and antibody-binding agent-DNA conjugates will have a corresponding 24-well primer library where each well contains a primer pair configured to amplify an amplicon specific to one of the 24 pairs of antigen-DNA and antibody-binding agent-DNA conjugates for detection of an antigen-specific antibody isotype. In yet other instances, a library having 48 different pairs of antigen-DNA and antibody-binding agent-DNA conjugates will have a corresponding 48-well primer library where each well contains a primer pair configured to amplify an amplicon specific to one of the 48 pairs of antigen-DNA and antibody-binding agent-DNA conjugates for detection of an antigen-specific antibody isotype. In still other instances, a library having 96 different pairs of antigen-DNA and antibody-binding agent-DNA conjugates will have a corresponding 96-well primer library where each well contains a primer pair configured to amplify an amplicon specific to one of the 96 pairs of antigen-DNA and antibody-binding agent-DNA conjugates for detection of an antigen-specific antibody isotype. In other instances, a library having 384 different pairs of antigen-DNA and antibody-binding agent-DNA conjugates will have a corresponding 384-well primer library where each well contains a primer pair configured to amplify an amplicon specific to one of the 384 pairs of antigen-DNA and antibody-binding agent-DNA conjugates for detection of an antigen-specific antibody isotype. In some instances, a library will have more antigen-DNA conjugates and/or antibody-binding agent-DNA conjugates than corresponding primer pairs provided on a multi-well primer pair plate, including e.g., where the primer library includes multiple plates of primer pairs in order to allow amplification of all of the amplicons of the library.

Libraries of the present disclosure may also include one or more additional reagents for performing all or part of a method as described herein, including e.g., additional reagents for ligation, amplification, detection, etc. In some instances, additional reagents may be included in a pooled library. For example, in some instances, reagents for ligation, e.g., a ligase, may be included within a pooled library of antigen-DNA and antibody-binding agent-DNA conjugates. In some instances, additional reagents may be included in the individual wells of a multi-well plate. For example, in some instances, reagents for amplification, e.g., a polymerase, dNTPs, etc., may be included within the wells of a multi-well plate primer library. Appropriate buffers, salts, etc. may or may not be included in the libraries as described. In some instances, libraries and/or components thereof, e.g., a primer library, may be provided in a lyophilized form and may be rehydrated upon use.

D. Applications

The methods and compositions described herein have particular utility in the detection and/or quantification of antibody isotypes present in a sample. Such detection may find various applications in a variety of technological fields including but not limited to e.g., basic scientific research (e.g., biomedical research, biochemistry research, immunological research, molecular biology research, microbiological research, cellular biology research, genetics, and the like), medical and/or pharmaceutical research (e.g., drug discovery research, drug design research, drug development research, pharmacology, toxicology, medicinal chemistry, preclinical research, clinical research, personalized or "precision" medicine, and the like), medicine, epidemiology, public health, biotechnology, veterinary science, veterinary medicine, agriculture, material science, molecular detection, molecular diagnostics, and the like.

In some instances, methods described herein find use in detection of an antibody in a biological sample from a subject. The term "subject" as used herein refers to an animal, including humans, livestock, pets, laboratory animals, bioproduction animals (e.g., animals used to generate a bioproduct, e.g., an antibody), and the like. In some instances, a sample is derived from a mammalian subject, including e.g., mammalian tissue, mammalian cells, mammalian bodily fluid, mammalian excreted bodily fluids, mammalian semi-solid secretions, and the like.

Mammals of interest from which such samples may be derived include but are not limited to e.g., humans, ungulates (e.g., any species or subspecies of porcine (pig), bovine (cattle), ovine (sheep) and caprine (goats), equine (horses), camelids (camels) or, generally, hooved domestic or farm animals, etc.), rodents (e.g., mice, rats, gerbils, hamsters, guinea pigs, and the like), rabbits, cats, dogs, primates, and the like.

In some instances, samples may be derived from non-human animals including but not limited to non-human mammals. Non-human mammals from which samples may be derived include but are not limited to those listed above. Non-human animals from which samples may be derived include but are not limited to those listed above and, in addition, e.g., avians (i.e., birds, such as, e.g., chicken, duck, etc.), amphibians (e.g., frogs), fish, etc.

In some instances, the methods described herein are used to detect the presence and/or measure the amount of an antibody isotype in a sample derived from a human in order to make an assessment as to whether the subject has a particular condition. In such instances, antibody isotypes derived from the subject will generally be monospecific antibody isotypes, e.g., monospecific antibodies, including e.g., monospecific polyclonal antibodies. Monospecific antibodies measured in a human or non-human subject may be antibodies that are monospecific for a disease antigen where the disease antigen may be endogenous to the host (i.e., a host derived antigen or autoantigen) or may be exogenous to the host (i.e., a non-host derived antigen or infections pathogen derived antigen).

In some embodiments, the methods described herein are utilized for providing an assessment, e.g., in the form of a judgment or appraisal of the presence of, and in some instances a diagnosis of, a subject's condition, determining a therapy for a subject having a condition, monitoring a subject having a condition, etc. In some instances, an assessment of a subject's condition using the methods as described herein includes generating a written report that includes an artisan's assessment of the subject's current state of health i.e., a "diagnosis assessment", of the subject's prognosis, i.e., a "prognosis assessment", of possible treatment regimens, i.e., a "treatment assessment" and/or of responsiveness to therapy, i.e., a "prognosis assessment". Thus, a subject method may further include a step of generating or outputting a report providing the results of a diagnosis assessment, a prognosis assessment, treatment assessment, or a monitoring assessment, and combinations thereof, which report can be provided in the form of an electronic medium (e.g., an electronic display on a computer monitor), or in the form of a tangible medium (e.g., a report printed on paper or other tangible medium).

In some instances, assessments as described herein are performed as part of a treatment regimen, e.g., to assess the effectiveness of treatment or to determine the best timing of treatment or to determine whether modulation of treatment is necessary. For, example, in some instances a pretreatment sample may be collected and assessed according to the methods described herein and from the assessment a treatment protocol is selected. In other instances, a post-treatment sample is collected and compared, according to the assessments described herein, to a pre-treatment sample in order to evaluate treatment effectiveness. In other instances, one or more post treatment assessments are performed to best determine the timing of further therapy.

Conditions, including human and non-human animal conditions, for which the detection methods described herein include but are not limited to those conditions involving a subject's immune system and/or immune response. In some instances, a subject's condition may be pathogen derived (e.g., an infection) and in other instances a subject's condition may be subject derived (e.g., an autoimmune disease or allergy) and in some instances the derivation of the condition may be unknown.

In some instances, the instant methods may find use in detecting allergen-specific antibodies in a subject by detecting the presence of one or more antibodies to an allergen in a sample derived from the subject. Allergens include any type of antigen that produces an abnormally strong immune response, (i.e. allergic response) in a subject having an allergy, wherein the antigen does not normally produce a strong immune response (i.e., associated with antigen-induced clinical signs and symptoms) in subjects who do not have the allergy. An allergen may trigger hypersensitivity mediated in part through an IgE response. In some subjects, hypersensitivity will be diminished by the effects of a concomitant sIgG4 response. The immune response in subjects with allergic responses may also involve other anti-allergen antibodies of various immunoglobulin isotypes (IgG, IgM, IgA, IgD, etc.). An allergic reaction or allergen-induced inflammation may be caused by any ingested or inhaled allergen, which can induce or 'trigger' a harmful IgE-mediated immune reaction. Allergenic source materials may include pollens, animal dander, fungal spores, house dust mite fecal particles, arthropod or reptile venoms, foods, latex, and therapeutic agents such as drugs, anesthetic agents and therapeutic antibodies or other proteins. In particular, food-induced allergic reactions are commonly triggered by peanuts, tree nuts, eggs, milk, shellfish, fish, wheat, soy, sesame seeds, mustard, and celery.

Allergens may be associated with triggering and/or exacerbating IgE-mediated disorders or allergic diseases, allergen-induced inflammation, and asthma, including conditions such as, but not limited to, allergic and atopic asthma, atopic dermatitis and eczema, allergic rhinitis, allergic conjunctivitis and rhinoconjunctivitis, allergic encephalomyelitis, allergic vasculitis, anaphylactic shock, allergies, such as, but not limited to, an animal allergy (e.g., cat), a cockroach allergy, a tick allergy, a dust mite allergy, an insect sting allergy (e.g. (bee, wasp, and others), a food allergy (e.g., strawberries and other fruits and vegetables, peanuts, soy, and other legumes, walnuts and other treenuts, shellfish and other seafood, milk and other dairy products, wheat and other grains, and eggs), a latex allergy, a medication allergy (e.g., penicillin, carboplatin), mold and fungi allergies (e.g., *Alternaria alternata*, *Aspergillus* and others), a pollen allergy (e.g., ragweed, Bermuda grass, Russian thistle, oak, rye, and others), and a metal allergy.

Infection conditions, as used herein, may vary and include any condition in which a foreign antigen is present in a host organism including but not limited to common infectious diseases, emerging infectious diseases, symptomatic infections, asymptomatic infections, and the like. Non-limiting examples of infection conditions include but are not limited to those listed here, which are provided with exemplary condition-causing pathogens, e.g., *Acinetobacter* infections (*Acinetobacter baumannii*), Actinomycosis (*Actinomyces israelii*, *Actinomyces gerencseriae* and *Propionibacterium propionicus*), African sleeping sickness (African trypanosomiasis) (*Trypanosoma brucei*), AIDS (Acquired immunodeficiency syndrome) (HIV (Human immunodeficiency virus)), Amebiasis (*Entamoeba histolytica*), Anaplasmosis (*Anaplasma* genus), Anthrax (*Bacillus anthracis*), *Arcanobacterium haemolyticum* infection (*Arcanobacterium haemolyticum*), Argentine hemorrhagic fever (Junin virus), Ascariasis (*Ascaris lumbricoides*), Aspergillosis (*Aspergillus* genus), Astrovirus infection (Astroviridae family), Babesiosis (*Babesia* genus), *Bacillus cereus* infection (*Bacillus cereus*), Bacterial pneumonia (multiple bacteria), Bacterial vaginosis (BV) (multiple bacteria), *Bacteroides* infection (*Bacteroides* genus), Balantidiasis (*Balantidium coli*), Baylisascaris infection (*Baylisascaris* genus), BK virus infection (BK virus), Black piedra (*Piedraia hortae*), *Blastocystis hominis* infection (*Blastocystis hominis*), Blastomycosis (*Blastomyces dermatitidis*), Bolivian hemorrhagic fever (Machupo virus), *Borrelia* infection (*Borrelia* genus), Botulism (and Infant botulism) (*Clostridium botulinum*), Brazilian hemorrhagic fever (Sabia), Brucellosis (*Brucella* genus), Bubonic plague (the bacterial family Enterobacteriaceae), *Burkholderia* infection (usually *Burkholderia cepacia* and other *Burkholderia* species), Buruli ulcer (*Mycobacterium ulcerans*), Calicivirus infection (Norovirus and Sapovirus) (Caliciviridae family), Campylobacteriosis (*Campylobacter* genus), Candidiasis (*Moniliasis*; Thrush) (usually *Candida albicans* and other *Candida* species), Cat-scratch disease (*Bartonella henselae*), Cellulitis (usually Group A *Streptococcus* and *Staphylococcus*), Chagas Disease (American trypanosomiasis) (*Trypanosoma cruzi*), Chancroid (*Haemophilus ducreyi*), Chickenpox (*Varicella zoster* virus (VZV)), Chikungunya (Alphavirus), Chlamydia (*Chlamydia trachomatis*), *Chlamydophila pneumoniae* infection (Taiwan acute respiratory agent or TWAR) (*Chlamydophila pneumoniae*), Cholera (*Vibrio cholerae*), Chromoblastomycosis (usually *Fonsecaea pedrosoi*), Clonorchiasis (*Clonorchis sinensis*), *Clostridium difficile* infection (*Clostridium dif-* ficile), Coccidioidomycosis (*Coccidioides immitis* and *Coccidioides posadasii*), Colorado tick fever (CTF) (Colorado tick fever virus (CTFV)), Common cold (Acute viral rhinopharyngitis; Acute coryza) (usually rhinoviruses and coronaviruses.), Creutzfeldt-Jakob disease (CJD) (PRNP), Crimean-Congo hemorrhagic fever (CCHF) (Crimean-Congo hemorrhagic fever virus), Cryptococcosis (*Cryptococcus neoformans*), Cryptosporidiosis (*Cryptosporidium* genus), Cutaneous larva migrans (CLM) (usually *Ancylostoma braziliense*; multiple other parasites), Cyclosporiasis (*Cyclospora cayetanensis*), Cysticercosis (*Taenia solium*), Cytomegalovirus infection (Cytomegalovirus), Dengue fever (Dengue viruses (DEN-1, DEN-2, DEN-3 and DEN-4)-Flaviviruses), *Desmodesmus* infection (Green algae *Desmodesmus armatus*), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus (EBOV)), Echinococcosis (*Echinococcus* genus), Ehrlichiosis (*Ehrlichia* genus), Enterobiasis (Pinworm infection) (*Enterobius vermicularis*), *Enterococcus* infection (*Enterococcus* genus), Enterovirus infection (Enterovirus genus), Epidemic typhus (*Rickettsia prowazekii*), Erythema infectiosum (Fifth disease) (Parvovirus B 19), Exanthem subitum (Sixth disease) (Human herpesvirus 6 (HHV-6) and Human herpesvirus 7 (HHV-7)), Fasciolopsiasis (*Fasciolopsis buski*), Fasciolosis (*Fasciola hepatica* and *Fasciola gigantica*), Fatal familial insomnia (FFI) (PRNP), Filariasis (*Filarioidea* superfamily), Food poisoning by *Clostridium perfringens* (*Clostridium perfringens*), Free-living amebic infection (multiple pathogens), *Fusobacterium* infection (*Fusobacterium* genus), Gas gangrene (*Clostridial myonecrosis*) (usually *Clostridium perfringens*; other *Clostridium* species), Geotrichosis (*Geotrichum candidum*), Gerstmann-Straussler-Scheinker syndrome (GSS) (PRNP), Giardiasis (*Giardia intestinalis*), Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (Donovanosis) (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*), Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), *Helicobacter pylori* infection (*Helicobacter pylori*), Hemolytic-uremic syndrome (HUS) (*Escherichia coli* O157:H7, O111 and 0104:H4), Hemorrhagic fever with renal syndrome (HFRS) (Bunyaviridae family), Hepatitis A (Hepatitis A Virus), Hepatitis B (Hepatitis B Virus), Hepatitis C (Hepatitis C Virus), Hepatitis D (Hepatitis D Virus), Hepatitis E (Hepatitis E Virus), Herpes simplex (Herpes simplex virus 1 and 2 (HSV-1 and HSV-2)), Histoplasmosis (*Histoplasma capsulatum*), Hookworm infection (*Ancylostoma duodenale* and *Necator americanus*), Human bocavirus infection (Human bocavirus (HBoV)), Human ewingii ehrlichiosis (*Ehrlichia ewingii*), Human granulocytic anaplasmosis (HGA) (*Anaplasma phagocytophilum*), Human metapneumo virus infection (Human metapneumo virus (hMPV)), Human monocytic ehrlichiosis (*Ehrlichia chaffeensis*), Human papillomavirus (HPV) infection (Human papillomavirus (HPV)), Human parainfluenza virus infection (Human parainfluenza viruses (HPIV)), Hymenolepiasis (*Hymenolepis nana* and *Hymenolepis diminuta*), Epstein-Barr Virus Infectious Mononucleosis (Mono) (Epstein-Barr Virus (EBV)), Influenza (flu) (Orthomyxoviridae family), Isosporiasis (*Isospora belli*), Kawasaki disease (unknown pathogen), Keratitis (multiple pathogens), *Kingella kingae* infection (*Kingella kingae*), Kuru (PRNP), Lassa fever (Lassa virus), Legionellosis (Legionnaires' disease) (*Legionella pneumophila*), Legionellosis (Pontiac fever) (*Legionella pneumophila*), Leishmaniasis (*Leishmania* genus), Leprosy (*Mycobacterium leprae* and *Mycobacterium lepromatosis*), Leptospirosis (*Leptospira* genus), Listeriosis (*Listeria monocytogenes*), Lyme disease (Lyme borreliosis) (usually *Borrelia burgdorferi* and other *Borrelia* species), Lymphatic filariasis (Elephantiasis) (*Wuchereria bancrofti* and *Brugia malayi*), Lymphocytic choriomeningitis (Lymphocytic choriomeningitis virus (LCMV)), Malaria (*Plasmodium* genus), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple pathogens), Meningococcal disease (*Neisseria meningitidis*), Metagonimiasis (usually *Metagonimus yokagawai*), Microsporidiosis (Micro sporidia phylum), *Molluscum contagiosum* (MC) (*Molluscum contagiosum* virus (MCV)), Monkeypox (Monkeypox virus), Mumps (Mumps virus), Murine typhus (Endemic typhus) (*Rickettsia typhi*), *Mycoplasma* pneumonia (*Mycoplasma pneumoniae*), Mycetoma (numerous species of bacteria (*Actinomycetoma*) and fungi (*Eumycetoma*)), Myiasis (parasitic dipterous fly larvae), Neonatal conjunctivitis (*Ophthalmia neonatorum*) (most commonly *Chlamydia trachomatis* and *Neisseria gonorrhoeae*), Nocardiosis (usually *Nocardia asteroides* and other *Nocardia* species), Onchocerciasis (River blindness) (*Onchocerca volvulus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* genus), Pathogenic enteric diseases (including e.g., those caused by pathogenic strains of enteric bacteria (e.g., pathogenic *Clostridium difficile*, pathogenic *Salmonella enterica*, pathogenic *Bacillus cereus*, pathogenic *Helicobacter pylori*, pathogenic *Campylobacter*, etc.), Pediculosis capitis (Head lice) (*Pediculus humanus* capitis), Pediculosis corporis (Body lice) (*Pediculus humanus corporis*), Pediculosis pubis (Pubic lice, Crab lice) (*Phthirus pubis*), Pelvic inflammatory disease (PID) (multiple pathogens), Pertussis (Whooping cough) (*Bordetella pertussis*), Plague (*Yersinia pestis*), Pneumococcal infection (*Streptococcus pneumoniae*), Pneumocystis pneumonia (PCP) (*Pneumocystis jirovecii*), Pneumonia (multiple pathogens), Poliomyelitis (Poliovirus), *Prevotella* infection (*Prevotella* genus), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Rat-bite fever (*Streptobacillus moniliformis* or *Spirillum minus*), Respiratory syncytial virus infection (Respiratory syncytial virus (RSV)), Rhinosporidiosis (*Rhino sporidium seeberi*), Rhinovirus infection (Rhinovirus), Rickettsial infection (*Rickettsia* genus), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), Salmonellosis (*Salmonella* genus), SARS (Severe Acute Respiratory Syndrome) (SARS coronavirus), Scabies (*Sarcoptes scabiei*), Schistosomiasis (*Schistosoma* genus), Sepsis (multiple pathogens, including e.g., *Capnocytophaga*), Shigellosis (Bacillary dysentery) (*Shigella* genus), Shingles (Herpes zoster) (*Varicella zoster* virus (VZV)), Smallpox (Variola) (Variola major or Variola minor), Sporotrichosis (*Sporothrix schenckii*), Staphylococcal food poisoning (*Staphylococcus* genus), Staphylococcal infection (*Staphylococcus* genus), Strongyloidiasis (*Strongyloides stercoralis*), Subacute sclerosing panencephalitis (Measles virus), Syphilis (*Treponema pallidum*), Taeniasis (*Taenia* genus), Tetanus (Lockjaw) (*Clostridium tetani*), Tinea barbae (Barber's itch) (usually *Trichophyton* genus), Tinea capitis (Ringworm of the Scalp) (usually *Trichophyton tonsurans*), Tinea corporis (Ringworm of the Body) (usually *Trichophyton* genus), Tinea cruris (Jock itch) (usually *Epidermophyton floccosum, Trichophyton rubrum*, and *Trichophyton mentagrophytes*), Tinea manum (Ringworm of the Hand) (*Trichophyton rubrum*), Tinea nigra (usually *Hortaea werneckii*), Tinea pedis (Athlete's foot) (usually *Trichophyton* genus), Tinea unguium (Onychomycosis) (usually *Trichophyton* genus), Tinea versicolor (*Pityriasis versicolor*) (*Malassezia* genus), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Trinochccliasis (*Toxoplasma gondii*), Trichinlosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid Fever (*Salmonella enterica* subsp. *enterica, serovar typhi*), Ureaplasma urealyticum infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), Viral pneumonia (multiple viruses), West Nile Fever (West Nile virus), White piedra (Tinea blanca) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zika virus disease (Zika virus), Zygomycosis (Mucorales order (Mucormycosis) and Entomophthorales order (Entomophthoramycosis)), and the like. Generally herein, detection of an infection condition according to the described methods includes detecting a host immune response to the infection by detecting one or more antigen-specific antibody isotypes, e.g., a host derived antibody to a pathogen derived antigen, present in a sample derived from the host.

Accordingly, in some instances, the instant methods may find use in detecting the presence of a pathogen in a subject derived or other type of sample by detecting the presence of one or more antibodies to the pathogen or a component thereof in the sample. Pathogens that may be detected according to the instant methods include but are not limited to e.g., viral pathogens, bacterial pathogens, fungal pathogens, protozoa pathogens, and the like. As will be readily understood, the presence of a newly discovered pathogen within a sample may be assayed for by isolating an antigenic component from the pathogen for use as a polynucleotide-conjugated antigen in according to one or more embodiments of the instant disclosure.

In some instances, the method described herein will detect and/or measure the presence of an antibody to an HIV antigen including but not limited to e.g., HIV-1 antigens, HIV-2 antigens, HIV-1/2 antigens, p16, p14, p24, p55, gp120, gp160, gp41, gp36, and the like.

Autoimmune conditions, as used herein, may vary and include any condition in which a subject's own immune cells attack healthy tissue and/or a subject develops an immune response to a subject-derived antigen including but not limited to symptomatic autoimmune diseases, asymptomatic autoimmune diseases, acute autoimmune diseases, chronic autoimmune diseases, transplant induced autoimmune diseases, and the like. Without being bound by theory, in some instances an autoimmune disease may be triggered by the presence of a foreign substance but the activated immune response may not be specifically directed to the foreign substance. Areas of the body generally affected by autoimmune conditions include but are not limited to, e.g., blood vessels, connective tissue, endocrine tissues (e.g., thyroid tissues, pancreas tissues, etc.), joint tissues, muscle tissues, hematopoietic tissues (e.g., including red blood cells and the like), epithelial tissues (e.g., including the skin and gut). Non-limiting examples of autoimmune conditions and autoimmune-related conditions include but are not limited to, e.g., Acute Disseminated Encephalomyelitis (ADEM), Acute necrotizing hemorrhagic leukoencephalitis, Addison's disease, Adrenalitis, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called "Wegener's" Granulomatosis), Graves' disease, Guillain-Barre syndrome, Hashimoto's encephalitis, Hashimoto's thyroiditis, Hemolytic anemia, Henoch-Schonlein purpura, *Herpes gestationis*, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA), and the like. Generally herein, detection of an autoimmune condition according to the described methods includes detecting a subject autoimmune response by detecting one or more antigen-specific antibody isotypes, e.g., a subject derived autoimmune antibody to a subject derived antigen, present in a sample derived from the subject. In some instances, a particular autoimmune disease may be characterized by the presence of multiple different autoantibodies of various isotypes and, thus, multiplexed methods for detection, as described herein, may be utilized to detect or measure the levels of a panel of autoimmune-related autoantibodies.

Methods of the instant disclosure may find use in detecting one or more clinically relevant autoantibodies including but not limited to e.g., one or more autoantibodies generated by a subject in response to a neoplasm including but not limited to e.g., where the neoplasm is one or more of prostate cancer, breast cancer, lung cancer, colon cancer, stomach cancer, liver cancer and thyroid cancer. In certain instances, detection may be performed before the presence of disease symptoms. In other instances, detection may be performed following the presence of disease symptoms including e.g., after the appearance of one or more disease symptoms but prior to treatment, during treatment, following treatment, or a combination thereof.

Useful autoantibodies may include cancer autoantibodies (i.e., antibodies that are indicative of the presence of a cancer). Cancer autoantibodies that may identify or predict the presence of a cancer may include but are not limited to e.g., prostate cancer autoantibodies (including but not limited to e.g., those biomarker autoantibodies that specifically bind the gene product of alpha-methylacyl-CoA racemase (AMACR), Bromodomain Containing 2 (BRD2), Caldesmon 1 (CALD1), Eukaryotic Translation Initiation Factor 4 Gamma, 1 (EIF4G1), kallikrein-3 (KLK3), New York Esophageal Squamous Cell Carcinoma 1 (NY-ESO-1), Parkinson Protein 7 (PARK7), PC4 And SFRS 1 Interacting Protein 1 (PSIP1), Ribosomal Protein L13a (RPL13A), Ribosomal Protein L22 (RPL22), Synovial Sarcoma, X Breakpoint 2 (SSX2), (TAR DNA Binding Protein (TAR-DBP), Transferrin Receptor (TFRC), talin 1 (TLN1), X antigen family member D3 (XAGE1B), etc.), breast cancer autoantibodies (including but not limited to e.g., those biomarker autoantibodies that specifically bind the gene product of Alpha2-HS glycoprotein (AHSG), ASB9 ankyrin repeat and SOCS box containing 9 (ASB9), Breast Cancer 1, Early Onset (BRCA1), Breast Cancer 2, Early Onset (BRCA2), Carcinoembryonic antigen-related cell adhesion molecules (CEACAM) genes, Eukaryotic elongation factor-2 kinase (EEF2K), erb-b2 receptor tyrosine kinase 2 (ERBB2), heat-shock protein 60 (HSP60), mucin 1 (MUC1), Myc, NY-ESO-1, cyclin-dependent kinase inhibitor 2A (p16), PARK7, RELT tumor necrosis factor receptor, serine active site containing 1 (SERAC1), tumor protein p53 (TP53), etc.), lung cancer autoantibodies (including but not limited to e.g., those biomarker autoantibodies that specifically bind the gene product of annexin A1 (ANXA1), cancer antigen 1 (CAGE1), CEACAM genes, enolase 1 (ENO1), ERBB2, GBU4-5, gastrin releasing peptide (GRP), MUC1, Myc, NY-ESO-1, phosphoglycolate phosphatase (PGP), ribosomal protein SA (RPSA), superoxide dismutase 2 (SOD2), TP53, Triose phosphate isomerase (TPI), tyrosine 3-monooxygenase/tryptophan 5-monooxygenase activation protein theta (YWHAQ), etc.), colon cancer autoantibodies (including but not limited to e.g., those biomarker autoantibodies that specifically bind the gene product of cyclin B1 (CCNB 1), cyclin Dl (CCND1), CEACAM genes, GRP, HSP60, IMP (inosine 5'-monophosphate) dehydrogenase 1 (IMPDH1), insulin like growth factor 2 mRNA binding protein 3 (KOC), mucin 5AC (MUC5AC), Myc, nucleobindin 1 (NUCB 1), nucleoporin 62 kDa (NUP62), p16, Fas (TNF receptor superfamily member 6) (TNFRSF6), TP53, etc.), stomach cancer autoantibodies (including but not limited to e.g., those biomarker autoantibodies that specifically bind the gene product of CEACAM genes, GRP, MUC1, TP53, etc.), liver cancer autoantibodies (including but not limited to e.g., those biomarker autoantibodies that specifically bind the gene product of alpha fetoprotein (AFP), Apoptosis inducing factor (AIF), angiotensin I converting enzyme (DCP), DEAD-box helicase 3, X-linked (DDX3X), EEF2K, glyceraldehyde-3-phosphate dehydrogenase (GAPDH), thyroid carcinoma, Hurthle cell (HCC), heterogeneous nuclear ribonucleoprotein A2 (HNRNPA2), HSP70, NUP62, polycystin 1, transient receptor potential channel interacting (PBP), peroxiredoxin (PRDX), SOD2, TP53, TPI, etc.), and the like.

Accordingly, in some instances, a subject of the instant disclosure may include a subject having cancer, a subject suspected of having cancer and/or a subject having been or being treated for cancer including but not limited to e.g., prostate cancer, breast cancer, lung cancer, colon cancer, stomach cancer, liver cancer, and the like.

In some instances, a subject of the instant disclosure may have or be suspected of having one or more paraneoplastic syndrome, i.e., a syndrome that is the consequence of cancer in the body but that is not due to the local presence of cancer cells. Paraneoplastic syndromes include but are not limited to e.g., endocrine paraneoplastic syndromes (including e.g., Cushing syndrome, syndrome of inappropriate antidiuretic hormone (ADH) secretion (SIADH), hypercalcemia, hypoglycemia, carcinoid syndrome, polycythemia, hyperaldosteronism, etc.), neurological paraneoplastic syndromes (including e.g., Lambert-Eaton myasthenic syndrome (LEMS), Paraneoplastic cerebellar degeneration, Encephalomyelitis, Limbic encephalitis, Brainstem encephalitis, Opsoclonus myoclonus ataxia syndrome, anti-NMDA receptor encephalitis, Polymyositis, etc.), mucocutaneous paraneoplastic syndromes (including e.g., Acanthosis nigricans, Dermatomyositis, Leser-Trelat sign, Necrolytic migratory erythema, Sweet's syndrome, Florid cutaneous papillomatosis, Pyoderma gangrenosum, Acquired generalized hypertrichosis, etc.), hematological paraneoplastic syndromes (including e.g., Granulocytosis, Polycythemia, Trousseau sign, Nonbacterial thrombotic endocarditis, Anemia, etc.), Membranous glomerulonephritis, Tumor-induced osteomalacia, Stauffer syndrome, Neoplastic fever, and the like. Accordingly, the instant methods may identify the presence of or predict the presence of one or more paraneoplastic syndromes or a neoplasm associated with the paraneoplastic syndrome in a subject e.g., by the detection of an autoantibody in the subject.

In some instances, the methods of the instant disclosure include identifying or predicting the presence of autoantibodies associated with dermatomyositis, including but not limited to e.g., autoantibodies to one or more gene products of MORC family CW-type zinc finger 3 (NXP2), tripartite motif containing 33 (TIFly), small ubiquitin like modifier activating enzyme (SAE), and the like.

In some instances, the methods of the instant disclosure include identifying or predicting the presence of autoantibodies associated with systemic sclerosis, including but not limited to e.g., autoantibodies to RNA polymerase III.

In some instances, the methods of the instant disclosure include identifying or predicting the presence of autoantibodies associated with Lambert-Eaton myasthenic syndrome, including but not limited to autoantibodies to one or more gene products of voltage-gated calcium channel genes.

In some instances, the methods of the instant disclosure include identifying or predicting the presence of autoantibodies associated with Myasthenia gravis, including but not limited to autoantibodies to one or more gene products of Titin, ryanodine receptor, and the like.

In some instances, the methods of the instant disclosure include identifying or predicting the presence of autoantibodies associated with Paraneoplastic pemphigus, including but not limited to autoantibodies to one or more gene products of Desmoplakins I, esmoplakins II, envoplakin, plectin, periplakin, and the like.

In some instances, the methods of the instant disclosure include identifying or predicting the presence of autoantibodies associated with Paraneoplastic neurological disease including but not limited to autoantibodies to one or more gene products/antigens of Hu (Anti-Neuronal Autoantibody 1 (ANNA1), Yo (Purkinje cell cytoplasmic antibody type 1 (PCA-1)), Ri (Anti-Neuronal Autoantibody 2 (ANNA2), Ma1/2 (Paraneoplastic antigen Ma1/2 PNMA1/2), CV2 (CV2/CRMPS-Ab), amphiphysin, SRY (sex determining region Y)-box 1 (SOX1), Zic family member 4 (Zic4), Tr (Delta/Notch-Like Epidermal Growth Factor-Related Receptor (DNER)), protein kinase C, gamma (PKCy), CARPVII, Ca/ARHGAP26, and the like.

In some instances, subjects of the instant disclosure may include subjects having or suspected of having or being treated for a neurological disorder, including e.g., neurological disorders with an autoimmune component (e.g., neuroinflammatory diseases, inflammatory neuromuscular diseases, etc.) including but not limited to e.g., Myasthenia gravis, multiple sclerosis, and the like. As such, in some instances, the methods of the instant disclosure may include identifying or predicting the presence of autoantibodies associated with a neurological disorder including but not limited to e.g., autoantibodies that bind a component of the voltage-gated potassium channel complex (e.g., VGKC, LG11, CASPR2, etc.), autoantibodies that bind a NMDA receptor (e.g., NR2), autoantibodies that bind an AMPA receptor, autoantibodies that bind a GABAA/B receptor, autoantibodies that bind a dipeptidyl-peptidase-like protein-6 (DPPX), antibodies that bind to IgLON5, autoantibodies that bind to a pathogenic component of Myasthenia gravis or autoantibodies generally associated with Myasthenia gravis (including but not limited to e.g., anti-acetylcholine receptor (AChR) antibodies, anti-muscle specific kinase (MuSK) antibodies, anti-lipoprotein related protein (LRP)4, antibodies to agrin, antibodies to cortactin, and the like), autoantibodies that bind to a pathogenic component of multiple sclerosis or autoantibodies generally associated with multiple sclerosis (including e.g., anti-aquaporin 4 antibodies, anti-myelin antibodies (anti-MOG, anti-MBP, etc.), anti-KIR4.1 antibodies, anti-SPAG16 antibodies, etc.).

In some instances, subjects of the instant disclosure may be subjects having or suspected of having, or being treated for biliary cirrhosis. As such, in some instances, the methods of the instant disclosure may include identifying or predicting the presence of biliary cirrhosis through the detection or measurement of one or more biliary cirrhosis associated antibodies including but not limited to e.g., anti-M2 mitochondrial antibodies.

In some instances, subjects of the instant disclosure may be subjects having or suspected of having, or being treated for autoimmune rheumatic diseases. As such, in some instances, the methods of the instant disclosure may include identifying or predicting the presence of autoimmune rheumatic diseases through the detection or measurement of one or more autoimmune rheumatic diseases associated antibodies including but not limited to e.g., anti-nuclear antibodies, anti-SSA autoantibodies (Anti-Sjogren's-syndrome-related antigen A) anti-Sjogren's syndrome type B (SSB) antibodies, anti-Smith antibodies, anti-U1RNP antibody, anti-double stranded DNA antibody, anti-phospholipid antibodies, anti-citrullinated protein antibodies, and the like.

In some instances, subjects of the instant disclosure may be subjects having or suspected of having, or being treated for idiopathic inflammatorymyopathies (IIMs), also separately referred to as polymyositis (PM) and dermatomyositis (DM). As such, in some instances, the methods of the instant disclosure may include identifying or predicting the presence of IIMs through the detection or measurement of one or more IIM associated antibodies including but not limited to e.g., anti-Jo-1 antibodies, aminoacyl-tRNA synthetase autoantibodies (e.g., Jo-1 (histidyl) antibodies, PL-7 (threonyl) antibodies, PL-12 (alanyl) antibodies, OJ (isoleucyl) antibodies, EJ (glycyl) antibodies, KS (asparaginyl) antibodies, Zo (phenylalanyl) antibodies and Ha (tyrosyl) antibodies, etc.), anti-Mi-2 antibodies, anti-MDA5 antibodies, anti-NXP2 antibodies, anti-SAE antibodies, and anti-TIFly (p 155/140) antibodies, and the like.

In some instances, subjects of the instant disclosure may be subjects having or suspected of having, or being treated for non-inflammatory muscle necrosis. As such, in some instances, the methods of the instant disclosure may include identifying or predicting the presence of noninflammatory muscle necrosis through the detection or measurement of one or more non-inflammatory muscle necrosis associated antibodies including but not limited to e.g., anti-3-hydroxy-3-methylglutaryl-coenzyme A reductase (HMGCR) antibodies.

In some instances, subjects of the instant disclosure may be subjects having or suspected of having, or being treated for systemic sclerosis and mixed-connective tissue disease. As such, in some instances, the methods of the instant disclosure may include identifying or predicting the presence of systemic sclerosis and/or mixed-connective tissue disease through the detection or measurement of one or more systemic sclerosis or mixed-connective tissue disease associated antibodies including but not limited to e.g., anti-PM-Scl antibodies, anti-Ku antibodies, and anti-U1RNP antibodies, and the like.

In some instances, subjects of the instant disclosure may be subjects having or suspected of having, or being treated for a metabolic disease (e.g., diabetes including e.g., type 1 diabetes). As such, in some instances, the methods of the instant disclosure may include identifying or predicting the presence of a metabolic disease through the detection or measurement of one or more metabolic disease associated antibodies including but not limited to e.g., anti-Glutamic acid decarboxylase (GAD) antibodies, anti-tyrosine phosphatase-like molecule antibodies, anti-IA-2 antibodies and anti-insulin antibodies, e.g., as useful in detecting and/or monitoring type 1 diabetes.

In some instances, disorders of the instant disclosure and autoantibodies that may be detected using the methods as described herein for the identification of a condition or as part of a prognosis for a condition in a subject include but are not limited to e.g., those described in Zaenker & Ziman. Cancer Epidemiol Biomarkers Prev. (2013) 22(12):2161-81; Leslie et al. J Clin Invest (2001) 108(10): 1417-22; Damoiseaux et al. Autoimmunity Reviews (2015) 14:555-563, the disclosures of which are incorporated herein by reference in their entirety.

In some instances, the methods described herein may find use in monitoring a patient following a treatment, e.g., following surgery, including tissue transplantation, following cancer therapy, following treatment for an infectious condition, following treatment for an autoimmune condition, and the like. In some instances, the methods described herein may be used to monitor a subject following surgical treatment for cancer, e.g., to monitor autoantibody levels associated with the presence or absence of cancer following surgical cancer removal. For example, in one embodiment, the methods described herein may be used to monitor one or more thyroglobulin autoantibodies following thyroidectomy. In some instances, methods of the instant disclosure find use in detecting one or more anti-thryo globulin antibodies, one or more anti-Clq antibodies, one or more anti-MPO antibodies, one or more anti-transglutaminase antibodies, one or more anti-Sm/RNP antibodies, one or more anti-GAD65 antibodies, one or more anti-Ro/SSA antibodies, one or more anti-JO-1 antibodies, one or more anti-IA-2 antibodies, one or more anti-La/SSB antibodies, one or more anti-PR3 antibodies, one or more anti-Sm B/B' antibodies, one or more anti-CENP-A antibodies, one or more anti-U1-snRNP-C antibodies, one or more anti-Gliadin antibodies, one or more anti-Histone H3 antibodies, one or more anti-H2B antibodies, one or more anti-SmD antibodies, one or more anti-Histone H4 antibodies or one or more anti-insulin H antibodies. Accordingly, in some instances, an antigen of the instant method may be one or more thryoglobulin antigens, one or more Clq antigens, one or more MPO antigens, one or more transglutaminase antigens, one or more Sm/RNP antigens, one or more GAD65 antigens, one or more Ro/SSA antigens, one or more JO-1 antigens, one or more IA-2 antigens, one or more La/SSB antigens, one or more PR3 antigens, one or more Sm B/B' antigens, one or more CENP-A antigens, one or more U1-snRNP-C antigens, one or more Gliadin antigens, one or more Histone H3 antigens, one or more H2B antigens, one or more SmD antigens, one or more Histone H4 antigens or one or more insulin H antigens. In certain multiplex assays a particular assay may include a combination of multiple antigens, individually conjugated to a polynucleotide as described herein, where the antigens may be each of or be selected from a thryoglobulin antigen, a Clq antigen, a MPO antigen, a transglutaminase antigen, a Sm/RNP antigen, a GAD65 antigen, a Ro/SSA antigen, a JO-1 antigen, a IA-2 antigen, a La/SSB antigen, a PR3 antigen, a Sm B/B' antigen, a CENP-A antigen, a U1-snRNP-C antigen, a Gliadin antigen, a Histone H3 antigen, a H2B antigen, a SmD antigen, a Histone H4 antigen and/or an insulin H antigen.

In some instances, the subject methods find use in normalizing measured values for one or more antibody isotypes present in a sample. For example, in some instances the level of a particular antibody isotype may be normalized according to the level of a second antibody present in the sample. In some instances, the level of an antibody may be normalized according to the level of one or more immunoglobulins present in the sample. In some instances, the level of immunoglobulin in a sample may be indicative of an immunoglobulin deficiency.

Any convenient sample may be used in performing the methods as described herein. In some instances, samples obtained from a subject, e.g., patient samples, may include but are not limited to, e.g., tissues samples (e.g., biopsy samples). Tissue samples, as used herein, generally refers to samples that contain cells and other components and may vary but generally include skin tissue samples, muscle tissue samples, tumor tissue samples, blood samples, bone samples, bone marrow samples, brain tissue samples, connective tissue samples, and the like. In some instances, e.g., where a tissue sample is solid or semi-solid, a tissue sample may be liquefied or a cellular sample may be dissociated and/or homogenized prior to use in the methods as described herein. In some instances, such pre-processing is not necessary, e.g., when the tissue is a liquid tissue sample, e.g., blood. In some instances, the methods described herein may be performed on solid or semi-solid tissue samples without pre-processing, e.g., on tissue sections or cytological samples of cells obtained from a solid or semi-solid tissue, e.g., as performed in histological or cytological methods. Accordingly, in some instances, the subject method may find use in staining, e.g., for the identification of an antibody, a histological or cytological sample.

In certain embodiments, the specificity of the antibody detection method of the instant disclosure is independent of the presence of anti-polynucleotide antibodies in the sample. As such, the described assay may be performed regardless of whether an anti-polynucleotide antibody is or is not present in the sample. In some instances, a sample of the instant disclosure may be a sample known to contain anti-polynucleotide antibodies. In some instances, a sample of the instant disclosure may be a sample suspected to contain anti-polynucleotide antibodies. The term "anti-polynucleotide antibody" as used herein includes those antibodies produced by a subject's immune system that specifically bind one or more polynucleotides including but not limited to e.g., anti-DNA autoantibodies, anti-double-stranded DNA (dsDNA) antibodies, anti-single-stranded DNA (ssDNA) antibodies, etc.

Anti-DNA antibodies have some prevalence in the general population and certain subjects, including those predisposed to of having autoimmune disease, have an increased likelihood of displaying anti-DNA antibodies in their blood. In addition, certain conditions are or may be correlated with the presence and/or increased levels of anti-DNA antibodies. Such conditions include but are not limited to e.g., sytemic lupus erythrumatosus (SLE), Rheumatological diseases (e.g., Antiphospholipid antibody syndrome, Rheumatoid arthritis, CREST (calcinosis, Raynaud's disease, esophageal dysmotility, sclerodactyly, and telangiectasia), Scleroderma, Vasculitis, Juvenile rheumatoid arthritis, Mixed connective tissue disease, etc.), Malignancy diseases (e.g., Lymphoma and other cancers), Infectious diseases (e.g., Tuberculosis and other infections), Endocrine disorders, Hepatitis (e.g., Autoimmune hepatitis, Chronic hepatitis B, etc.), Sarcoidosis, Familial Mediterranean fever, Idiopathic thrombocytopenic purpura, Rheumatic heart disease, Myasthenia Graves' disease, End stage renal disease, Ulcerative colitis, Epilepsy, Fibromyalgia, Osteochondritis, Osteoarthritis, Evans syndrome, Skin psoriasis, Skin rash, multiple sclerosis, and the like. Subjects and conditions associated with the presence or increased levels of anti-DNA antibodies include but are not limited to e.g., those described in e.g., Isenberg et al. Rheumatology (Oxford). (2007) 46(7): 1052-6; Attar et al. Saudi Med J. (2010) 31(7):781-7 and Williamson et al. Proc Natl Acad Sci USA. (2001) 98(4): 1793-8; the disclosures of which are incorporated herein by reference in their entirety.

In some instances, patient samples (e.g., blood, serum, etc.) may contain or may be more likely to contain or suspected of containing anti-polynucleotide antibodies, including e.g., those anti-DNA antibody associated conditions described above and in the human patient population in general. The inventors of the instant disclosure have discovered that, in certain instances, anti-polynucleotide antibodies can interfere with agglutination assays by, without being bound by theory, interfering with agglutination of desired antigens by target antibodies and/or generating false-positive agglutination of polynucleotide-bound antigens with anti-polynucleotide antibodies. In some instances, the deleterious effects of anti-polynucleotide antibodies on an agglutination assay as described herein may be mitigated by the addition of unbound (i.e., free) polynucleotide to the agglutination reaction.

In certain instances, methods of the instant disclosure include the addition of free DNA, e.g., free ssDNA) to the agglutination reaction, including where such free DNA is added to samples known or expected to contain anti-DNA antibodies and where free DNA is added prophylactically to sample where the presence of anti-DNA antibodies is unknown or unexpected. Useful amounts of free DNA in an agglutination reaction will vary and useful concentrations may range from 0.1 µM or less to 1 mM or more, including but not limited to e.g., from 0.1 µM to 1 mM, 1 µM to 1 mM, 2 µM to 1 mM, 3 µM to 1 mM, 4 µM to 1 mM, 5 µM to 1 mM, 6 µM to 1 mM, 7 µM to 1 mM, 8 µm to 1 mM, 9 µM to 1 mM, 10 µM to 1 mM, 0.1 µM to 100 µM, 1 µM to 100 µM, 2 µM to 100 µM, 3 µM to 100 µM, 4 µM to 100 µM, 5 µM to 100 µM, 6 µM to 100 µM, 7 µM to 100 µM, 8 µM to 100 µM, 9 µM to 100 µM, 10 µM to 100 µM, etc. Useful free DNA in agglutination reactions (i.e., competitive DNA or blocking DNA) will generally not have significant homology to the antigen-bound polynucleotides or other polynucleotides (e.g., bridge polynucleotides, splint polynucleotides, etc.), where "significant homology is considered homology sufficient for hybridization under normal reaction conditions. Accordingly, the structure (e.g., length, nucleotide content, sequence, etc.) of such free DNA will vary widely. In some instances, the free DNA may range from 50 or less nucleotides to 100 or more, including but not limited to e.g., 50 to 100 nucleotides, 50 to 95 nucleotides, 50 to 90 nucleotides, 50 to 85 nucleotides, 50 to 80 nucleotides, 55 to 100 nucleotides, 60 to 100 nucleotides, 60 to 90 nucleotides, 60 to 80 nucleotides, 60 nucleotides, 65 nucleotides, 70 nucleotides, 75 nucleotides, 80 nucleotides, 85 nucleotides, etc. In some instances, the G/C content of the free DNA will be 50% or less including but not limited to e.g., from 30% to 50%, 35% to 50%, 40% to 50%, 45% to 50%, etc.

In some instances, a sample is a blood sample. Blood samples may be analyzed as whole blood samples or may be partially or totally fractionated. In some instances, a fractionated blood sample my produce a serum sample upon which the detection methods described herein may be performed or a plasma sample upon which the detection methods described herein may be performed.

In some instances, a sample may be an excreted bodily fluid or semi-solid such that obtaining the sample is performed non-invasively and/or without any injury to the subject.

Excreted bodily fluids and/or semi-solids of interest include but are not limited to, e.g., urine, saliva, tears, sweat, pus and stool. In some instances, the high sensitivity of the subject methods allows for detection of an antibody isotype in an excreted bodily fluid or semi-solid where traditional agglutination methods and/or ELISA does not.

In some instances, e.g., in biotechnological and/or pharmaceutical applications, a sample may be assayed for the presence of a particular antibody isotype and/or measured (e.g., titered) for the amount of a particular antibody isotype as a step in the process of producing a particular antibody isotype and/or screening the activity of an agent targeting a particular antibody isotype. In some instances, samples in which the methods described herein find use are cellular samples generated in a laboratory. Such cellular laboratory samples may be in vitro or in vivo generated. In some instances, a cellular sample is an in vitro derived hybridoma and the subject antibody is an antibody produced by the hybridoma. In some instances, a cellular sample is an in vivo derived hybridoma and the subject antibody is an antibody produced by the hybridoma. As such, in some instances, the subject methods described herein, and the multiplexed methods described herein, find use in screening hybridomas. Hybridoma screening may be performed for the detection of a desired natural or synthetically produced antibody including but not limited to e.g., a monoclonal antibody, a polyclonal antibody, a multi-specific antibody (e.g., a bispecific antibody), and the like.

Methods of hybridoma production and analysis wherein the described methods find use will be readily apparent to the ordinary skilled artisan and include, e.g., those described in Methods in Molecular Biology: Immunochemical Protocols. Ed. Burns, R., Humana Press, 2005, the disclosure of which is incorporated herein by reference in its entirety.

In some instances, a cell expressing an antibody, e.g., a B-cell, a T-cell, a hybridoma cell, etc., may be identified as expressing the antibody, e.g., a B-cell receptor, a T-cell receptor, an antibody, etc., through detection of an associated elongated polynucleotide or amplification product generated according to the methods described herein. In some instances, an elongation and/or amplification product generated based on aggregation of polynucleotide-bound antigen and antibody may be detected using detectable probe nucleic acid, e.g., a fluorescently tagged probe nucleic acid, allowing identification of a cell associated with the elongation and/or amplification product. For example, in some instances, an elongation and/or amplification product generated based on aggregation of polynucleotide-bound antigen and antibody may be detected using detectable probe nucleic acid, e.g., a fluorescently tagged probe nucleic acid, allowing identification of the cell that produced the antibody. In some instances, such identification allows for the quantification of the relative binding of the antibody of the identified cell to the antigen (e.g., allowing identification of a cell producing an antibody with antigen-antibody binding or with superior antigen-antibody binding). In some instances, such identification allows for the sorting of cells (e.g., by FACS) based on their production of antibody and/or based on their production of relatively superior antibody, e.g., where multiple different cells are assayed in parallel or in multiplexed fashion.

In some instances, the method described herein find use in screening a host animal which has been immunized to generate antibodies. Any convenient host animal antibody production system may find use in combination with the methods described herein and may include but is not limited to, e.g., those subject animals described above.

As biotechnological and/or pharmaceutical applications encompass the use and/or production of monospecific and multispecific (e.g., bispecific) antigen binding members, the subject methods as described herein may generally be configured for the detection of monospecific or multispecific antibodies, e.g., monospecific or multispecific antibodies (e.g., bispecific antibodies).

The above described uses are in no way to be considered limiting as the methods and compositions described herein may have additional utility not described herein.

E. Compositions and Kits

The instant disclosure includes compositions, e.g., reagents, kit, and devices, useful in practicing the methods described herein. Any of the reagents described herein may find use individually in a method or kit for detecting antibodies. For example, the instant disclosure provides antigen-DNA conjugates and antibody-binding agent-DNA conjugates useful in the described assays.

As noted above, the antigen-DNA conjugates and antibody-binding agent-DNA conjugates may be generated by any convenient method. In some instances, the polynucleotide and the antigen or antibody-binding agent may be directly linked, e.g., via a single bond, or indirectly linked e.g., through the use of a suitable linker, e.g., a polymer linker, a chemical linker, or one or more linking molecules or moieties. In some instances, attachment of the polynucleotide to the antigen or antibody-binding agent may be by way of one or more covalent interactions. In some instances, the antigen may be functionalized, e.g., by addition or creation of a reactive functional group, for binding to the polynucleotide. In some instances, the polynucleotide may be functionalized, e.g., by addition or creation of a reactive functional group, for binding to the antigen. Functionalized antigens, antibody-binding agents, and/or polynucleotides may be modified to contain any convenient reactive functional group for conjugation. In some instances, the polynucleotide is functionalized to comprise one or more functional groups including an amine functional group, e.g., a terminal amine functional group, a carboxylic functional group, e.g., a terminal carboxylic functional group or a sulfhydryl group, a thiol functional group, e.g., as in thiolated or thiol-modified oligonucleotides, and the like.

In instances where a polynucleotide is functionalized with an amine functional group and/or a carboxylic functional group and/or a sulfhydryl group and a polypeptide antigen or antibody, the functionalized polynucleotide and the polypeptide antigen or antibody may be conjugated by any convenient method of protein conjugation including but not limited to protein crosslinking including but not limited to, e.g., glutaraldehyde crosslinking, carbodiimide crosslinking, succinimide ester crosslinking, imidoester, crosslinking, maleimide crosslinking, iodoacetamide crosslinking, benzidine crosslinking, periodate crosslinking, isothiocyanate crosslinking, and the like. Such conjugation methods may optionally use a reactive sidechain group of an amino acid residue of the polypeptide antigen (e.g., a reactive side-chain group of a Lys, Cys, Ser, Thr, Tyr, His or Arg amino acid residue of the protein, i.e., a polypeptide linking group may be amino-reactive, thiol-reactive, hydroxyl-reactive, imidazolyl-reactive or guanidinyl-reactive). In some cases, a chemoselective reactive functional group may be utilized that conjugates to a compatible function group on the polynucleotide. Chemoselective reactive functional groups for inclusion in the subject polypeptide antigen include, but are not limited to: an azido group, an alkynyl group, a phosphine group, a cysteine residue, a C-terminal thioester, aryl azides, maleimides, carbodiimides, N-hydroxysuccinimide (NHS)-esters, hydrazides, PFP-esters, hydroxymethyl phosphines, psoralens, imidoesters, pyridyl disulfides, isocyanates, aminooxy-, aldehyde, keto, chloroacetyl, bromoacetyl, and vinyl sulfones. Further exemplary functional groups and crosslinking methods and methods of conjugation using such functional groups are described in, e.g., Hermanson, "Bioconjugate Techniques" $2^{nd}$ Edition, Academic Press, 2008, the disclosure of which is incorporated herein by reference in its entirety.

Depending on the particular functional groups present, whether naturally occurring or synthetic, on the antigen or antibody-binding agent and the polynucleotide to be conjugated, in some instances, useful conjugation reagents may include but are not limited to e.g., homobifunctional conjugation reagents (e.g., (Bis(2-[Succinimidooxycarbonyloxy] ethyl) sulfone, 1,4-Di-(3'-[2'pyridyldithio]-propionamido) butane, Disuccinimidyl suberate, Disuccinimidyl tartrate, Sulfodisuccinimidyl tartrate, Dithiobis(succinimidyl propionate), 3,3'-Dithiobis(sulfosuccinimidyl propionate), Ethylene glycol bis(succinimidyl succinate), and the like), heterobifunctional conjugation reagents (e.g., m-Maleimidobenzoyl-N-hydroxysuccinimide ester, m-Maleimidobenzoyl-N-hydroxysulfosuccinimide ester, N-γ-Maleimidobutyryloxysuccinimide ester, N-γ-Maleimidobutyryloxysulfosuccinimide ester, N-(8-Maleimidocaproic acid) hydrazide, N-(ε-Maleimidocaproyloxy) succinimide ester, N-(8-Maleimidocaproyloxy) sulfo succinimide ester, N-(p-Maleimidophenyl) isocyanate, N-Succinimidyl(4-iodoacetyl)aminobenzoate, Succinimidyl 4-(N-maleimidomethyl) cyclohexane-1-carboxylate, Succinimidyl 4-(p-maleimidophenyl) butyrate, N-Sulfosuccinimidyl(4-iodoacetyl)aminobenzoate, Sulfosuccinimidyl 4-(N-maleimidomethyl) cyclohexane-1-carboxylate, Sulfo succinimidyl 4-(p-maleimidophenyl) butyrate, 1-Ethyl-3-(3-dimethylaminopropyl) carbodiimide hydrochloride, 1-Ethyl-3-(3-dimethylaminopropyl) carbodiimide hydrochloride, Maleimide PEG N-hydroxysuccinimide ester, and the like), photoreactive conjugation reagents (e.g., p-Azidobenzoyl Hydrazide, N-5-Azido-2-nitrobenzyloxysuccinimide, p-Azidophenyl glyoxal monohydrate, N-(4[p-Azidosalicylamido]butyl)-3'-(2'-pyridyldithio) propionamide, Bis (P[4-azidosalicylamido]-ethyl) disulfide, N-Hydroxysuccinimideyl-4-azidosalicyclic acid, N-Hydroxysulfosuccinimidyl-4-azidobenzoate, Sulfosuccinimidyl 2-(7-azido-4-methylcoumarin-3-acetamide)ethyl-1,3-dithiopropionate, Sulfosuccinimidyl 2-(m-azido-o-nitrobenzamido)-ethyl-1,3'-propionate, Sulfosuccinimidyl 6-(4'-azido-2'-nitrophenylamino)hexanoate, Sulfosuccinimidyl (4-azidophenyl dithio)propionate, Sulfosuccinimidyl-2-(p-azidosalicylamido)ethyl-1,3-dithiopropionate, and the like).

In instances where a polynucleotide is functionalized with a thiol functional group (e.g., a thiolated oligonucleotide), conjugation to an antigen or antibody-binding agent of interest may be achieved through the use of sulfo-sulfosuccinimidyl 4-(N-maleimidomethyl)cyclohexane-1-carboxylate (sulfo-SMCC) conjugation as described herein.

In instances where a polynucleotide is conjugated to a small molecule, any convenient method of conjugation may find use in covalently attaching the polynucleotide to the small molecule depending on various factors including e.g., available reactive groups on the small molecule and the presence or absence of particular modifications on the polynucleotide. In some instances, amine functionalized polynucleotide may be conjugated to a desired small molecule via an amine-reactive crosslinker including but not limited to e.g., NHS ester including e.g., as described herein.

In some instances, attachment of the polynucleotide to the antigen or antibody-binding agent utilizes existing functional moieties already present on the polynucleotide. In some instances, a functional moiety utilized in conjugating the polynucleotide to the antigen or antibody is added to a polynucleotide to generate a functionalized polynucleotide. Functionalized polynucleotides may be generated by modifying one or more nucleotides of the polynucleotide or by adding a modified nucleotide to the polynucleotide. Such modified nucleotides may, in some instances, be referred to as functionalized nucleotides.

Modified nucleotides may be introduced into the polynucleotide by any convenient method including but not limited to, e.g., synthetic/chemical synthesis (e.g., solid-phase oligonucleotide synthesis, phosphor amidite synthesis, etc.), recombinant synthesis, enzymatic incorporation, and the like. Modified nucleotides and nucleotide modifications useful in forming an attachment to an antigen of interest include but are not limited to, e.g., those useful in Click-Chemistry functionalization (e.g., azide-functionalized, alkyne-functionalized, dibenzocyclooctyne (DBCO) functionalized, etc.), those useful in nucleic acid labeling, those useful in photocrosslinking, those useful in acrylic phosphor amidite linking, those useful in pyrophosphate linking/ligation, and the like, such as, e.g., 3'-Azido-2',3'-dideoxyadenosine-5'-triphosphate, 5-(3-Azidopropyl)-uridine-5'-triphosphate, 5-Ethynyl-2'-uridine 5'-triphosphate, 8-Azido-adenosine-5'-triphosphate, $N^6$-(6-Azido)hexyl-3'-deoxyadenosine-5'-triphosphate, Cytidine-5'-phosphate-3'-(15-azido-4,7,10,13-tetraoxa-pentadecanoyl-6-aminohexyl) phosphate, γ-(2-Azidoethyl)-adenosine-5'-triphosphate, γ-(6-Azidohexyl)-adenosine-5'-triphosphate, γ-[(6-Azidohexyl)-imido]-adenosine-5'-triphosphate, $N^6$-(6-Azido)hexyl-adenosine-5'-triphosphate, $N^6$-(6-Azido)hexyl-2'-deoxy-adenosine-5'-triphosphate, $N^6$-(6-Azido)hexyl-3'-deoxyadenosine-5'-triphosphate, 3'-Azido-2',3'-dideoxythymidine-5'-triphosphate, 5-(15-Azido-4,7,10,13-tetraoxa-pentadecanoyl-aminoallyl)-2'-deoxyuridine-5'-triphosphate, $N^6$—Propargyl-adenosine-5'-triphosphate, adenosine-5'-[γ-(propargyl)]triphosphate, Adenosine-5'-[γ-(propargyl)-imido]triphosphate, 2-Ethynyl-adenosine-5'-triphosphate, 5-(Octa-1,7-diynyl)-2'-deoxycytidine 5'-triphosphate, 5-(Octa-1,7-diynyl)-2'-deoxyuridine 5'-triphosphate, 5-Ethynyl-2'-deoxyuridine 5'-triphosphate, 5-Dibenzylcyclooctyne-2'-deoxyuridine 5'-triphosphate, 2-Aminopurine-2'-deoxyriboside-Triphosphate, 5-Aminoallyl-2'-deoxycytidine-5'-Triphosphate, 5-Aminoallyl-2'-deoxyuridine-5'-Triphosphate, 5-Propargylamino-2'-deoxycytidine-5'-Triphosphate, 5-Propargylamino-2'-deoxyuridine-5'-Triphosphate, 5-Iodouridine-5'-Triphosphate, 4-Thiouridine-5'-Triphosphate, 5-Bromouridine-5'-Triphosphate, 5'-Acrydite modification, 5'-adenylation modification, and the like.

In some instances, attachment of a polynucleotide to an antigen or antibody-binding agent of interest is mediated by one or more functional linkers. A functional linker, as used herein, refers to any suitable linker that has one or more functional groups for the attachment of one molecule to another. For example, in some instances a nucleotide of a polynucleotide of the subject disclosure may be attached to a biomolecule linker that comprises a functional group (e.g., an amino functional group, a thiol functional group, a hydroxyl functional group, an imidazolyl functional group, a guanidinyl functional group, an alkyne functional group, an azide functional group, a strained alkyne functional group, etc.). As a non-limiting example, a nucleotide of a polynucleotide of the subject disclosure may biotinylated with functional biotin that comprises a functional group.

In some instances, those modified nucleotides useful in attachment of a polynucleotide to a desired antigen or antibody-binding agent may include those available from commercial suppliers, including but not limited to, e.g., Integrated DNA Technologies, Inc. (Coralville, Iowa), Tri-Link BioTechnologies, Inc. (San Diego, Calif.), Jena Bioscience GmbH (Jena, Germany), Life Technologies, Inc. (Grand Island, N.Y.), New England Biolabs, Inc. (Ipswich, Mass.), Zymo Research Corporation, (Irvine, Calif.), Enzo Life Sciences, Inc. (Farmingdale, N.Y.), and the like.

Generation of the antigen-DNA conjugates and antibody-binding agent-DNA conjugates of the instant disclosure may take into account the efficiency of the conjugation reaction, which influences the molar ratio of antigen to polynucleotide, e.g., antigen:DNA or antibody-binding agent to polynucleotide, e.g., antibody, antibody mimetic, or aptamer:DNA molar ratio, following conjugation. The inventors of the instant disclosure have discovered that the molar ratio of antigen to polynucleotide impacts agglutination in the described assay. Without being bound by theory, low antigen or antibody to high polynucleotide ratios appear, in some instances, to inhibit agglutination (e.g., by inhibiting access of the binding surfaces of the antigen and the antibody). In many instances, the antigen-to-polynucleotide or antibody-to-polynucleotide molar ratio following conjugation will be greater than 1:5, including but not limited to e.g., greater than 1:4, greater than 1:3, greater than 1:2, etc. In certain instances, the antigen-to-polynucleotide molar ratio following conjugation will range from 1:1 to 1:5 including but not limited to e.g., 1:1 to 1:4, 1:1 to 1:3, 1:1 to 1:2, etc. In other instances, the molar ratio of antigen-to-polynucleotide or antibody-to-polynucleotide following conjugation, for use in an assay as described, is essentially 1:1, essentially 1:2, essentially 1:3, and the like.

The instant disclosure also provides devices related to the subject assays and detection of the described antibodies. Such devices may include, but are not limited to "field-use" devices, e.g., dipstick assay devices, lateral-flow assay devices, slide-based devices, and the like, that may allow performing the herein described agglutination assays with minimal or no laboratory amenities, such as, e.g., electricity, chemical reagents, temperature control, refrigeration, etc. Also included are devices for use in the laboratory setting, e.g., those devices utilizing precise quantification of the produced amplification product, including, e.g., PCR devices, qPCR devices, fluorimeters, scintillation counters, microscopes, plate-readers, nucleic acid sequencing devices, etc. In some instances, isothermal amplification devices, such as those described in Cheng et al. (2012) Sensors 12, 8319-8337, the disclosure of which is incorporated herein by reference in its entirety, may be modified for use as devices for practicing the methods as described herein.

In yet another aspect, the present disclosure provides kits for practicing the subject methods, e.g., as described above. The subject kits may include any combination of the herein described reagents, devices, or compositions useful in practicing the methods as described above including but not limited to, e.g., one or more of the described antigen-DNA conjugates, antibody-binding agent-DNA conjugates, bridging polynucleotides, splint polynucleotides, enzymatic reagents (e.g., ligases), primers, and the like. Subject kits may further include one or more reagent preparation reagents including but not limited to, e.g., reagents for functionalizing an antigen or antibody-binding agent (including e.g., functionalized polynucleotides for readily conjugating the polynucleotide to an antigen or antibody-binding agent of interest), reagents for functionalizing a polynucleotide (e.g., a functionalized nucleotide (i.e., a nucleotide that includes one or more reactive groups), reagents for conjugation of a polynucleotide and/or an antigen and/or antibody-binding agent (including e.g., one or more conjugation and/or crosslinking reagents or linkers as described herein).

In addition, subject kits may further include assay reagents or reagents useful in performing an assay of a sample, e.g., a patient sample, to allow for an assessment, e.g., of whether one or more antibody isotypes are present in a sample from the subject. Such assay reagents may include but are not limited to, e.g., detection reagents, sample preparation reagents, amplification reagents (e.g., PCR reagents and/or isothermal amplification reagents and/or qPCR reagents, etc.) and agglutination reagents (e.g., antigen-DNA conjugates, antibody-binding agent-DNA conjugates, and the like), buffers, diluents, etc. Such assay kits may further include sample collection components, e.g., sample collection containers and/or sample collection devices, etc. The above components may be present in separate containers or one or more components may be combined into a single container, e.g., a glass or plastic vial or tube.

Kits may further include control reagents and samples including but not limited to, e.g., control samples (e.g., positive control samples, negative control samples, etc.) calibration reagents (e.g., fluorescent calibration reagents, etc.).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, Blu-ray, removable drive (e.g., flash memory device), etc., on which the information has been recorded. Yet another means that may be present is a website address which may be used via the internet to access the information at a removed site. Any convenient means may be present in the kits.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Isotype-Specific Antibody Detection by Agglutination-PCR (ISAP)

Overview of the ISAP Method

FIG. 1 illustrates the ISAP method for detection of a target antibody. An antibody-binding agent-DNA conjugate and an antigen-DNA conjugate are incubated with a sample comprising the target antibody analyte. The secondary antibody-DNA conjugate binds to the target antibody, which, in turn, binds to the antigen-DNA conjugate to form a complex in which the secondary antibody-DNA and antigen-DNA are brought in proximity to each other. Because of their proximity, the secondary antibody-DNA and antigen-DNA can be ligated in the presence of a bridge oligonucleotide. The ligation product can be detected and quantified by qPCR or any other DNA detection methodology (e.g., DNA microarray).

The ISAP method can be used in principle to detect antibodies of any isotype including IgE, IgM, IgG, IgA and IgD. Moreover, the ISAP method can be used to detect two or more different isotypes in a single assay by adding corresponding secondary antibody-DNA conjugates into the system. For example, one or more of the following secondary antibody-DNA conjugates may be used: an anti-IgE secondary antibody-DNA conjugate for detection of IgE, an anti-IgM secondary antibody-DNA conjugate for detection of IgM, an anti-IgG secondary antibody-DNA conjugate for detection of IgG, an anti-IgA secondary antibody-DNA conjugate for detection of IgA, and an anti-IgD secondary antibody DNA conjugate for detection of IgD.

Methods

Analysis of Plasma Samples

Plasma samples from patients with peanut allergy were obtained as part of their enrollment into an institutional review board-approved clinical trial of oral immunotherapy (OIT) in children and adults with peanut allergy (POISED; ClinicalTrials.gov Identifier: NCT02103270). Peanut allergy was defined as having a reaction to a double-blind, placebo-controlled food challenge to peanut (with reactions elicited with ≤500 mg of peanut protein) and a positive skin prick test response to peanut (≥5 mm).

OVA Sensitization

Sensitization of mice was achieved by administration of ovalbumin (OVA) with aluminum hydroxide (alum) followed by intranasal challenge with OVA. The protocol was performed as described (Bernstein et al. (2008) Ann Allergy Asthma Immunol. 100:S1-148, herein incorporated by reference), with minor modifications. Briefly, mice (n=5/group) were immunized intraperitoneally with 20 µg OVA (Grade V; Sigma-Aldrich, St Louis, Mo.) emulsified in 2.25 mg alum (AlumImuject; Pierce, Rockford, Ill.) in a total volume of 100 µL on days 0 and 14. Control mice (n=5) were inoculated similarly, but without OVA. Mice then were challenged intranasally on day 21 with a 20 µL solution containing 200 µg OVA in PBS or PBS alone. Body temperature changes were measured continuously for 2 hours after challenge. Successful sensitization is defined by the detection of a marked drop in body temperature (>3° C.) after OVA challenge. Serum samples were collected via retro-orbital bleeding on days 0, 7, and 14. On day 21, mice were sacrificed by inhalation of $CO_2$ and serum samples were collected from the heart. All serum samples were stored at −80° C. until used. Whole blood samples were collected alongside serum samples. Whole blood samples were diluted 1:1 in 10 mM EDTA and 1×PBS right after collection to prevent clotting. Whole blood samples were stored at −80° C. until used.

Sensitization with Peanut Oil

BALB/c wild type mice (n=10), C57BL/6 wild type mice (n=10), BALB/c-Jh knockout mice (n=5) and BALB/c-RAG knockout mice (n=5) were epicutaneously sensitized with peanut oil (200 μL, Golden Peanut Company, Dawson, Ga.) for 6 weeks. BALB/c and C57BL/6 mice were then challenged intraperitoneally with 5 mg of peanut protein (extracted from defatted peanut flour as previously described (Byrd Mill, Ashland, Va.). Body temperature was measured as described above to confirm sensitization. Serum samples were collected on day 0 via retro-orbital bleeding and on day 45 via heart bleeding after sacrificing the mice by inhalation of $CO_2$. Serum samples were stored at −80° C. until used.

ELISA Analysis

Specific IgE (sIgE) ELISA was performed as described (Bernstein et al., supra) Briefly, OVA was deposited on ELISA plates to capture and detect anti-OVA IgE from purified IgE samples and serum samples from OVA-sensitized mice. The quantity of surface-bound IgE was quantified by detecting absorbance after treatment with secondary anti-mouse IgE and SA-HRP. For the detection of peanut-specific IgE, peanut extract was coated on ELISA plates and anti-peanut IgE was detected as described above.

ImmunoCAP Analysis

ImmunoCAP analysis was performed by Phadia, Thermo Fischer.

DNA Sequence Design

DNA sequences and primers were provided from Enable Biosciences. The sequences were optimized to minimize the formation of secondary structure and primer dimers while maximizing amplification efficiency.

The sequences used in ISAP, including DNA molecules in antibody-DNA or antigen-DNA conjugates, a bridge oligonucleotide, and PCR primers are shown below:

```
1A:
                                       (SEQ ID NO: 1)
5'-CAGGTAGTAGTACGTCTGTTTCACGATGAGACTGGATGAA-3'

1B:
                                       (SEQ ID NO: 2)
5'-TCACGGTAGCATAAGGTGCAAGATAATACTCTCGCAGCAC-3'

Reverse primer 1:
                                       (SEQ ID NO: 3)
GTGCTGCGAGAGTATTATCT Forward primer 1:
                                       (SEQ ID NO: 4)
CAGGTAGTAGTACGTCTGTT 2A:
                                       (SEQ ID NO: 5)
5'-GGCCTCCTCCAATTAAAGAATCACGATGAGACTGGATGAA-3'

2B:
                                       (SEQ ID NO: 6)
5'-TCACGGTAGCATAAGGTGCAGTACCCAAATAACGGTTCAC-3'

Reverse primer 2:
                                       (SEQ ID NO: 7)
GTGAACCGTTATTTGGGTAC Forward primer 2:
                                       (SEQ ID NO: 8)
GGCCTCCTCCAATTAAAGAA 3A:
                                       (SEQ ID NO: 9)
GGATCACTCCAACTAGACTATCACGATGAGACTGGATGAA 3B:
                                       (SEQ ID NO: 10)
TCACGGTAGCATAAGGTGCAGTTATATCTGCCACTGTCAC Reverse primer 3:
                                       (SEQ ID NO: 11)
GTGACAGTGGCAGATATAAC Forward primer 3:
                                       (SEQ ID NO: 12)
GGATCACTCCAACTAGACTA 4A:
                                       (SEQ ID NO: 13)
AGAGTCCACTTCCCATAATGTCACGATGAGACTGGATGAA 4B:
                                       (SEQ ID NO: 14)
TCACGGTAGCATAAGGTGCACGGTACTGTCAGCATAGTTC Reverse primer 4:
                                       (SEQ ID NO: 15)
GAACTATGCTGACAGTACCG Forward primer 4:
                                       (SEQ ID NO: 16)
AGAGTCCACTTCCCATAATG 5A:
                                       (SEQ ID NO: 17)
CTACGACTAGGAGATAGATGTCACGATGAGACTGGATGAA 5B:
                                       (SEQ ID NO: 18)
TCACGGTAGCATAAGGTGCAGTTATGTATAGTACGCTCGC Reverse primer 5:
                                       (SEQ ID NO: 19)
GCGAGCGTACTATACATAAC Forward primer 5:
                                       (SEQ ID NO: 20)
CTACGACTAGGAGATAGATG Bridge oligo:
                                       (SEQ ID NO: 21)
CTACCGTGATTCATCCAG
```

Figure 2:
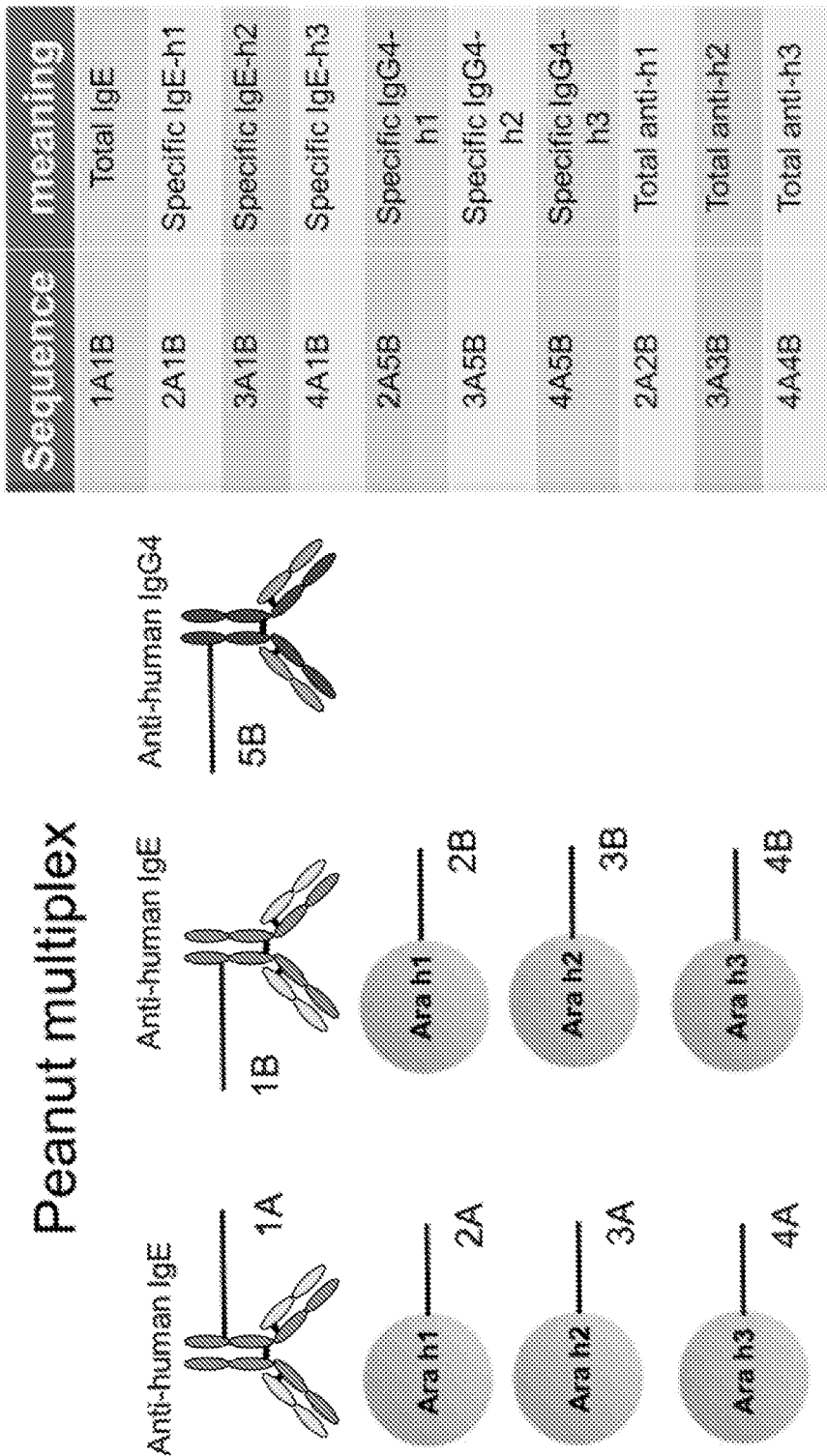
FIG. 2 shows that the ISAP method can be used in principle to detect antibodies of any isotype, including IgE, IgM, IgG, IgA and IgD, and may also be used to detect two or more different isotypes in a single assay by adding corresponding secondary antibody-DNA conjugates into the system. The table (at right) lists compositions capable of detecting IgG4 and IgE anti-peanut antigens antibodies in a single assay.
Figure 3A:
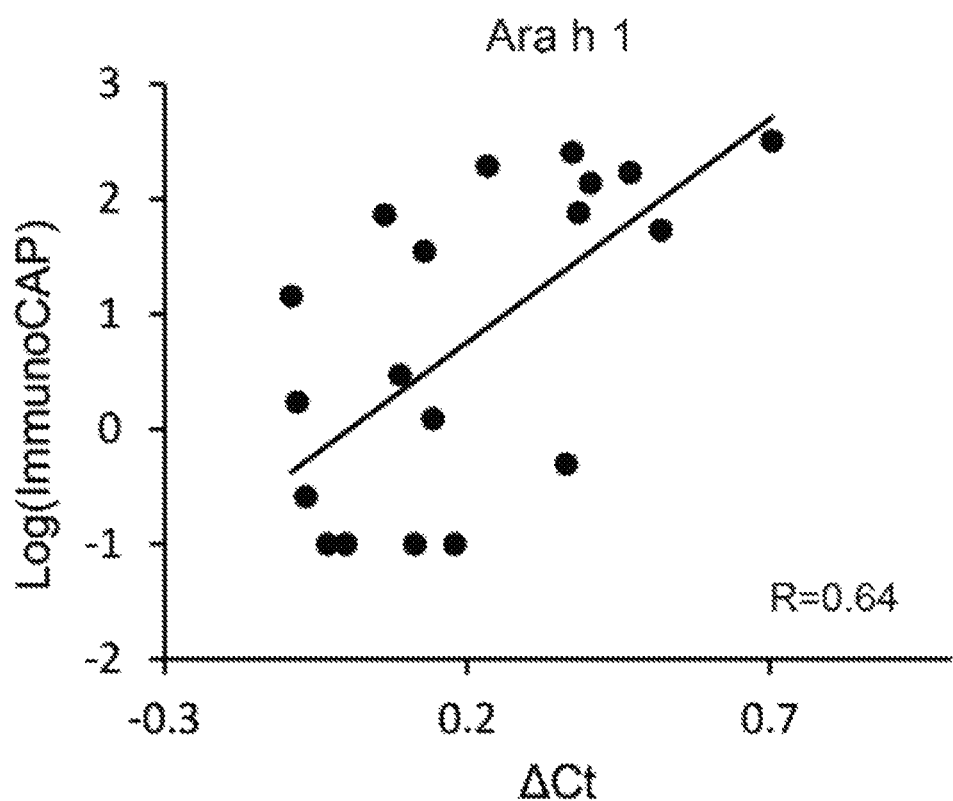
FIGS. 3A-3C show that the ISAP method can be used to detect IgE antibodies against peanut antigens Ara h1 (FIG. 3A), Ara h2 (FIG. 3B), and Ara h3 (FIG. 3C). The results correlate well with current gold standard use in the clinic (ImmunoCAP).
Figure 3B:
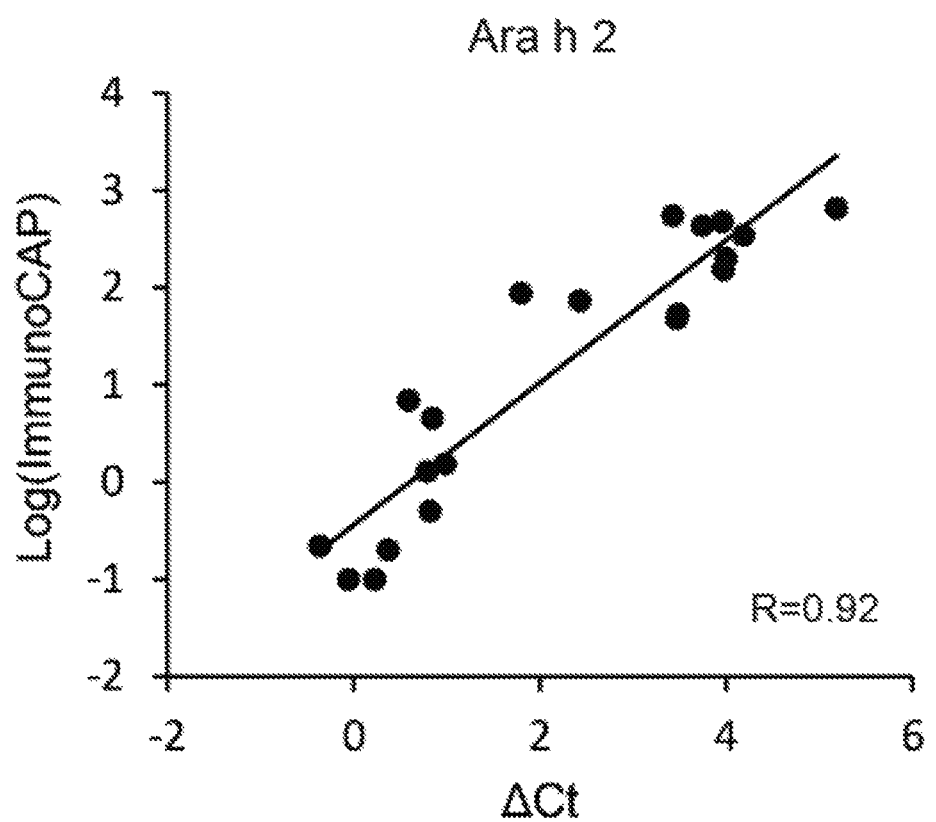
Figure 3C:
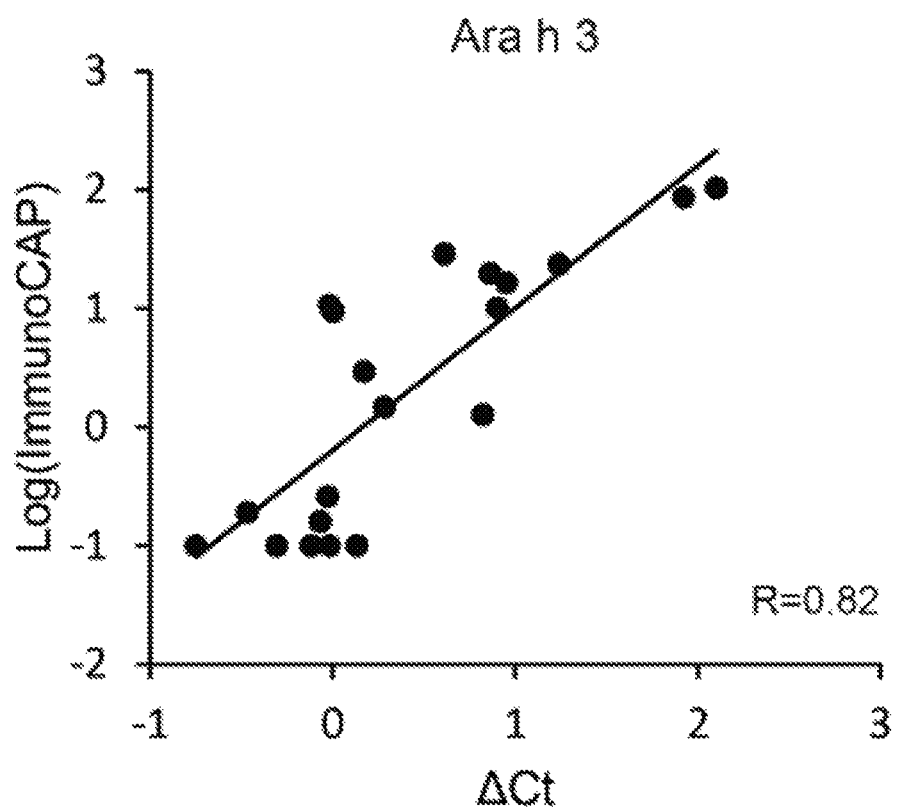

FIG. 2 illustrates how these sequences were used to detect IgG4 and IgE anti-peanut antibodies against Ara-h1, Ara-h2, and Ara-h3 antigens in a single assay using ISAP.

Synthesis of Allergen-DNA and Antibody-DNA Conjugates

Figure 4:
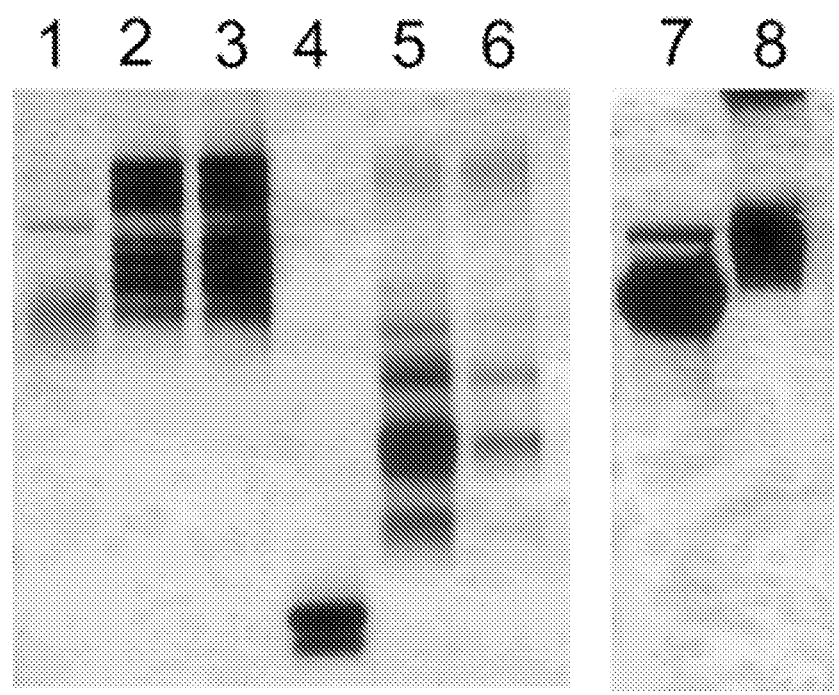
FIG. 4 shows representative silver staining of allergen-DNA and antibody-DNA conjugates. DNA conjugated allergen or antibodies have a higher mass than their unconjugated counterparts.
Figure 5:
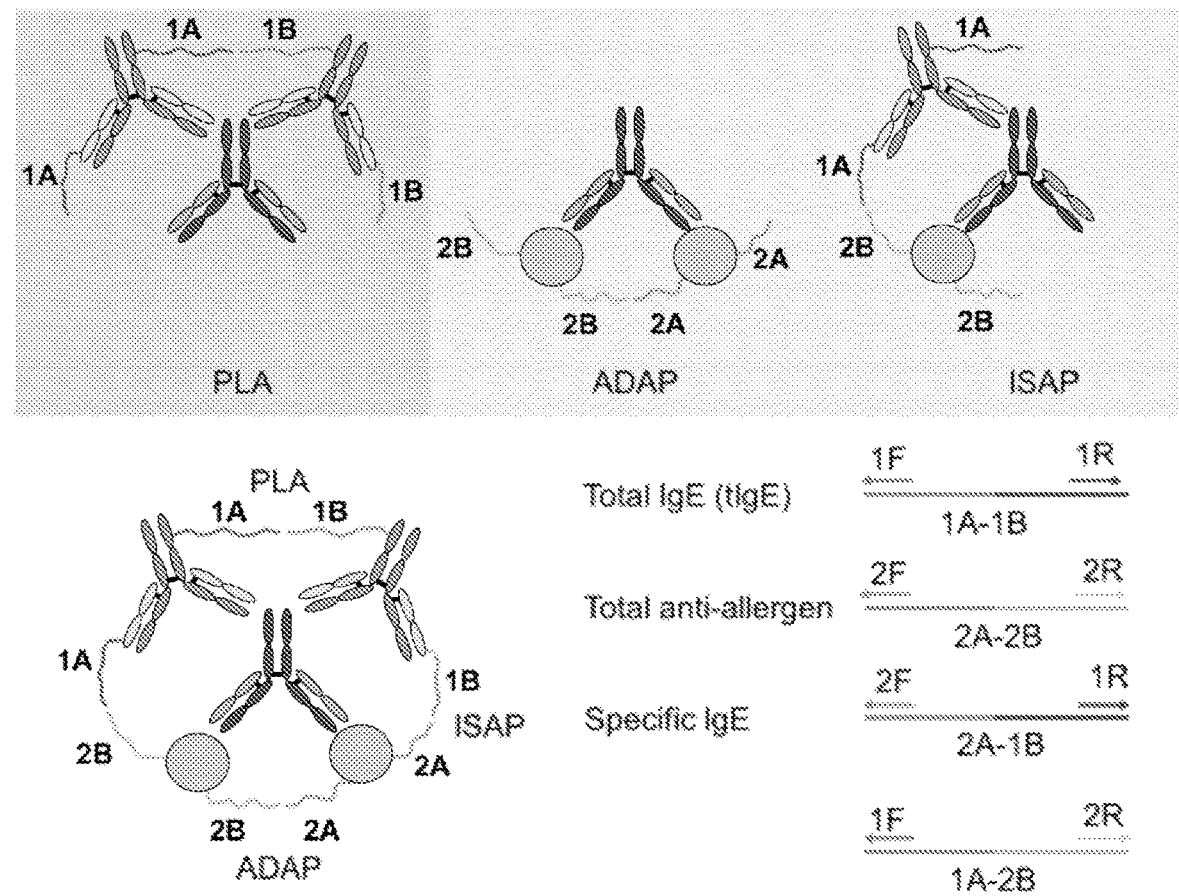
FIG. 5 shows an overview of PCR-based allergy assays, including a proximity ligation assay (PLA), which is a PCR-based method for protein detection, an antibody detection by agglutination-PCR (ADAP), which detects antigen-specific immunoglobulins of all subtypes (IgG, IgM, IgA, IgE, IgD), and isotype-specific agglutination-PCR (ISAP), which detects antigen-specific immunoglobulins of a particular isotype.
Figure 6A:
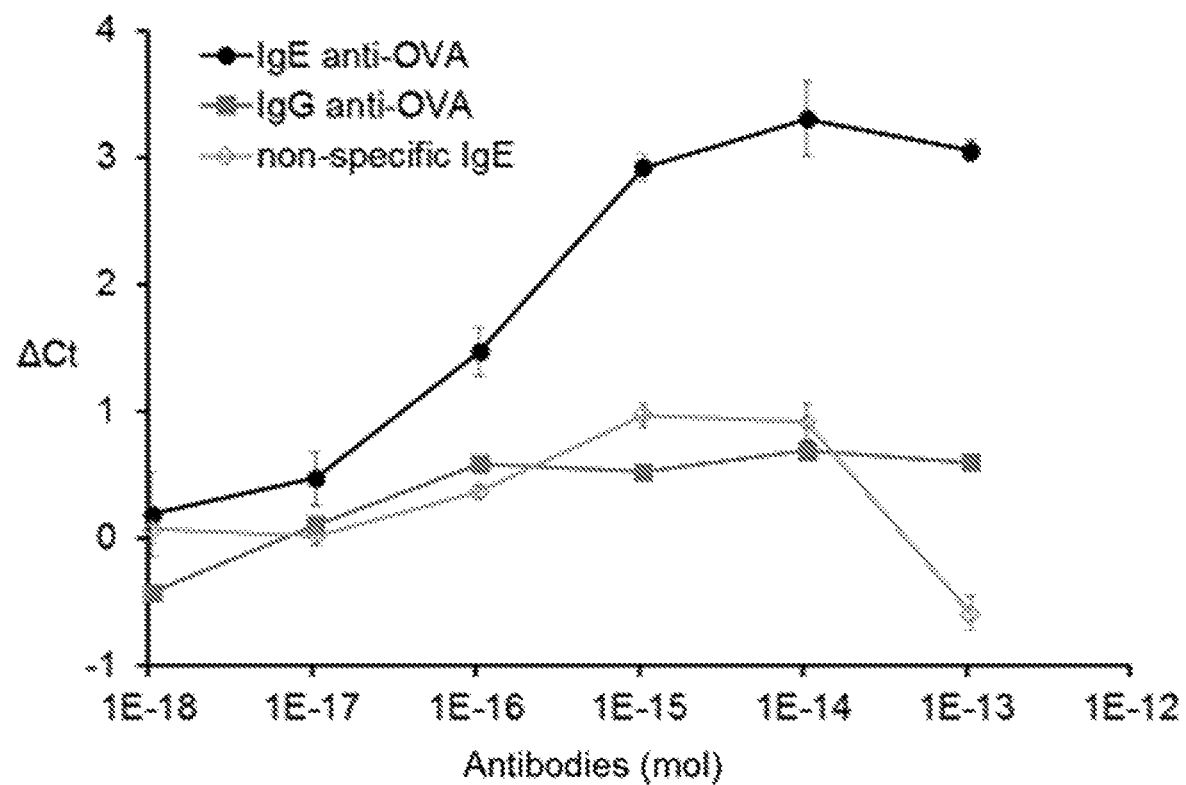
FIGS. 6A and 6B show that ISAP detects purified antibodies in buffer and outperforms ELISA.
Figure 6B:
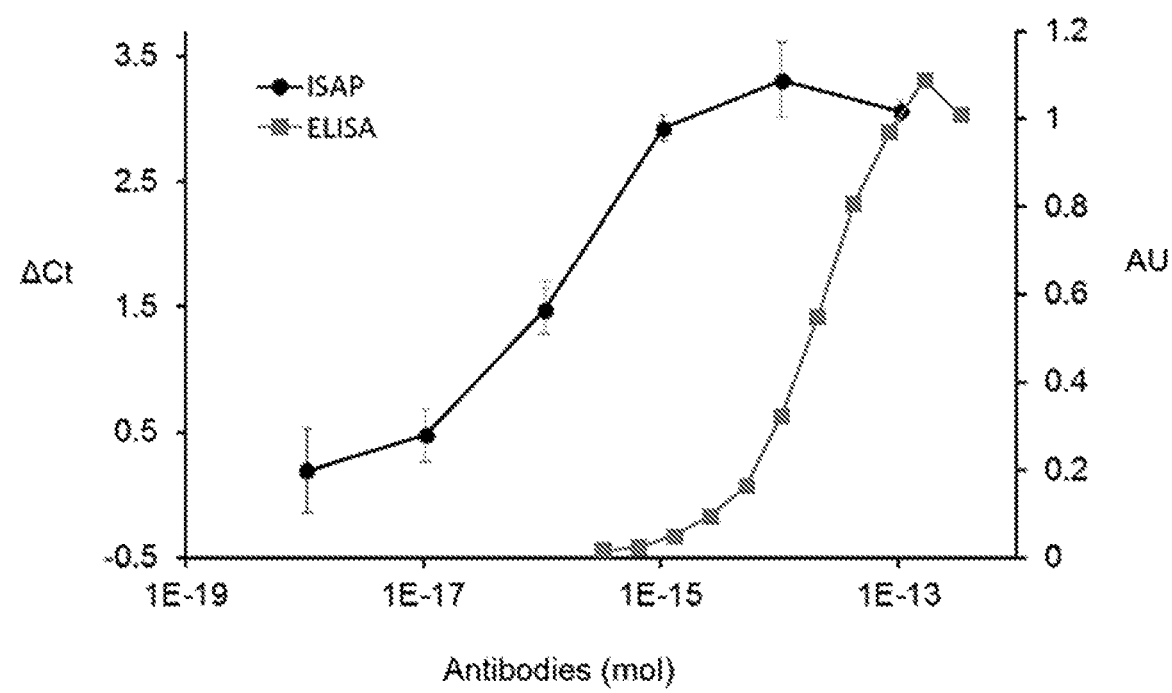
Figure 7A:
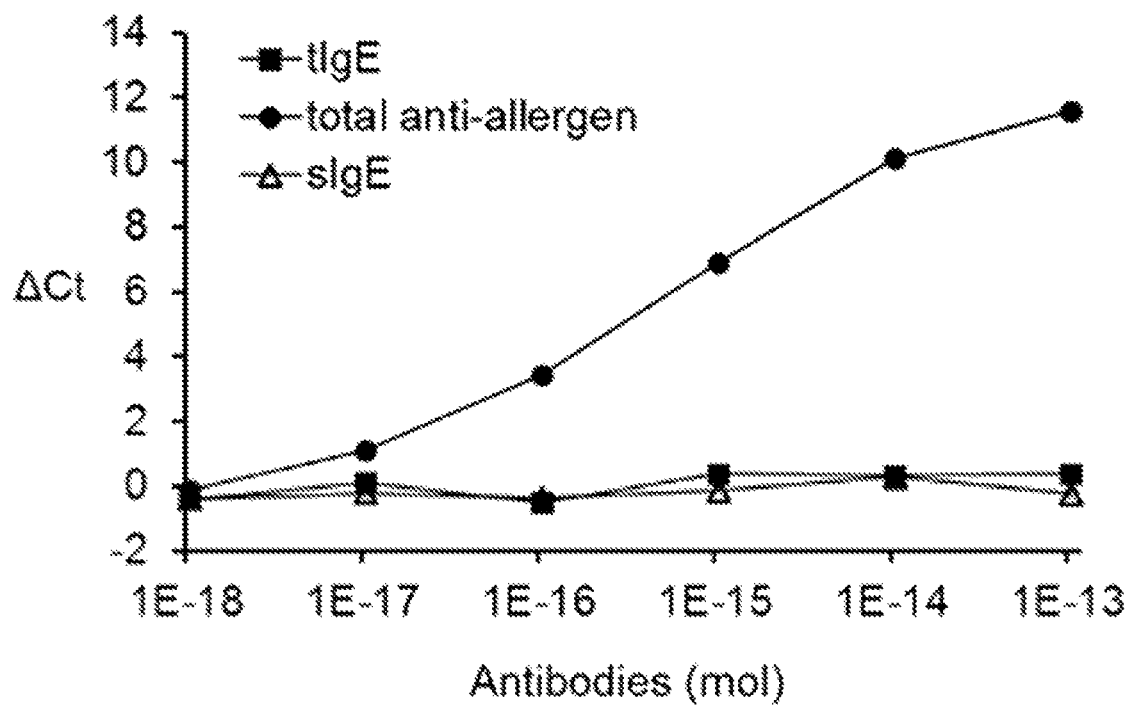
FIGS. 7A-7C show that the integrated PCR-based assays detect allergy markers with minimum cross-talk. In this assay, we detect total IgE (tIgE), total anti-allergen and specific IgE (sIgE) multiplexedly. The specificity of the integrated assay is assessed by dilution series of (FIG. 7A), anti-OVA IgG, (FIG. 7B) non-specific IgE, and (FIG. 7C) anti-OVA IgE respectively.
Figure 7B:
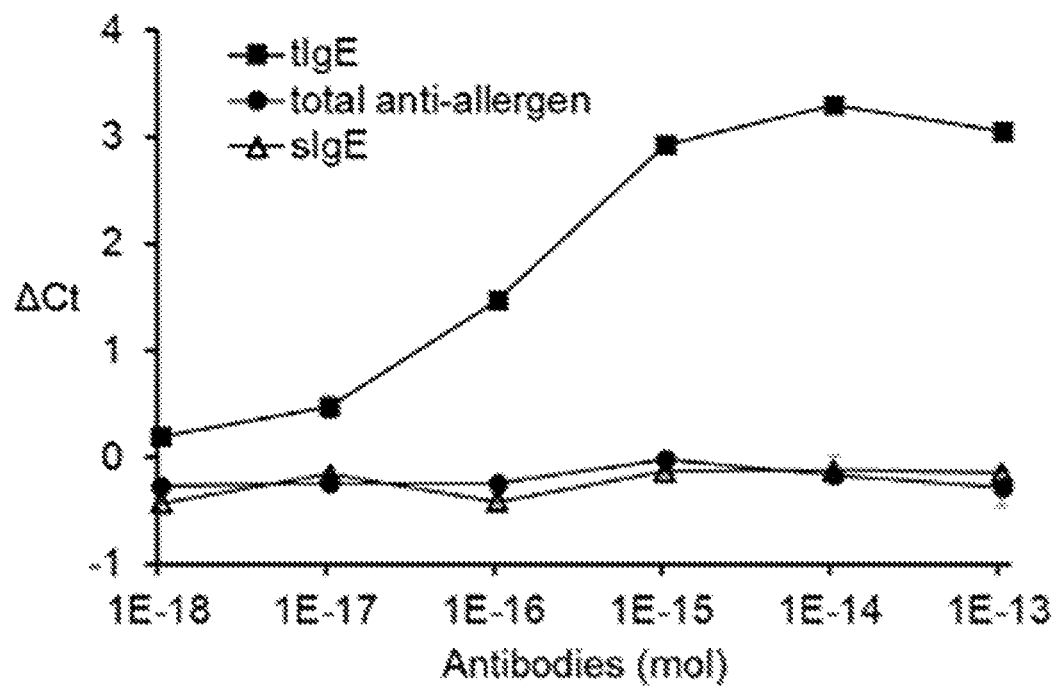
Figure 7C:
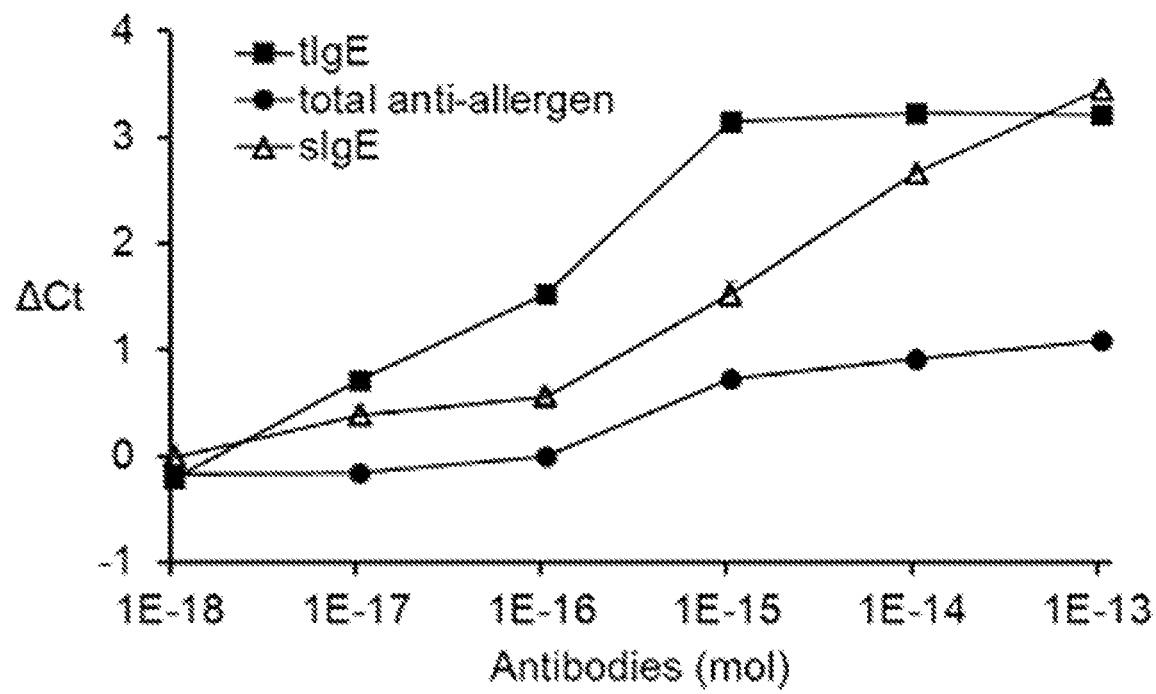
Figure 8A:
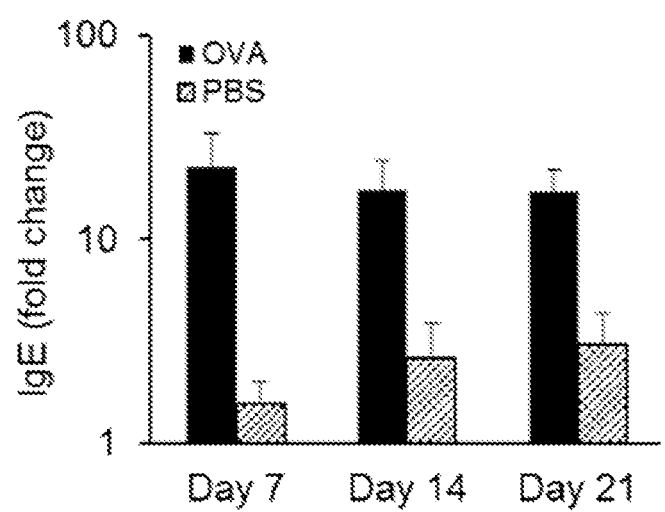
FIGS. 8A-8E show an integrated PCR-based analysis of serum from ovalbumin (OVA)-sensitized mice. Serum was collected from OVA-sensitized and control mice on day 0, 7, 14 and 21. The PCR signal is normalized to day 0 for each mouse.
Figure 8B:
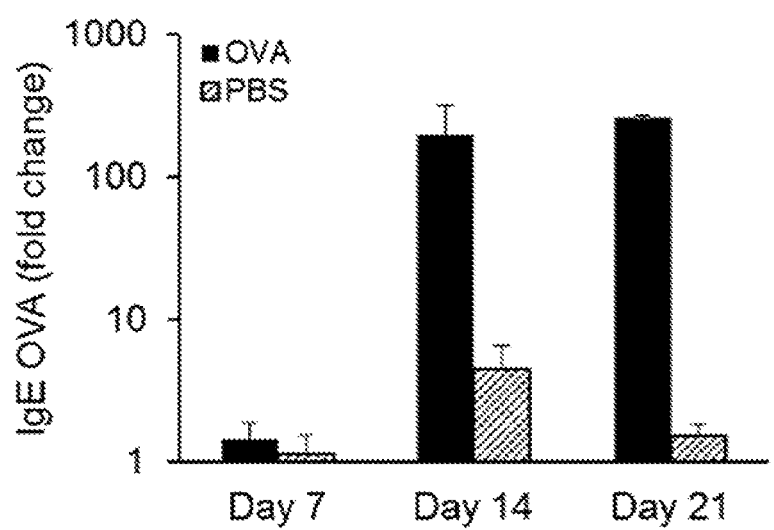
Figure 8C:
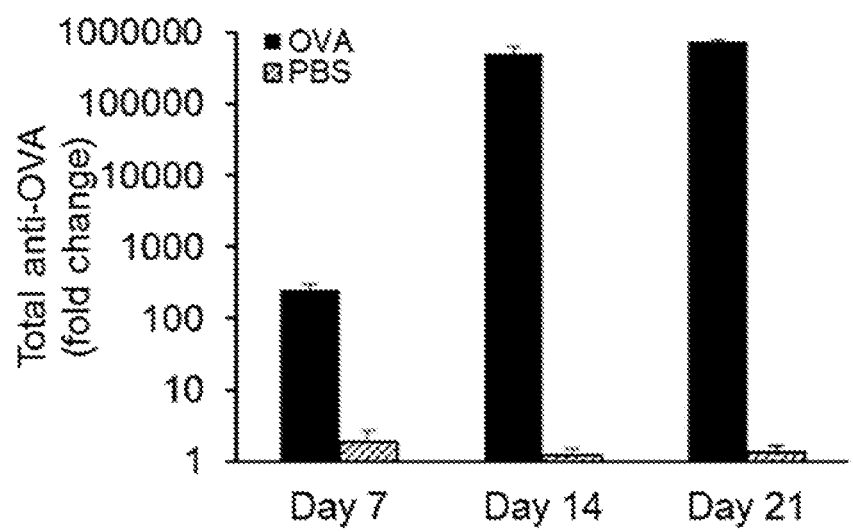
Figure 8D:
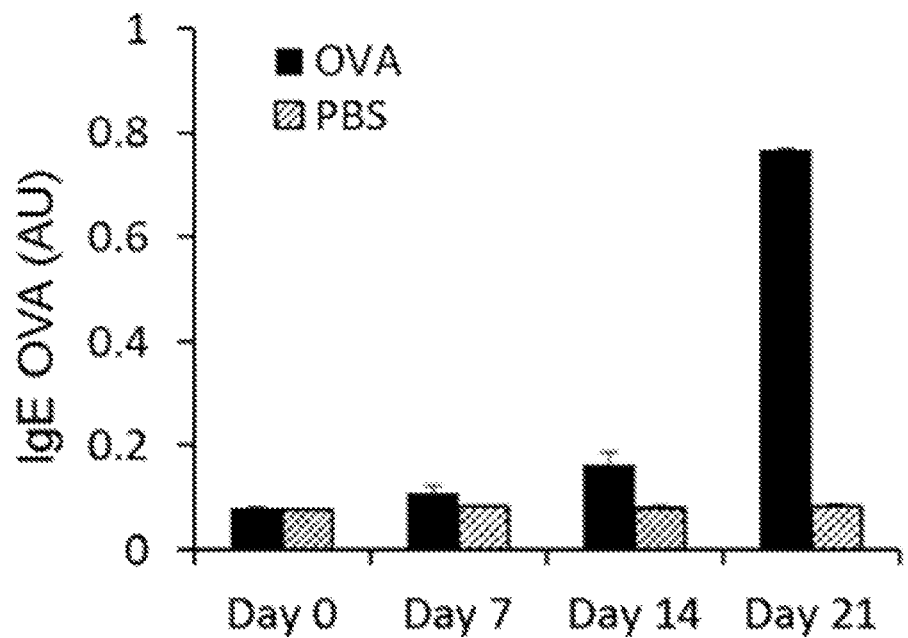
Figure 8E:
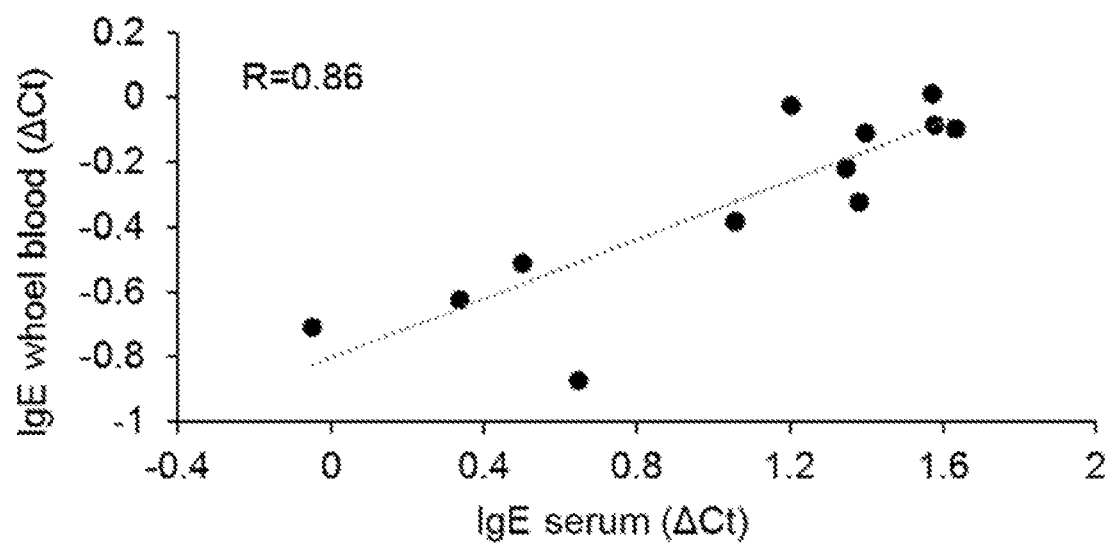
Figure 9A:
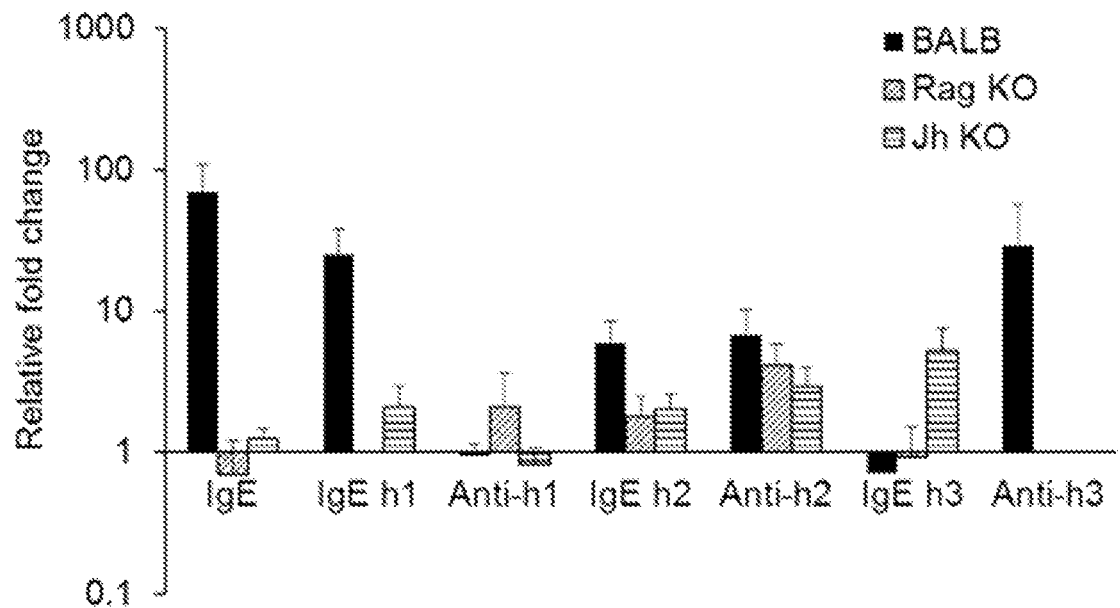
FIGS. 9A and 9B show PCR-based analysis of serum from peanut-sensitized mice.
Figure 9B:
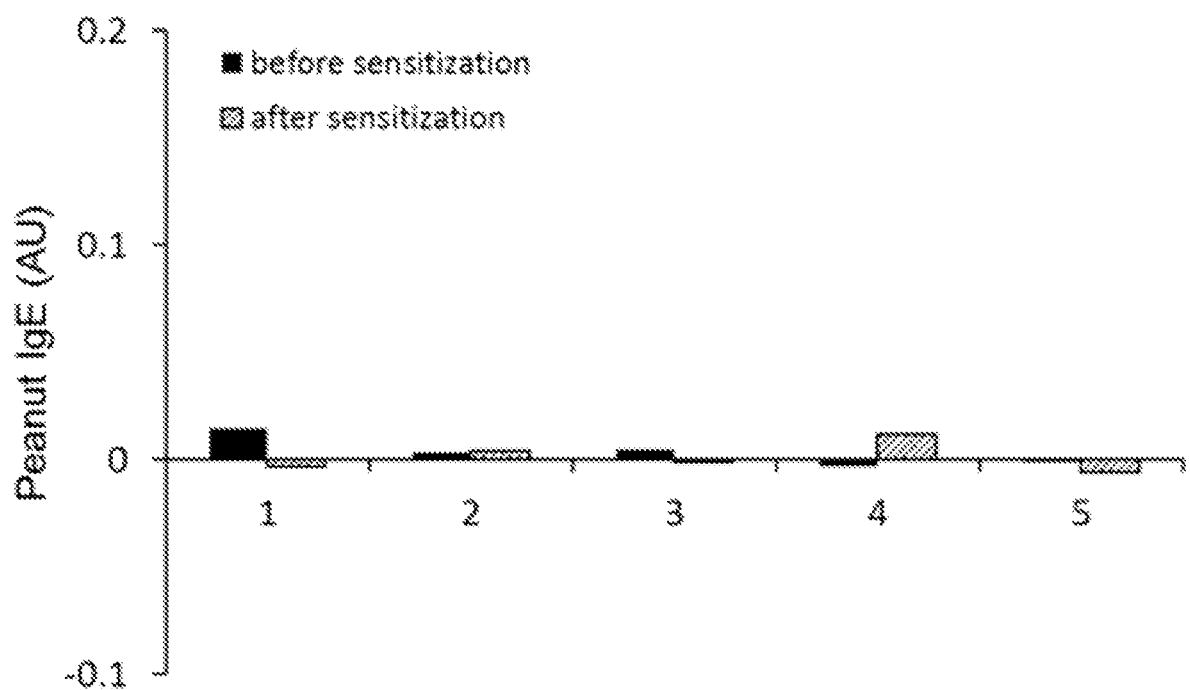
Figure 10A:
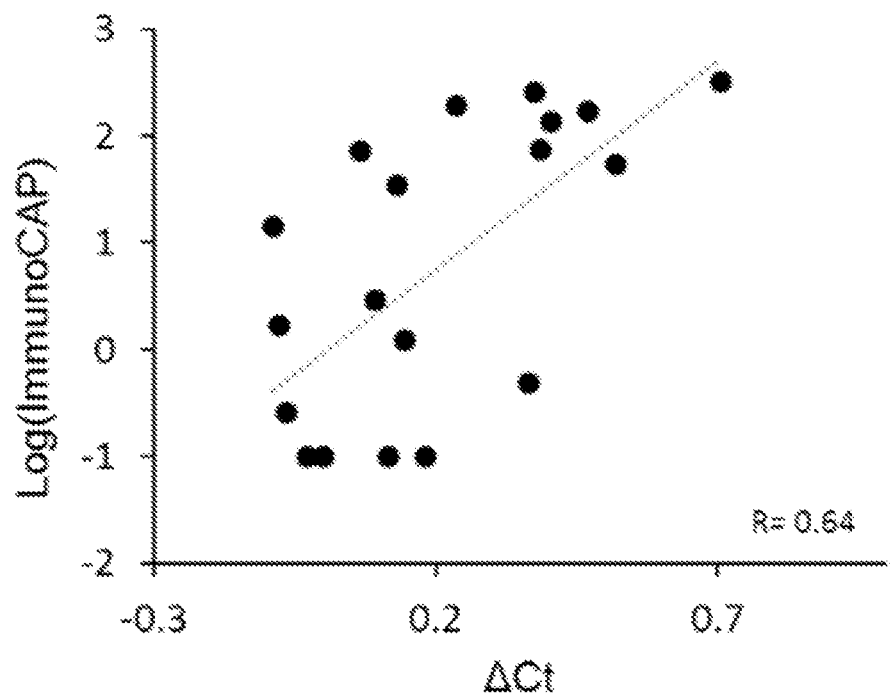
Figure 10B:
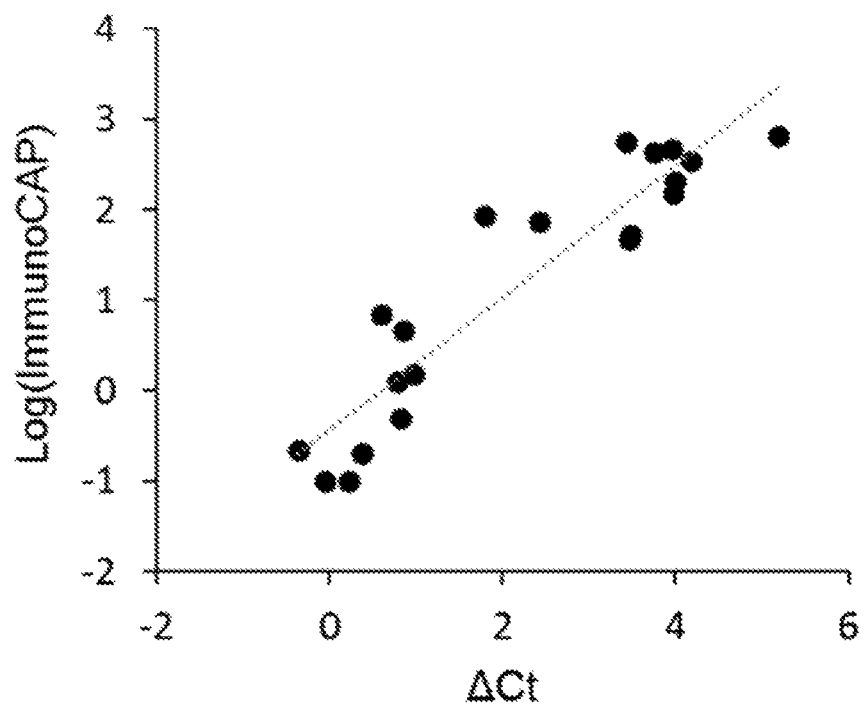
Figure 10C:
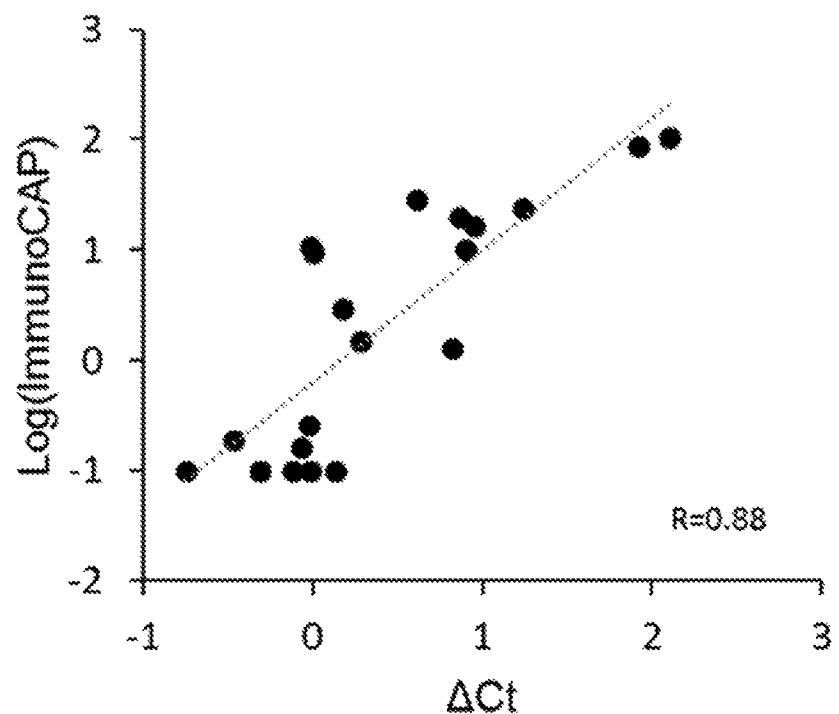
Figure 10D:
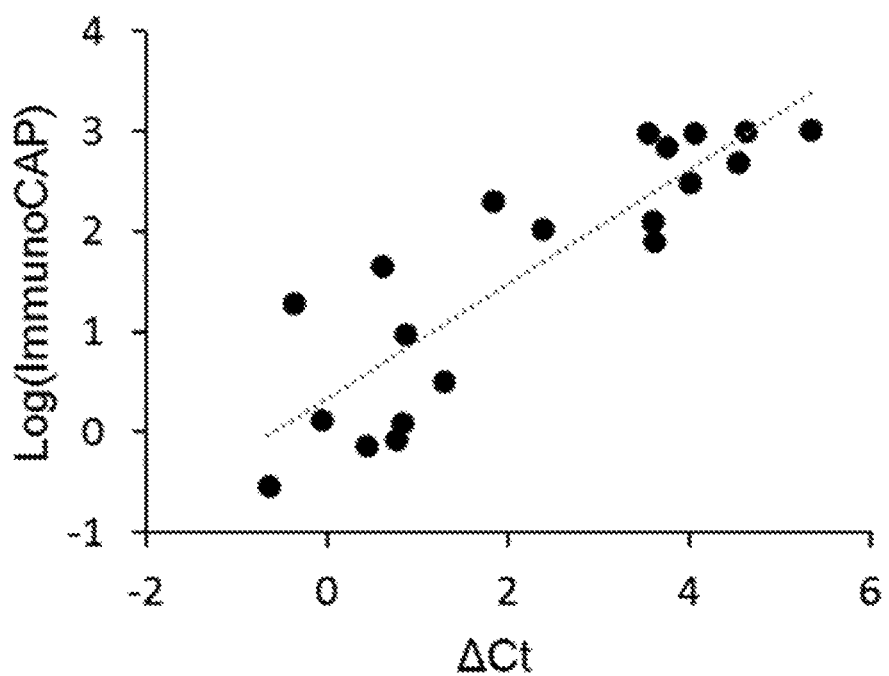

OVA was obtained from Life Technologies (#77120). Ara-h1 (#LTN-AH1-1), Ara-h2 (#RP-AH2-1) and Ara-h3 (#NA-AH3-1) were purchased from Indoor Technologies. Allergen (OVA, Ara-h1, Ara-h2 and Ara-h3)-DNA conjugates were synthesized by resuspending recombinant protein Reaction Buffer (1 mg/mL protein in 55 mM sodium phosphate, 150 mM sodium chloride, 20 mM EDTA, pH 7.2). SMCC (succinimidyl 4-(N-maleimidomethyl)cyclohexane-1-carboxylate, Pierce Biotechnologies) was dissolved in anhydrous DMSO and 5 μL of a 4 mM solution was added to 50 μL of the protein solution and incubated at RT for 2 hours. Thiolated-DNA (IDT) was resuspended to 100 μM in Reaction Buffer and 3 μL was added to 50 μL of Reaction Buffer. To this solution, 4 μL of a 100 mM solution of DTT (Life Technologies) was added to reduce the oxidized thiol-DNA. The solution was then incubated at 37° C. for 1 hour. 7k MWCO (molecular weight cut-off) gel microspin columns (Life Technologies) were equilibrated to Reaction Buffer. The reduced oligonucleotides were twice desalted by the equilibrated microspin columns. Unreacted SMCC was removed from the allergen protein solution by diluting to 500 μL volume in Reaction Buffer. The thiol-DNA and allergen-SMCC solutions were then mixed and reacted overnight at 4° C. and then purified by 30k MWCO filter column (Millipore). Concentrations of the conjugates were determined by BCA assay (Life Technologies). Conjugation efficiencies were determined by SDS-PAGE and silver staining as described previously. Representative silver-stains are provided (FIG. 4). DNA-to-allergen ratios of the conjugates were estimated by UV-VIS absorption. Allergen-DNA conjugates were stored at 4° C. for short-term usage or aliquoted for long-term storage at −80° C.

Antibody-DNA conjugates were synthesized following a similar protocol, but with minor modifications. Briefly, anti-IgE and anti-IgG4 polyclonal antibodies were purchased from Sigma and Thermo Fischer. Instead of 30K MWCO filters, 100K MWCO filter columns were used to purify the conjugates from unreacted DNA.

Isotype-Specific Agglutination-PCR (ISAP)

For detecting allergen-specific IgE, 1 fmol of allergen-DNA conjugate and anti-IgE conjugates were resuspended in 2 μL of Incubation Buffer C (2% BSA, 0.2% Triton X-100, 8 mM EDTA in PBS). To this solution, 1 μL of analyte was added and then incubated at 37° C. for 30 minutes. After incubation, 117 μL of ligation mix (20 mM Tris, 50 mM KCl, 20 mM $MgCl_2$, 20 mM DTT, 25 μM NAD, 0.025 U/μl ligase, bridge oligo 100 nM, 0.001% BSA, pH=7.5) was added, and then incubated for 15 min at 30° C. After this incubation step, 25 μL of the solution was added to 25 μL 2× PCR Master Mix (Qiagen) with 10 nM primers and then amplified by PCR (95° C. for 10 min, 60° C. for 30 s, 95° C. for 15 s, 13 cycles). The PCR reaction was then diluted 1:20 in $ddH_2O$ and 8.5 μL of the diluted PCR samples were added to 10 μL 2× qPCR Master Mix (Life Technologies) with 1.5 μL primers (final concentration 690 nM). Analysis by qPCR was performed on Bio-Rad CFX96 real-time PCR detection system.

For the detection of allergen-specific IgG4, the procedure was similar with the exception that anti-IgG4-DNA conjugates were used in lieu of anti-IgE-DNA conjugates.

Data Analysis

All PCR assays were run alongside a Buffer C-only blank (2% BSA, 0.2% Triton X-100, 8 mM EDTA in PBS) to correct run-to-run variations. The Ct value for each sample was determined by a single-threshold fluorescence value automatically chosen by the Bio-Rad software. For each sample, the PCR cycle number with a fluorescence value corresponding to the threshold value was defined as the cycle threshold (Ct) value. ΔCt is defined as the Ct value of the blank minus the Ct value of the samples. The value of ΔCt is proportional to the initial amplicon concentration in the PCR plate well. This amplicon concentration is then also proportional to the amount of target antibody.

To determine the detection limit, a non-linear four-parameter logistic fit for an antibody dilution series is determined using custom software. The limit of detection for PCR-based assay is defined as the average ΔCt value of the buffer C-only blank plus 3 standard deviations of the blank. The value of limit of detection is calculated relative to the blank. A similar process was performed for dilution series of antibodies measured by ELISA to obtain the corresponding detection limit.

For tests of specimens from mice undergoing OVA or peanut sensitization, we normalized the PCR-based signal by the signal observed at day 0. We empirically observed that such normalization helps to correct for heterogeneity between mice.

For statistical analysis, Mann-Whitney U tests were performed. We considered a P value smaller than 0.05 to be statistically significant.

Example 2

Ultrasensitive Multiplex Detection of Allergic Responses by PCR

Here we demonstrate a highly sensitive and multiplexable component-resolved allergy diagnostic with an integrated PCR-based approach. First, we report the development of isotype-specific agglutination-PCR (ISAP), a new PCR-based method for detecting allergen-specific IgE. We then combine ISAP with antibody detection by agglutination-PCR (ADAP) (Tsai et al. (2016) ACS Cent Sci 2:139-147) and proximity ligation assay (PLA) (Fredriksson et al. (2007) Nat Methods 4:327-329) into a single platform. This multiplexed assay simultaneously detects four immunological features: total IgE, specific IgE, specific IgG4 and total anti-allergen immunoglobulin (IgG, IgM, IgE, etc.) by encoding their protein levels into unique DNA sequences, which are then detected with qPCR.

In a mouse model of peanut allergy, we demonstrate that our PCR-based approach is significantly more sensitive than ELISA and detects disease-relevant allergy markers at levels that are undetectable by ELISA. We also demonstrate that our PCR-based approach is cost-effective ($0.5/per sample/per feature) and consumes only 1 μL plasma while correlating well with ImmunoCAP in analyzing a peanut allergy patient cohort.

Results

Detecting the Allergic Immunoglobulin Response with PCR-Based Assays.

We integrated three antibody-detecting methods to produce a comprehensive allergy assay.

First, we created a proximity ligation assay (PLA) to detect total IgE levels (Fredriksson et al., supra). PLA employs a pair of antibody-DNA conjugates to detect target antigens. In this case, we used a pair of polyclonal anti-IgE antibody-DNA conjugates to detect IgE. The antibody-DNA conjugates bind to multiple sites on the same IgE molecule, positioning single-stranded DNA (ssDNA) on the conjugates within close proximity. The addition of a short bridging oligonucleotide and DNA ligase links the two nearby strands into a full-length amplicon. Analysis with qPCR determines the amount of reconstituted amplicon, which reflects the abundance of IgE molecules in the sample.

Second, we used a previously developed assay (antibody detection by agglutination-PCR; ADAP) to detect levels of total anti-allergen antibodies. 13 Allergen-binding antibodies agglutinate synthetic allergen-DNA conjugates into a large immune complex, positioning the attached DNA strands into close proximity, enabling ligation and quantification with qPCR.

Detection of anti-allergen antibodies helps establish a complete view of the allergic response, where other tests in isolation might provide a misleading or incomplete picture. For example, some patients may be negative for sIgE and sIgG4, but still have high levels of total anti-allergen antibodies due to the presence of other antibody isotypes. These subgroups might display different clinical behavior than those who are negative for all isotypes. Thus, the inclusion of total anti-allergen antibodies helps classify allergic reactions, especially for patients undergoing immunotherapy.

Third, we report the development of a new PCR based assay, termed isotype-specific agglutination-PCR (ISAP) for the detection of allergen-specific IgE and IgG4. ISAP uses an antibody-binding agent-DNA conjugate with an allergen-DNA conjugate to detect the isotype of antibodies against a particular allergen. If the anti-allergen antibody is not of IgE isotype, the anti-IgE-DNA conjugate will not be present in the immune complex, precluding ligation and signal generation. Similarly, if the antibody is IgE, but does not bind onto the allergen, the allergen-DNA conjugate will be excluded from the immune complex and yield no signal. Only if the antibody is IgE and binds to the target allergen will the two DNA-conjugates unite on the same molecule for efficient ligation into a full-length amplicon. We also extend this technology to detect sIgG4 by using anti-IgG4-DNA and allergen-DNA conjugates.

Each allergy feature can then be interrogated by using appropriate primer pairs in an integrated PCR-based assay. For example, 1F1R reports total IgE, 2F2R shows the levels of total anti-allergen antibodies, while 2F1R quantifies sIgE levels. This barcoding approach not only allows deep investigation of the immunoglobulin response against one allergen, but also permits the surveillance of multiple allergen components all at once.

Synthesis of Allergen-DNA and Antibody-DNA Conjugates.

The core reagents for our PCR-based assays are high quality allergen-DNA and antibody-DNA conjugates (Tsai et al., supra).

For allergen-DNA conjugates, we use recombinantly expressed or purified allergen molecules. The allergen is cross-linked with ssDNA using a small molecule cross-linker called sulfo-SMCC, which attaches thiol-functionalized ssDNA to lysine residues on the surface of allergens. These conjugates typically bear 2.5 strands of ssDNA per allergen molecule as determined by gel analysis and UV-VIS spectrometry. This amount of ssDNA loading is sufficient to generate strong assay signal while not blocking antigenic epitopes on the allergens (Tsai et al., supra).

The antibody-DNA are synthesized using the same strategy. Specifically, we use purified polyclonal anti-IgE and anti-IgG4 antibodies in this study. The resulting conjugates are also verified by gel and UV-VIS analysis.

Workflow of PCR-Based Allergic Response Detection.

The detection of allergy-related antibodies with our integrated PCR-based approach consists of three steps. (1) First, 1 µL of sample is mixed with 2 µL of DNA conjugate probes and incubated at 37° C. for 30 minutes. During this incubation step, probes bind to analytes in the sample, bringing ssDNA on probes into close proximity. (2) Next, a ligation master mix containing DNA ligase and a short bridge DNA is added. If probes are appropriately clustered by target analytes, the bridge DNA hybridizes to two nearby ssDNA and triggered the ligation by DNA ligase. Notably, since each ssDNA on probes only has one primer binding site, the probe itself cannot be amplified by PCR. Thus, only ligated DNA will have two primer sites competent for PCR amplification. (3) The ligated DNA are pre-amplified by PCR and then analyzed by real-time qPCR. The pre-amplification step has been shown to enhance the assay reproducibility by increasing copy numbers of DNA before qPCR step (Tsai et al., supra).

In addition, a buffer only negative control is always run alongside. The $\Delta Ct$ value shows the difference between Ct value of the analyte-containing and buffer-only samples. Thus, the buffer-only sample serves as a point-of-reference to correct for variations between assays (Tsai et al., supra). The $\Delta Ct$ value is proportional to the amount of target analyte in the samples.

In summary, the workflow for our assay only requires serial addition of key reagents. The assay is performed with readily available real-time qPCR thermocyclers. We foresee these simple requirements will help promote the adoption of the technology in research and clinical labs.

Validation of Allergen-Specific IgE Detection by ISAP

To validate whether isotype-specific agglutination-PCR (ISAP) faithfully detects antibodies of specific isotypes, we obtained highly purified IgE and IgG antibodies against ovalbumin (OVA) protein. We prepared serial dilutions of both antibodies in buffer and subject them to ISAP assay using anti-IgE-1B and OVA-2A as probes.

As expected, we observed a concentration-dependent signal for the serially diluted IgE anti-OVA and no signal for IgG anti-OVA. The detection limit for the IgE anti-OVA is 12 attomole. Thus, ISAP indeed sensitively and specifically detects antibody-antigen binding in an isotype-specific manner.

To further challenge specificity of ISAP, we prepared a dilution series of non-specific IgE that lacks affinity for OVA. As expected, no signal was observed from ISAP assay. This demonstrates ISAP indeed only responds to IgE antibodies against the specified allergen, but not random and non-specific IgE molecules.

Importantly, we compare analytical sensitivity of ISAP to ELISA by testing the same dilution series of IgE anti-OVA antibodies. Improved sensitivity can reduce the sample consumption and increases the likelihood of observing even low levels of disease-relevant IgE antibodies. These joint features are of special interest to researchers using mouse models to study allergy responses, as tail/eye bleeds yield very small amounts of serum/plasma. The ISAP assay allows more frequent sample collections or more types of assays to be run by consuming only 1 µL sample per test.

Multiplex Detection of Allergy Responses by Integrated PCR-Assays

Integration of PLA, ADAP and ISAP would allow simultaneous monitoring of total IgE, total anti-allergen antibodies, allergen-specific IgE and IgG4 in a single assay. As a proof-of-concept experiment, we again prepared dilution series of IgE anti-OVA, IgG anti-OVA and non-specific IgE antibodies.

In contrast to singleplex assays, the multiplex probe panels included anti-IgE-1A, anti-IgE-1B, OVA-2A and OVA-2B. The presence of any IgE molecules would trigger the generation of 1A-1B DNA, any anti-OVA antibodies would lead to 2A-2B DNA and only IgE anti-OVA would form either 1A-2B or 2A-1B DNA. Thus, we can simultaneously quantify all three in a single assay by proper selection of primer pairs.

As expected, 1A-1B only shows concentration-dependent signal when assaying either IgE anti-OVA or non-specific IgE. 2A-2B only shows concentration-dependent signal when assaying either IgE anti-OVA or IgG anti-OVA. 2A-1B only shows signals when testing IgE anti-OVA.

Although one might have expected 2A-1B and 1A-2B both would be specific for IgE anti-OVA, we observed that 1A-2B was not as specific as 2A-1B. In other words, 1A-2B showed cross-talk when assaying IgG anti-OVA at high concentrations. Thus, it is preferable to use 2A-1B to assay allergen-specific IgE antibodies. These experiments demonstrate that multiplex detection of diverse allergic information can be achieved by proper choice of primer pairs.

Detection of Allergic Responses in Ovalbumin-Sensitized Mice Using 1 µL Sample by PCR-Based Assays We next sought to benchmark PCR-based assay performance using OVA-sensitized mouse allergy model (Nakae et al. (2007) J. Allergy Clin. Immunol. 119:680-686). The OVA-sensitized mouse group was sensitized with two OVA doses at day 0 and 14. Samples were collected via tail bleeding every 7 days. The control group mouse was injected with PBS vehicle and samples were collected as before. Importantly, to further investigate the compatibility of sample type for PCR-based approach, we collect both whole blood and serum samples for all time points from each mouse.

To perform the multiplex PCR-based analysis, we used anti-IgE-1A, anti-IgE-1B, OVA-2A, OVA-2B as the probe. This panel allowed us to detect tIgE, sIgE for OVA and total immunoglobulin against OVA. Briefly, we incubated 1 µL samples with the probes, added the ligation mix, pre-amplified by PCR and then analyzed by qPCR.

For serum samples, we observed a significant elevation of total IgE signals starting at day 7. We also observed anti-OVA sIgE at day 14. Total immunoglobulin against OVA was observed at day 7. To further validate the allergy response observed by PCR-based approach, we analyzed the same sets of samples with ELISA for sIgE against OVA. As expected, sIgE is observed at day 14 by ELISA, which coincided with PCR-based approach. Importantly, the ELISA based assay consumed 20 µL serum whereas PCR-based approach only used 1 µL serum each time.

We also investigated the compatibility of our PCR-based approach with whole blood samples. Whole blood could be advantageous compared to serum because it does not require the labor-intensive and time-consuming separation process (Ramakrishnan et al. (2008) J. Diabetes Sci. Technol. 2:242-243). Besides, a whole blood sample can be transferred from lab-to-lab at room temperature as a dried blood spot, which significantly reduces shipping costs (Ramakrishnan et al., supra).

For the whole blood samples, a similar allergy profile to serum samples was observed. Total IgE shows up at day 7, specific IgE against OVA shows up at day 14 and total immunoglobulin against OVA was observed at day 7. Importantly, the signals measured using serum and whole blood samples show a high degree of correlation (R=0.9).

These experiments demonstrate that PCR-based analysis is compatible with both serum and whole blood samples. The PCR-based approach can faithfully reveal allergy information while consuming much smaller sample volumes than ELISA.

PCR-Based Detection of Multiple Peanut Component IgE is More Sensitive than ELISA in Mouse Models We next sought to demonstrate that our PCR-based approach could reveal allergic information for multiple peanut components (Ara h1, h2 and h3) in a single assay. Both B6 and BALB mice were epicutaneously sensitized with peanut oil for six consecutive weeks. Serum samples were collected at day 0 and day 45. The successful induction of peanut allergy was verified by anaphylaxis after an intravenous high-dose of peanut extract.

In this highly multiplexed PCR-based analysis, we used anti-IgE-1A, anti-IgE-1B, Ara-h1-2A, Ara-h1-2B, Ara-h2-3A, Ara-h2-3B, Ara-h3-4A and Ara-h3-4B as probes. We analyzed 1 µL of mouse serum samples and observed strongly elevated signal for total IgE and sIgE against Ara-h1 after sensitization. Elevated signals for Ara-h2 are observed but do not reach statistical significance. This result recapitulates previous results that whole peanut skin sensitization leads to strong production of Ara-h1 specific IgE in mouse models (Smit et al. (2015) Clin. Transl. Allergy 5:13). Importantly, when assaying the same sets of mouse serum by ELISA for peanut-specific IgE, no responses were observed after sensitization. This result highlights the ability of our PCR-based assay over a standard ELISA to detect very low levels of IgE analytes.

Interestingly, when both BALB and B6 mice are subjected to the skin sensitization, a qualitatively stronger response is observed for BALB mice than B6 mice. This result is also in line with the current understanding that BALB mice generate stronger Th2 responses and thus are more susceptible to IgE induction (Sahu et al. (2010) PLoS One 5:e11348).

To further validate that results observed by PCR-based analysis are due to the induction of specific IgE by peanut sensitization, we epicutaneously sensitized both Jh and Rag knockout mice with the same protocol. These two strains of mice cannot produce immunoglobulins and thus should not generate sIgE against peanut components (Lansford et al. (1998) Int. Immunol. 10:325-332, Chen et al. (1993) Int. Immunol. 5:647-656). As expected, when we analyzed serum samples from Jh and RAG mice, no statistically significant differences were observed after sensitization.

Here we demonstrated that our PCR-based approach can analyze allergy information for multiple peanut components in a single assay. The enhanced sensitivity of PCR-based approach observes relevant signals that are not detectable by traditional ELISA. Also, the signal observed is indeed specific because no signal is observed in the immune-compromised mouse strains.

Multiplex Analysis of Peanut Allergic Responses Using 1 µL Patient Plasma and Correlation to ImmunoCAP.

Finally, we sought to demonstrate that the PCR-based assay could faithfully capture an immune-response against peanut allergy using clinical patient samples and correlate the result to ImmunoCAP.

We obtained 20 baseline patient samples from the POISED clinical trials (Mukai et al. (2016) J. Allergy Clin. Immunol. S0091-6749:30613-3), which was designed to investigate the efficacy of peanut oral immunotherapy for attenuating allergy responses. Here we used a previously described multiplex panel of anti-IgE-DNA, Ara h1-DNA, Ara-h2-DNA and Ara-h3-DNA probe pairs. In addition, we included anti-IgG4-DNA conjugates to detect sIgG4 against peanut components.

Satisfyingly, our PCR-based approach successfully tracked 10 allergic parameters from only 1 µL patient plasma. Importantly, the specific IgE signal for Ara h1, h2 and h3 correlates very well with ImmunoCAP (R=0.82 for Ara h1, 0.92 for Ara h2 and 0.84 for Ara h3).

These results demonstrate that the PCR-based approach is at least as effective as the gold standard ImmunoCAP platform, but with key advantages, including cost effectiveness and reduced sample consumption. For instance, the same information gathered using ImmunoCAP would require 400 µL of patient plasma. Our integrated PCR-based approach only requires 1 µL and detects all these parameters in a single assay. In addition, the high amount of antigen required per ImmunoCAP assay elevates the cost of this format to about $500, whereas the material cost of our PCR-based approach is about $5. Future studies are underway to examine the precise clinical sensitivity and specificity of the PCR-based approach with additional allergens and patient samples.

Discussion

We report ISAP, a newly developed PCR-based method to detect antigen-binding antibodies of a specific isotype. We further couple ISAP with other PCR-based methods into a single assay. This integrated PCR-based approach detects total IgE, specific IgE, specific IgG4 and total anti-allergen antibodies in one multiplexed assay.

Our PCR-based approach for allergy detection enjoys several merits. First, it leverages the high specificity of component-resolved allergy diagnostics by using individual allergen protein-DNA conjugate as probes. Second, it is highly multiplexable via DNA barcoding, allowing simultaneous detection of responses against multiple allergen components. Third, it exhibits greatly improved analytical sensitivity due to the exponential amplification of PCR. Fourth, our PCR-based approach consumes a minute amount of sample (1 µL), which aids in testing pediatric patients. Fifth, the material cost for PCR-based assay is very low ($0.5/per sample/per feature) in comparison to gold-standard allergen assays. Finally, the workflow for PCR-based approach is operationally simple and does not require specialized equipment.

ImmunoCAP assays are accepted as the gold standard for sIgE measurement. Here we demonstrated that our PCR-based antibody tests correlated well with ImmunoCAP in analyzing clinical patient samples. Importantly, our PCR-based approach costs less than $5 per test. A comparable ImmunoCAP assay costs more than $500. Furthermore, the PCR-based approach only uses 1 µL of plasma, in comparison to the 400 µL required by ImmunoCAP. The significant cost reduction may promote widespread adoption of component-resolved allergy diagnostics.

A sister technology to the ImmunoCAP platform is the ISAC technology (Chapman et al. (2015) Curr. Allergy Asthma Rep. 15:36). In contrast to the polymer-based assay used in the traditional ImmunoCAP assay, ISAC uses allergen-printed arrays to capture and detect sIgE for large numbers of allergen components. However, because less antigen is present for IgE capture, ISAC is less sensitive than ImmunoCAP. Besides, ISAC is fixed to detect 112 allergens all at once. It has been reported that such fixed multiplex format can yield confusing/misleading information (Incorvaia et al. (2015) J. Allergy Clin. Immunol. Pract. 3:879-882). Due to the DNA-barcode nature, our integrated PCR-based approach enjoys flexible multiplex power that ideally can allow detection of 1-96 allergen components depending on the needs.

However, the PCR-based approach is not without limitations. Serum samples can contain high levels of IgG antibodies against allergen (sIgG) and compete with sIgE for probe binding. We experimentally validated that our PCR-based approach can accommodate up to 1000-10000× excess sIgG. This resilience to sIgG interference compares favorably with the clinically-used ISAC format (Lupinek et al. (2014) Methods 66:106-119).

In addition, many of the samples analyzed from peanut allergy patients contained detectable levels of sIgG4. Fortunately, our PCR-based approach still accurately detected sIgE against peanut components in these samples. The sIgE levels also correlated well with ImmunoCAP. This data suggest that our PCR-based approach faithfully detects sIgE even in the presence of sIgG.

In the worst-case scenario, our PCR-based approach intrinsically detects total anti-allergen antibodies, where a false negative IgE test can be identified should total anti-allergen or IgG4 show very strong signals.

In conclusion, PCR-based allergy assays feature enhanced sensitivity, specificity, low sample consumption and assay costs and reliance on standard qPCR instruments. Our assay will show particular benefit for pediatric patients due to the reduction of sample needed to link these patients to clinical trials and other emerging therapies for better disease management. We thus envision ISAP and its allied PCR-based approaches will form the foundation for better allergy testing in the labs and clinics.

Although preferred embodiments of the subject invention have been described in some detail, it is understood that obvious variations can be made without departing from the spirit and the scope of the invention as defined herein.

What is claimed is:

1. A method of detecting a target antibody isotype in a sample, the method comprising:

a) contacting the sample with i) an antibody-binding agent conjugated to a first DNA molecule comprising a first portion of a barcode, wherein the antibody-binding agent comprises an antibody, an antibody mimetic, or an aptamer that specifically binds to the target antibody isotype, and ii) an antigen conjugated to a second DNA molecule comprising a second portion of a barcode, wherein the antigen binds to the target antibody isotype in the sample, if present, and the antibody-binding agent specifically binds to the target antibody isotype resulting in formation of a complex;

b) connecting the first DNA molecule to the second DNA molecule in the complex, wherein the first portion of the barcode and the second portion of the barcode are joined to form a complete barcode; and c) detecting the complete barcode as an indication of the presence of the target antibody isotype in the sample.

2. The method of claim 1, wherein said connecting comprises:

a) contacting the complex with a bridge oligonucleotide, wherein the bridge oligonucleotide comprises a first portion sufficiently complementary to and capable of hybridizing with the first DNA molecule, and a second portion sufficiently complementary to and capable of hybridizing with the second DNA molecule, wherein the first DNA molecule and the second DNA molecule are in sufficient proximity to each other in the complex to simultaneously hybridize to the bridge oligonucleotide; and b) ligating the first DNA molecule to the second DNA molecule in the complex to produce a ligation product comprising the complete barcode.

3. The method of claim 1, wherein said connecting comprises hybridization of a nucleotide sequence in the first DNA molecule to a complementary nucleotide sequence in the second DNA molecule.

4. The method of claim 3, further comprising using a polymerase to extend the hybridized first and second DNA molecules to produce a nucleic acid comprising the complete barcode, optionally wherein the polymerase is used under isothermal conditions.

5. The method of claim 1, wherein the target antibody isotype is selected from the group consisting of an immunoglobulin E (IgE), an immunoglobulin M (IgM), an immunoglobulin G (IgG), an immunoglobulin A (IgA) and an immunoglobulin D (IgD).

6. The method of claim 1, wherein said detecting is performed using polymerase chain reaction (PCR), isothermal amplification, or microarray analysis.

7. The method of claim 1, wherein the sample is obtained from a subject having an immune disorder selected from the group consisting of an allergy, an infection, an autoimmune disorder, and an inflammatory disorder.

8. The method of claim 1, further comprising adding a plurality of antibody-binding agent-DNA conjugates to the sample, wherein each antibody-binding agent is conjugated to a DNA molecule comprising a different barcode sequence and each antibody-binding agent is capable of binding to a different target antibody isotype to allow multiplex detection of a plurality of target antibody isotypes in the sample.

9. The method of claim 8, wherein the antibody-binding agent-DNA conjugates are selected from the group consisting of an anti-IgE secondary antibody-DNA conjugate for detection of IgE, an anti-IgM secondary antibody-DNA conjugate for detection of IgM, an anti-IgG secondary antibody-DNA conjugate for detection of IgG, an anti-IgA secondary antibody-DNA conjugate for detection of IgA, and an anti-IgD secondary antibody DNA conjugate for detection of IgD.

10. The method of claim 1, wherein the antigen is selected from the group consisting of an allergen, an autoimmune disease antigen, a cancer antigen, and a pathogen antigen.

11. The method of claim 1, wherein the sample is blood, plasma, or serum.

12. The method of claim 1, wherein the antibody that specifically binds to the target antibody isotype is selected from the group consisting of a monoclonal antibody, a polyclonal antibody, a chimeric antibody, a nanobody, a recombinant fragment of an antibody, an Fab fragment, an Fab' fragment, an F(ab')2 fragment, an Fv fragment, and an scFv fragment.

13. The method of claim 1, wherein the antibody that specifically binds to the target antibody isotype is selected from the group consisting of an anti-IgE antibody, an anti-IgM antibody, an anti-IgG antibody, an anti-IgA antibody, and an anti-IgD antibody.

14. The method of claim 1, further comprising quantitating the amount of the target antibody isotype.

15. The method of claim 14, wherein said quantitating comprises performing quantitative PCR (qPCR).

16. The method of claim 7, wherein the immune disorder is selected from the group consisting of an allergy, an infection, an autoimmune disorder, and an inflammatory disorder.

* * * * *

UNITED STATES PATENT AND TRADEMARK OFFICE
CERTIFICATE OF CORRECTION

| | | |
|---|---|---|
| PATENT NO. | : 11,656,233 B2 | Page 1 of 1 |
| APPLICATION NO. | : 16/497668 | |
| DATED | : May 23, 2023 | |
| INVENTOR(S) | : Carolyn Bertozzi et al. | |

It is certified that error appears in the above-identified patent and that said Letters Patent is hereby corrected as shown below:

In the Specification

Column 1, Line 8, "contracts DK108781 and AR067145" should be corrected to read --contract DK108781--.

Signed and Sealed this
Eighteenth Day of November, 2025

John A. Squires
*Director of the United States Patent and Trademark Office*